US011873319B2

(12) United States Patent
Vance et al.

(10) Patent No.: US 11,873,319 B2
(45) Date of Patent: Jan. 16, 2024

(54) CYCLIC DI-NUCLEOTIDE INDUCTION OF TYPE I INTERFERON

(71) Applicant: The Regents of the University of California, Oakland, CA (US)

(72) Inventors: Russell E. Vance, Albany, CA (US); Ming C. Hammond, Berkeley, CA (US); Dara Burdette, Berkeley, CA (US); Elie J. Diner, San Rafael, CA (US); Stephen C. Wilson, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 241 days.

(21) Appl. No.: 17/464,494

(22) Filed: Sep. 1, 2021

(65) Prior Publication Data

US 2022/0081464 A1 Mar. 17, 2022

Related U.S. Application Data

(63) Continuation of application No. 16/279,950, filed on Feb. 19, 2019, now abandoned, which is a continuation of application No. 14/268,967, filed on May 2, 2014, now abandoned.

(60) Provisional application No. 61/819,499, filed on May 3, 2013.

(51) Int. Cl.
*A01N 43/04* (2006.01)
*A61K 31/70* (2006.01)
*C07H 21/02* (2006.01)
*A61K 31/7084* (2006.01)

(52) U.S. Cl.
CPC .......... *C07H 21/02* (2013.01); *A61K 31/7084* (2013.01)

(58) Field of Classification Search
None
See application file for complete search history.

(56) References Cited

U.S. PATENT DOCUMENTS

| | | | |
|---|---|---|---|
| 5,547,941 A | 8/1996 | Battistini et al. |
| 5,637,483 A | 6/1997 | Dranoff et al. |
| 5,698,432 A | 12/1997 | Oxford |
| 5,904,920 A | 5/1999 | Dranoff et al. |
| 5,985,290 A | 11/1999 | Jaffee et al. |
| 6,033,674 A | 3/2000 | Jaffee et al. |
| 6,090,611 A | 7/2000 | Covacci et al. |
| 6,277,368 B1 | 8/2001 | Hiserodt et al. |
| 6,350,445 B1 | 2/2002 | Jaffee et al. |
| 6,464,973 B1 | 10/2002 | Levitsky et al. |
| 6,558,670 B1 | 5/2003 | Friede et al. |
| 6,780,429 B1 | 8/2004 | Matsuyama et al. |
| 7,569,555 B2 | 8/2009 | Karaolis |
| 7,592,326 B2 | 9/2009 | Karaolis |
| 7,709,458 B2 | 5/2010 | Karaolis et al. |
| 8,012,469 B2 | 9/2011 | Levitsky et al. |
| 8,283,328 B2 | 10/2012 | Krieg et al. |
| 8,304,396 B2 | 11/2012 | Krieg et al. |
| 8,367,716 B2 | 2/2013 | Karaolis |
| 8,450,293 B2 | 5/2013 | Jones et al. |
| 9,061,048 B2 | 6/2015 | Portnoy et al. |
| 9,090,646 B2 | 7/2015 | Jones et al. |
| 9,549,944 B2 | 1/2017 | Dubensky, Jr. et al. |
| 10,106,574 B2 | 10/2018 | Altman et al. |
| 2001/0041682 A1 | 11/2001 | Stutts, III et al. |
| 2002/0140414 A1 | 10/2002 | Sohn et al. |
| 2002/0150588 A1 | 10/2002 | Allison et al. |
| 2003/0003092 A1 | 1/2003 | Krissansen et al. |
| 2003/0138413 A1 | 7/2003 | Vicari et al. |
| 2005/0281783 A1 | 12/2005 | Kinch et al. |
| 2006/0040887 A1 | 2/2006 | Karaolis |
| 2006/0286549 A1 | 12/2006 | Sohn et al. |
| 2007/0059683 A1 | 3/2007 | Barber et al. |
| 2007/0224210 A1 | 9/2007 | Krieg et al. |
| 2007/0244059 A1 | 10/2007 | Karaolis |
| 2007/0281897 A1 | 12/2007 | Karaolis |
| 2008/0076778 A1 | 3/2008 | Ossovskaya |
| 2008/0286296 A1 | 11/2008 | Ebensen et al. |
| 2010/0150946 A1 | 6/2010 | Jooss et al. |
| 2010/0310602 A1 | 12/2010 | Reed et al. |
| 2011/0081674 A1 | 4/2011 | Han |
| 2011/0262485 A1 | 10/2011 | Barber |
| 2011/0287948 A1 | 11/2011 | Suresh |

(Continued)

FOREIGN PATENT DOCUMENTS

| | | |
|---|---|---|
| JP | 2010529984 | 9/2010 |
| WO | WO 2005030186 | 4/2005 |

(Continued)

OTHER PUBLICATIONS

Sun, Lijun, et al. "Cyclic GMP-AMP synthase is a cytosolic DNA sensor that activates the type I interferon pathway." Science 339. 6121 (2013): 786-791.*
Ablasser A, Goldeck M, Cavlar T, Deimling T, Witte G, Röhl I, Hopfner KP, Ludwig J, Hornung V. cGAS produces a 2'-5'-linked cyclic dinucleotide second messenger that activates STING. Nature. Jun. 20, 2013;498(7454):380-4. doi: 10.1038/nature12306. Epub May 30, 2013. PMID: 23722158; PMCID: PMC4143541.*
Abe et al. "STING Recognition of Cytoplasmic DNA Instigates Cellular Defense," Mol Cell. Apr. 11, 2013; 50(1), pp. 1-21.
Adams et al. "PHENIX: a comprehensive Python-based system for macromolecular structure solution," Acta Cryst. (2010) D66, 213-221.
Ahn et al. "STING manifests self DNA-dependent inflammatory disease," PNAS (Nov. 20, 2012), vol. 109, No. 47, pp. 19386-19391.

(Continued)

*Primary Examiner* — Patrick T Lewis
(74) *Attorney, Agent, or Firm* — Bret E. Field; Bozicevic, Field & Francis LLP

(57) ABSTRACT

Methods and compositions are provided for increasing the production of a type I interferon (IFN) in a cell. Aspects of the methods include increasing the level of a 2'-5' phosphodiester linkage comprising cyclic-di-nucleotide in a cell in a manner sufficient to increase production of the type I interferon (IFN) by the cell. Also provided are compositions and kits for practicing the embodiments of the methods.

18 Claims, 12 Drawing Sheets

Specification includes a Sequence Listing.

(56) References Cited

U.S. PATENT DOCUMENTS

| | | |
|---|---|---|
| 2012/0041057 A1 | 2/2012 | Jones et al. |
| 2012/0164107 A1 | 6/2012 | Portnoy et al. |
| 2012/0178710 A1 | 7/2012 | Jones et al. |
| 2014/0155345 A1 | 6/2014 | Jones et al. |
| 2014/0205653 A1 | 7/2014 | Dubensky, Jr. |
| 2014/0329889 A1 | 11/2014 | Vance et al. |
| 2014/0341976 A1 | 11/2014 | Dubensky, Jr. |
| 2015/0056224 A1 | 2/2015 | Dubensky, Jr. |
| 2016/0068560 A1 | 3/2016 | Patel et al. |
| 2016/0210400 A1 | 7/2016 | Patel et al. |

FOREIGN PATENT DOCUMENTS

| | | |
|---|---|---|
| WO | WO 2005039535 | 5/2005 |
| WO | WO 2005087238 | 9/2005 |
| WO | WO 2005089777 | 9/2005 |
| WO | WO 2007054279 | 5/2007 |
| WO | WO 2007/064945 A2 | 6/2007 |
| WO | WO 2009/133560 A1 | 11/2009 |
| WO | WO 2010017248 | 2/2010 |
| WO | WO 2010067262 | 6/2010 |
| WO | WO 2010/104883 A1 | 9/2010 |
| WO | WO 2010104833 | 9/2010 |
| WO | WO 2011003025 | 1/2011 |
| WO | WO 2011136828 | 11/2011 |
| WO | WO 2011139769 | 11/2011 |
| WO | WO 2012068360 | 5/2012 |
| WO | WO 2012088155 | 6/2012 |
| WO | WO 2012139209 | 10/2012 |
| WO | WO2013036032 | 3/2013 |
| WO | WO 2013086331 | 6/2013 |
| WO | WO 2013166000 | 11/2013 |
| WO | WO 2013185052 | 12/2013 |
| WO | WO 2014093936 | 6/2014 |
| WO | WO 2014099824 | 6/2014 |
| WO | WO 2014179335 | 11/2014 |
| WO | WO2014179335 | 11/2014 |
| WO | WO 2014179760 | 11/2014 |
| WO | WO 2014189805 | 11/2014 |
| WO | WO 2014189806 | 11/2014 |
| WO | WO 2015017652 | 2/2015 |
| WO | WO 2015061294 | 4/2015 |
| WO | WO 2015074145 | 5/2015 |
| WO | WO 2015077354 | 5/2015 |
| WO | WO 2015108595 | 7/2015 |
| WO | WO 2015185565 | 12/2015 |
| WO | WO2017027645 | 2/2017 |
| WO | WO2017027646 | 2/2017 |

OTHER PUBLICATIONS

Apetoh et al. "Toll-like receptor 4-dependent contribution of the immune system to anticancer chemotherapy and radiotherapy," Nature Medicine, vol. 13, No. 9 (Sep. 2007), pp. 1050-1058.

Baguley et al. "DMXAA: an antivascular agent with multiple host responses," Int. J. Radiation Oncology Biol. Phys. (2002), vol. 54, No. 5, pp. 1503-1511.

Blank et al. "PD-LI/B7H-1 Inhibits the Effector Phase of Tumor Rejection by T Cell Receptor (TCR) Transgenic CD8+ T Cells," Cancer Research, Feb. 1, 2004, vol. 64, No. 3, pp. 1140-1145.

Burckstummer et al. "An orthogonal proteomic-genomic screen identifies AIM2 as a cytoplasmic DNA sensor for the inflammasome," Nat. Immunol., vol. 10, No. 2, pp. 266-272 (Mar. 2009).

Cai et al. "The cGAS-cGAMP-STING Pathway of Cytosolic DNA Sensing and Signaling," Mol. Cell 54, (Apr. 24, 2014), pp. 289-296.

Cavlar et al. "Species-specific detection of the antiviral small-molecule compound CMA by STING," EMBO J. (2013), vol. 32, No. 10, pp. 1440-1450.

Corrales et al. "Extremely potent immunotherapeutic activity of a STING agonist in the B16 melanoma model in vivo," J Immunother Cancer (2013), 1 (Suppl 1):O15, 1 page.

Dai et al. "Modified vaccinia virus Ankara triggers type I IFN production in murine conventional dendritic cells via a cGAS/STING-mediated cytosolic DNA-sensing pathway," PLoS Pathogens, vol. 10, Issue 4, e1003989, 13 pages (Apr. 2014).

Danilchanka et al. "Cyclic Dinucleotides and the Innate Immune Response," Cell, vol. 154, No. 5, pp. 962-970 (2013).

Diamond et al. "Type I interferon is selectively required by dendritic cells for immune rejection of tumors," J. Exp. Med. (Sep. 26, 2011), vol. 208, No. 10, pp. 1989-2003.

Decision to Grant dated Nov. 6, 2018 for Japanese Patent Application No. 2016-514151, 5 pages.

Donovan et al. "Structural basis for cytosolic double-stranded RNA surveillance by human oligoadenylate synthetase 1," PNAS, Jan. 29, 2013, vol. 110, No. 5, pp. 1652-1657.

Dubensky et al. "Development of Cyclic Dinucleotides as STING-Targeted Molecular Adjuvants," 2012 Annual Meeting of the Society for Immunotherapy of Cancer, Presented Dec. 14, 2012, 13 pages.

Egli et al. "Atomic-resolution structure of the cellulose synthase regulator cyclic diguanylic acid," PNAS (Apr. 1990), vol. 87, pp. 3235-3239.

Ekins et al, In silico pharmacology for drug discovery: methods for virtual ligand screening and profiling. Br J Pharmacol. (2007), 152(1); 9-20.

Emsley et al. "Features and development of Coot,"Acta Cryst. (2010) D66, pp. 486-501.

Fernandes-Alnemri et al. "AIM2 activates the inflammasome and cell death in response to cytoplasmic DNA," Nature (Mar. 26, 2009), vol. 458, No. 7237, pp. 509-513.

Fridman et al. "The immune contexture in human tumours: impact on clinical outcome," Nature Reviews (Apr. 2012), vol. 12, pp. 298-306.

Fuertes et al. "Host type I IFN signals are required for antitumor CD8+ T cell responses through CD8α+ dendritic cells," J. Exp. Med. (Sep. 26, 2011), vol. 208, No. 10, pp. 2005-2016.

Fuertes et al. "Type I interferon response and innate immune sensing of cancer," Trends Immunol. (Feb. 2013), vol. 34, No. 2, pp. 67-73.

Gaffney et al. "One-Flask Synthesis of Cyclic Diguanosine Monophosphate (c-di-GMP)," Current Protocols in Nucleic Acid Chemistry 14.8.1-14.8.17 (Mar. 2012), 7 pages.

Gajewski, T. "Identifying and overcoming immune resistance mechanisms in the melanoma tumor microenvironment," Clin Cancer Res. (Apr. 1, 2006), vol. 12(7 Suppl), pp. 2326s-2330s.

Gajewski et al. "Gene signature in melanoma associated with clinical activity: a potential clue to unlock cancer immunotherapy," Cancer J. (Jul./Aug. 2010), vol. 16, No. 4, pp. 399-403.

Gajewski et al. "Cancer immunotherapy strategies based on overcoming barriers within the tumor microenvironment," Current Opinion in Immunology 2013, vol. 25, pp. 268-276. Available online Apr. 8, 2013.

Gall et al. "Autoimmunity initiates in non-hematopoietic cells and progresses via lymphocytes in an IFN-dependent autoimmune disease," Immunity (2012), vol. 36, No. 1, pp. 120-131.

Galon et al. "Type, density, and location of immune cells within human colorectal tumors predict clinical outcome," Science (Sep. 29, 2006), vol. 313, No. 5795, pp. 1960-1964.

Gao et al. "Binding-pocket and lid-region substitutions render human STING sensitive to the species-specific drug DMXAA," Cell Reports (2014) 8(6):1668-1676 (2014).

Gehrke et al. "Oxidative Damage of DNA Confers Resistance to Cytosolic Nuclease TREX1 Degradation and Potentiates STING-Dependent Immune Sensing," Immunity 39 (Sep. 19, 2013), pp. 482-495.

Ghiringhelli et al. "Activation of the NLRP3 inflammasome in dendritic cells induces IL-1 β-dependent adaptive immunity against tumors," Nature Medicine (Oct. 2009), vol. 15, No. 10, pp. 1170-1178.

Gao, et al."Cyclic [G(2',5')pA(3',5')p] is the metazoan second messenger produced by DNA-activated cyclic GMP-AMP synthase", Cell. May 23, 2013;153(5):1094-107.

Gray et al. "Evidence for cyclic diguanylate as a vaccine adjuvant with novel immunostimulatory activities," Cellular Immunology 278 (2012), pp. 113-119.

(56) References Cited

OTHER PUBLICATIONS

Hamid et al. "A prospective phase II trial exploring the association between tumor microenvironment biomarkers and clinical activity of ipilimumab in advanced melanoma," J. Transl. Med., vol. 9, No. 204, Nov. 28, 2011, pp. 1-16.
Harlin et al. "Chemokine expression in melanoma metastases associated with CD8+ T-cell recruitment," Cancer Research, vol. 69, No. 7, Apr. 1, 2009, pp. 3077-3085.
Hartmann et al. "Crystal structure of the 2'-specific and double-stranded RNA-activated interferon-induced antiviral protein 2'-5'-oligoadenylate synthetase," Mol. Cell, vol. 19, Nov. 2003, pp. 1173-1185.
Head et al. "The development of the tumor vascular-disrupting agent ASA404 (vadimezan, DMXAA): current status and future opportunities," Expert Opin. Investig. Drugs (2010), vol. 19, No. 2, pp. 295-304.
Henry et al. "Type I interferon signaling is required for activation of the inflammasome during *Francisella* infection," J Exp Med., vol. 204, No. 5, May 14, 2007, pp. 987-994.
Higashida et al. "Measurement of adenylyl cyclase by separating cyclic AMP on silica gel thin-layer chromatography," Anal. Biochem. 308 (2002), pp. 106-111.
Hoebe et al. "Upregulation of costimulatory molecules induced by lipopolysaccharide and double-stranded RNA occurs by Trif-dependent and Trif-independent pathways," Nature Immunology, vol. 4, No. 12, 2003, pp. 1223-1229.
Hornung et al. "AIM2 recognizes cytosolic dsDNA and forms a caspase-1-activating inflammasome with ASC," Nature, vol. 458, No. 7237, Mar. 26, 2009, pp. 514-518.
Hornung et al. "Intracellular DNA recognition," Nat. Rev. Immunol., vol. 10, Feb. 2010, pp. 123-130.
Huang et al. Nature Structural & Molecular Biology, Supplementary Information, 1-5 (2012).
Huffman et al. "Prokaryotic transcription regulators: more than just the helix-turn-helix motif," Curr Opin Struct Biol 12 (2002), pp. 98-106.
Hwang et al. "Prognostic significance of tumor-infiltrating T cells in ovarian cancer: a meta-analysis," Gynecol Oncol., vol. 124, No. 2, Feb. 2012, pp. 192-198.
Ishii et al. "A toll-like receptor-independent antiviral response induced by double-stranded B-form DNA," Nature Immunology, vol. 7, No. 1, Jan. 2006, pp. 40-48.
Ishikawa et al. "STING regulates intracellular DNA-mediated, type I interferon-dependent innate immunity," Nature, vol. 461, No. 7265, Oct. 8, 2009, pp. 788-792.
Jin et al. "MPYS, a novel membrane tetraspanner, is associated with major histocompatibility complex class II and mediates transduction of apoptotic signals," Mol. Cell Biol., vol. 28, No. 16, Aug. 2008, pp. 5014-5026.
Jin et al. "Structures of the HIN domain: DNA complexes reveal ligand binding and activation mechanisms of the AIM2 inflammasome and IFI16 receptor," Immunity, vol. 36, Apr. 20, 2012, pp. 561-571.
Jounai et al. "Recognition of damage-associated molecular patterns related to nucleic acids during inflammation and vaccination," Frontiers in Cellular and Infection Microbiology, vol. 2, No. 168, Jan. 2013, pp. 1-13.
Kawarada et al. "NK- and CD8+ T cell-mediated eradication of established tumors by peritumoral injection of CpG-containing oligodeoxynucleotides," J Immunol., vol. 167, No. 9, Nov. 2001, pp. 5247-5253.
Keating et al. "Cytosolic DNA sensors regulating type I interferon induction," Trends Immunol., vol. 32, No. 12, Dec. 2011, pp. 574-581.
Kerur et al. "IFI16 acts as a nuclear pathogen sensor to induce the inflammasome in response to Kaposi Sarcoma-associated herpesvirus infection," Cell Host & Microbe, vol. 9, May 19, 2011, pp. 363-375.
Kim et al. "Anticancer flavonoids are mouse-selective STING agonists," ACS Chem Biol., vol. 8, No. 7, Jul. 19, 2013, pp. 1396-1401.
Kodym et al. "2'-5'-Oligoadenylate synthetase is activated by a specific RNA sequence motif," Biochem. Biophys. Res. Commun. 388 (2009), pp. 317-322.
Konno et al. "Cyclic di nucleotides trigger ULKI (ATGI) phosphorylation of STING to prevent sustained innate immune signaling," Cell, vol. 155, No. 3, Oct. 24, 2013, pp. 688-698.
Kono et al. "How dying cells alert the immune system to danger," Nat Rev Immunol., vol. 8, No. 4, Apr. 2008, pp. 279-289.
Krasteva et al. "Sensing the messenger: the diverse ways that bacteria signal through c-di-GMP," Protein Science, vol. 21, 2012, pp. 929-948.
Kroemer et al. "Immunogenic Cell Death in Cancer Therapy,"Annu. Rev. Immunol. 2013, vol. 31, pp. 51-72.
Kubota et al. "Identification of 2'-phophodiesterase, which plays a role in 2-5A system regulated by interferon," J. Biol. Chem., vol. 279, No. 36, Sep. 3, 2004, pp. 37832-37841.
Kulshina et al. "Recognition of the bacterial second messenger cyclic diguanylate by its cognate riboswitch," Nat. Struct. Mol. Biol., vol. 16, No. 12, Dec. 2009, pp. 1212-1217.
Lande et al. "Plasmacytoid dendritic cells sense self-DNA coupled with antimicrobial peptide," Nature, vol. 449, Oct. 4, 2007, pp. 564-570.
Lara et al. "Randomized phase III placebo-controlled trial of carboplatin and paclitaxel with or without the vascular disrupting agent vadimezan (ASA404) in advanced non-small-cell lung cancer," J. Clin. Oncol., vol. 29, No. 22, Aug. 1, 2011, pp. 2965-2971.
Lee et al. "An allosteric self-splicing ribozyme triggered by a bacterial second messenger," Science, vol. 329, Aug. 13, 2010, pp. 845-848.
Li et al. "Efficient cross-presentation depends on autophagy in tumor cells," Cancer Research, vol. 68, No. 17, Sep. 1, 2008, pp. 6889-6895.
Lunde et al. "RNA-binding proteins: modular design for efficient function," Nat. Rev. Mol Cell. Biol., vol. 8, Jun. 2007, pp. 479-490.
Mahmoud et al. "Tumor-Infiltrating CD8+ Lymphocytes Predict Clinical Outcome in Breast Cancer," J. of Clin. Oncol., vol. 29, No. 15, May 20, 2011, pp. 1949-1955.
Marichal et al. "DNA relased from dying host cells medicates aluminum adjuvant activity," Nature Medicine (Advance Online Publication), vol. 17, No. 8, Jul. 17, 2011, pp. 996-1002.
McCoy et al. "Phaser crystallographic software," J. Appl. Cryst., 40, 2007, pp. 658-674.
McKee et al. "Host DNA released in response to aluminum adjuvant enhances MHC class II-mediated antigen presentation and prolongs CD4 T-cell interactions with dendritic cells," PNAS, vol. 110, No. 12, Mar. 19, 2013, pp. E1122-E1131.
Molinero et al. "Epidermal Langerhans cells promote skin allograft rejection in mice with NF-KB-impaired T cells," Am. J. Transplant, vol. 8, No. 1, Jan. 2008, pp. 21-31.
Murshudov et al. "Refinement of macromolecular structures by the maximum-likelihood method," Acta Cryst. (1997), vol. D53, pp. 240-255.
Obeid et al. "Calreticulin exposure dictates the immunogenicity of cancer cell death," Nature Medicine, vol. 13, No. 1, Jan. 2007, pp. 54-61.
Oka et al. "Mitochondrial DNA that escapes from autophagy causes inflammation and heart failure," Nature, vol. 485, No. 7397, May 10, 2012, pp. 251-255.
Otwinowski et al. "Processing of X-Ray Diffraction Data Collected in Oscillation Mode," Methods in Enzymology, vol. 276, 1997, pp. 307-326.
Pages et al. "In Situ Cytotoxic and Memory T Cells Predict Outcome in Patients with Early-State Colorectal Cancer," J. Clin. Oncol., vol. 27, No. 35, Dec. 10, 2009, pp. 5944-5951.
Paludan et al. "Immune sensing of DNA," Immunity, vol. 38, May 23, 2013, pp. 870-880.
Rasmussen et al. "Activation of autophagy by alpha-herpesviruses in myeloid cells is mediated by cytoplasmic viral DNA through a mechanism dependent on stimulator of IFN genes," J Immunol., vol. 187, Oct. 12, 2011, pp. 5268-5276.

(56) References Cited

OTHER PUBLICATIONS

Roberson et al. "Immortalization of Cloned Mouse Splenic Macrophages with a Retrovirus Containing the v-raf/mil and v-myc Oncogenes," Cellular Immunology, vol. 116, 1988, pp. 341-351.
Roberts et al. "IFN-β-dependent inhibition of tumor growth by the vascular disrupting agent 5,6-dimethylxanthenone-4-acetic acid (DMXAA)," J. Interf. Cytok. Res., vol. 28, 2008, pp. 133-139.
Römling et al. "Cyclic di-GMP: the First 25 Years of a Universal Bacterial Second Messenger," Microbiol. Mol. Biol. Rev., vol. 77, No. 1, Mar. 2013, pp. 1-52.
Ross et al. "Regulation of cellulose synthesis in *Acetobacter xylinum* by cyclic diguanylic acid," Nature, vol. 325, Jan. 15, 1987, pp. 279-281.
Sadler et al. "Interferon-inducible antiviral effectors," Nat. Rev. Immunol., vol. 8, 2008, pp. 559-568.
Sancho et al. "Identification of a dendritic cell receptor that couples sensing of necrosis to immunity," Nature, vol. 458, No. 7240, Apr. 16, 2009, pp. 899-903.
Schirmer et al. "Structural and mechanistic determinants of c-di-GMP signaling," Nat. Rev. Microbiol., vol. 7, Oct. 2009, pp. 724-735.
Schoggins et al. "A diverse range of gene products are effectors of the type I interferon antiviral response," Nature, vol. 472, No. 7344, Apr. 28, 2011, pp. 481-485.
Shang et al. "Crystal structures of STING protein reveal basis for recognition of cyclic di-GMP," Nat. Struct. Mol. Bio., vol. 19, No. 7, Jul. 2012, pp. 725-727.
Sharma et al. "Innate immune recognition of an AT-rich stem-loop DNA motif in the *Plasmodium falciparum* genome," Immunity, vol. 35, No. 2, Aug. 26, 2011, pp. 194-207.
Slansky et al. "Enhanced antigen-specific antitumor immunity with altered peptide ligands that stabilize the MHC-peptide-TCR complex," Immunity, vol. 13, Oct. 2000, pp. 529-538.
Smith et al. "Structural basis of ligand binding by a c-di-GMP riboswitch," Nat. Struct. Mol. Biol., vol. 16, No. 12, Dec. 2009, pp. 1218-1223.
Spranger et al. "Up-regulation of PD-LI, IDO, and T(regs) in the melanoma tumor microenvironment is driven by CD8(+) T cells," Sci Transl Med., vol. 5, No. 200, Aug. 28, 2013 pp. 200ra116 (21 pages).
Stetson et al. "Recognition of cytosolic DNA activates an IRF3-dependent innate immune response," Immunity, vol. 24, Jan. 2006, pp. 93-103.
Sudarsan et al. "Riboswitches in eubacteria sense the second messenger cyclic di-GMP," Science, vol. 321, Jul. 18, 2008, pp. 411-413.
Sun et al. "ERIS, an endoplasmic reticulum IFN stimulator, activates innate immune signaling through dimerization," PNAS, vol. 106, No. 21, May 26, 2009, pp. 8653-8658.
Takaoka et al. "DAI (DLM-1/ZBP1) is a cytosolic DNA sensor and an activator of innate immune response," Nature, vol. 448, Jul. 26, 2007, pp. 501-505.
Twitty et al. "Tumor-derived autophagosome vaccine: induction of cross-protective immune responses against short-lived proteins through a p62-dependent mechanism," Clin Cancer Res., vol. 17, No. 20, Oct. 15, 2011, pp. 6467-6481.
Unterholzner et al. "IFI16 is an innate immune sensor for intracellular DNA," Nat. Immunol., vol. 11, No. 11, pp. 997-1004.
Wolchok et al. "Nivolumab plus ipilimumab in advanced melanoma," N Engl J Med., vol. 369, No. 2, Jul. 11, 2013, pp. 122-133.
Wolkowicz et al. "NF45 dimerizes with NF90, Zfr and SPNR via a conserved domain that has a nucleotidyltransferase fold," Nucleic Acids Res., vol. 40, No. 18, Jul. 24, 2012, pp. 9356-9368.
Wu et al., Supplementary Materials for "Cyclic-GMP-AMP is an Endogenous Second Messenger in Innate Immune Signaling by Cytosolic DNA," Science, vol. 339, No. 6121, Feb. 15, 2013, 21 pages.
Wu, et al. "Cyclic GMP-AMP is an endogenous second messenger in innate immune signaling by cytosolic DNA", Science. Feb. 15, 2013;339(6121):826-30.
Xiao et al. "The cGAS-STING Pathway for DNA Sensing," Mol. Cell, vol. 51, Jul. 25, 2013, pp. 135-139.
Yanai et al. "HMGB proteins function as universal sentinels for nuceic-acid-mediated innate immune responses," Nature, vol. 462, Nov. 5, 2009, pp. 99-103.
Yang et al. "The cytosolic nucleic acid sensor LRRFIP1 mediates the production of type I interferon via a β-catenin-dependent pathway," Nat. Immunol., vol. 11, No. 6, Jun. 2010, pp. 487-494, with 13 pages of Supplementary Materials.
Zhang et al. "The helicase DDX41 senses intracellular DNA mediated by the adaptor STING in dendritic cells," Nat. Immunol., vol. 12, No. 10, 2011, pp. 959-965.
Zhong et al. "The adaptor protein MITA links virus-sensing receptors to IRF3 transcription factor activation," Immunity 29, Oct. 17, 2008, pp. 538-550.
Zhou et al. "MyD88 is critical for the development of innate and adaptive immunity during acute lymphocytic choriomeningitis virus infection," Eur. J. Immunol., vol. 35, 2005, pp. 822-830.
Zhou et al. "MyD88 Intrinsically Regulates CD4 T-Cell Responses," J Virol., vol. 83, No. 4, Feb. 2009, pp. 1625-1634.
Abutaily et al., Cadherins, catenins and APC in pleural malignant mesothelioma. J Pathol. Nov. 2003;201(3):355-362.
Adler-Moore et al., Characterization of the murine Th2 response to immunization with liposomal M2e influenza vaccine. Vaccine. Jun. 15, 2011;29(27):4460-4468.
Aguilar et al., Endemic Venezuelan Equine Encephalitis in Northern Peru. Emerg Infect Dis. May 2004;10(5):880-888.
Ahmed et al., Assessing the Safety of Adjuvanted Vaccines. Sci Transl Med. Jul. 27, 2011;3(93):93rv2.
Ahn et al., All CVB Serotypes and Clinical Isolates Induce Irreversible Cytopathic Effects in Primary Cardiomyocytes. J Med Virol. Feb. 2005;75(2):290-294.
Altwein and Luboldt, Prognostic Factors for Carcinoma of the Prostate. Urol Int. 1999;63(1):62-71.
Alvarez-Lafuente et al., Human parvovirus B19, varicella zoster virus, and human herpes virus 6 in temporal artery biopsy specimens of patients with giant cell arteritis: analysis with quantitative real time polymerase chain reaction. Ann Rheum Dis. 2005.
Andersen and thor Straten, Survivin—a universal tumor antigen. Histol Histopathol. Apr. 2002;17(2):669-675.
Antonarakis and Drake, Combining immunological and androgen-directed approaches: an emerging concept in prostate cancer immunotherapy. Curr Opin Oncol. May 2012;24(3):258-265.
Argani et al., Discovery of New Markers of Cancer through Serial Analysis of Gene Expression Prostate Stem Cell Antigen Is Overexpressed in Pancreatic Adenocarcinoma. Cancer Res. Jun. 1, 2001;61(11):4320-4324.
Arora et al., Identification of Differentially Expressed Genes in Oral Squamous Cell Carcinoma. Mol Carcinog. Feb. 2005;42(2):97-108.
Attoui et al., Comparative sequence analysis of American, European and Asian isolates of viruses in the genus Coltivirus. J Gen Virol. Oct. 1998;79 ( Pt 10):2481-2489.
Ausmees et al., Genetic data indicate that proteins containing the GGDEF domain possess diguanylate cyclase activity. FEMS Microbiol Lett. Oct. 16, 2001;204(1):163-167.
Badovinac et al., Accelerated CD8+ T-cell memory and prime-boost response after dendritic-cell vaccination. Nat Med. Jul. 2005;11(7):748-756.
Bahjat et al., Activation of Immature Hepatic NK Cells As Immunotherapy for Liver Metastatic Disease. J Immunol. Dec. 1, 2007;179(11):7376-7384.
Bahjat et al., Cytosolic Entry Controls CD8+-T-Cell Potency during Bacterial Infection. Infect Immun. Nov. 2006;74(11):6387-6397.
Bahjat et al., Suppression of Cell-Mediated Immunity following Recognition of Phagosome-Confined Bacteria. PLoS Pathog. Sep. 2009;5(9):e1000568.
Bala et al., PLGA Nanoparticles in Drug Delivery: The State of the Art. Crit Rev Ther Drug Carrier Syst. 2004;21(5):387-422.
Baldwin et al., The Importance of Adjuvant Formulation in the Development of a Tuberculosis Vaccine. J Immunol. Mar. 1, 2012;188(5):2189-2197.

(56) References Cited

OTHER PUBLICATIONS

Barbanti-Brodano et al., Simian virus 40 infection in humans and association with human diseases: results and hypotheses. Virology. Jan. 5, 2004;318(1):1-9.
Barber, Cytoplasmic DNA innate immune pathways. Immunol Rev. Sep. 2011;243(1):99-108.
Barber, STING-dependent signaling. Nat Immunol. Sep. 20, 2011;12(10):929-930.
Barthold et al., Infectivity, disease patterns, and serologic profiles of reovirus serotypes 1, 2, and 3 in infant and weanling mice. Lab Anim Sci. Oct. 1993;43(5):425-430.
Battistini et al., Stereoselective Synthesis of Cyclic Dinucleotide Phosphorothioates. Tetrahedron, 1993;49(5):1115-1132.
Baurain et al., High Frequency of Autologous Anti-Melanoma CTL Directed Against an Antigen Generated by a Point Mutation in a New Helicase Gene. J Immunol. Jun. 1, 2000;164(11):6057-6066.
Bevanger et al., Competitive Enzyme Immunoassay for Antibodies to a 43,000—Molecular-Weight Francisella tularensis Outer Membrane Protein for the Diagnosis of Tularemia. J Clin Microbiol. May 1989;27(5):922-926.
Bhigjee et al., Sequence of the env gene of some KwaZulu-Natal, South African strains of HTLV type I. AIDS Res Hum Retroviruses. Sep. 1, 1999;15(13):1229-1233.
Biagini et al., Simultaneous measurement of specific serum IgG responses to five select agents. Anal Bioanal Chem. Jun. 2005;382(4):1027-1034.
Blankenstein et al., The determinants of tumour immunogenicity. Nat Rev Cancer. Mar. 1, 2012;12(4):307-313.
Bondurant et al., Definition of an Immunogenic RegionWithin the Ovarian Tumor Antigen Stratum Corneum Chymotryptic Enzyme. Clin Cancer Res. May 1, 2005;11(9):3446-3454.
Brahmer et al., Phase I Study of Single-Agent Anti-Programmed Death-1 (MDX-1106) in Refractory Solid Tumors: Safety, Clinical Activity, Pharmacodynamics, and Immunologic Correlates. J Clin Oncol. Jul. 1, 2010;28(19):3167-3175.
Brezniceanu et al., HMGB1 inhibits cell death in yeast and mammalian cells and is abundantly expressed in human breast carcinoma. FASEB J. Jul. 2003;17(10):1295-1297.
Brian and Baric, Coronavirus Genome Structure and Replication. Curr Top Microbiol Immunol. 2005;287:1-30.
Brinkmann et al., Novel Genes in the PAGE and GAGE Family of Tumor Antigens Found by Homology Walking in the dbEST Database. Cancer Res. Apr. 1, 1999;59(7):1445-1448.
Brockstedt et al., Killed but metabolically active microbes: a new vaccine paradigm for eliciting effector T-cell responses and protective immunity. Nat Med. Aug. 2005;11(8):853-860.
Brockstedt et al., Listeria-based cancer vaccines that segregate immunogenicity from toxicity. Proc Natl Acad Sci U S A. Sep. 21, 2004;101(38):13832-13837.
Bronte et al., Genetic Vaccination with "Self" Tyrosinase-related Protein 2 Causes Melanoma Eradication but not Vitiligo. Cancer Res. Jan. 15, 2000;60(2):253-258.
Brown et al., Complete Genomic Sequencing Shows that Polioviruses and Members of Human Enterovirus Species C Are Closely Related in the Noncapsid Coding Region. J Virol. Aug. 2003;77(16):8973-8984.
Brown, Variants of B19. Dev Biol (Basel). 2004;118:71-77.
Burger's Medicinal Chemistry and Drug Discovery, Fifth Edition, published 1994 by Wiley-Interscience, edited by Manfred E. Wolff, pp. 975-977.
Capdepont et al., New Insights in HTLV-I Phylogeny by Sequencing and Analyzing the Entire Envelope Gene. AIDS Res Hum Retroviruses. Jan. 2005;21(1):28-42.
Capurro et al., Glypican-3: A Novel Serum and Histochemical Marker for Hepatocellular Carcinoma. Gastroenterology. Jul. 2003;125(1):89-97.
Carbone et al., New developments about the association of SV40 with human mesothelioma. Oncogene. Aug. 11, 2003;22(33):5173-5180.

Chan et al., In Situ Hybridization Study of PSP94 (Prostatic Secretory Protein of 94 Amino Acids) Expression in Human Prostates. Prostate. Oct. 1, 1999;41(2):99-109.
Chang et al., A Phase I Trial of Tumor Lysate-Pulsed Dendritic Cells in the Treatment of Advanced Cancer. Clin Cancer Res. Apr. 2002;8(4):1021-1032.
Chen et al., Immunodominant CD41 responses identified in a patient vaccinated with full-length NY-ESO-1 formulated with ISCOMATRIX adjuvant. Proc Natl Acad Sci USA. Jun. 22, 2004;101(25):9363-9368.
Chen et al., The potential of c-di-GMP as an effective vaccine adjuvant. Vaccine. Apr. 19, 2010;28(18):3080-3085.
Chern et al., Glycoprotein B Subtyping of Cytomegalovirus (CMV) in the Vitreous of Patients with AIDS and CMV Retinitis. J Infect Dis. Oct. 1998;178(4):1149-1153.
Chiari et al., Two Antigens Recognized by Autologous Cytolytic T Lymphocytes on a Melanoma Result from a Single Point Mutation in an Essential Housekeeping Gene. Cancer Res. Nov. 15, 1999;59(22):5785-5792.
Christiansen et al., Polarity of Prostate Specific Membrane Antigen, Prostate Stem Cell Antigen, and Prostate Specific Antigen in Prostate Tissue and in a Cultured Epithelial Cell Line. Prostate. Apr. 1, 2003;55(1):9-19.
Clements et al., Adenomatous Polyposis Coli/β-Catenin Interaction and Downstream Targets: Altered Gene Expression in Gastrointestinal Tumors. Clin Colorectal Cancer. Aug. 2003;3(2):113-120.
Clifton et al., A chlamydial type III translocated protein is tyrosine-phosphorylated at the site of entry and associated with recruitment of actin. Proc Natl Acad Sci USA. Jul. 6, 2004;101(27):10166-10171.
Clinton et al., A Comparative Study of Four Serological Tumor Markers for the Detection of Breast Cancer. Biomed Sci Instrum. 2003;39:408-414.
Cobaleda et al., A primitive hematopoietic cell is the target for the leukemic transformation in human Philadelphia-positive acute lymphoblastic leukemia. Blood. Feb. 1, 2000;95(3):1007-1013.
Codrington et al., Analysis of ETV6/AML1 abnormalities in acute lymphoblastic leukaemia: incidence, alternative spliced forms and minimal residual disease value. Br J Haematol. Dec. 2000;111(4):1071-1079.
Coffman et al., Vaccine adjuvants: putting innate immunity to work. Immunity. Oct. 29, 2010;33(4):492-503.
Coler et al. Development and Characterization of Synthetic Glucopyranosyl Lipid Adjuvant System as a Vaccine Adjuvant. PLoS One. Jan. 26, 2011;6(1):e16333.
Coughlin et al., Orally Bioavailable Anti-HBV Dinucleotide Acyloxyalkyl Prodrugs. Bioorg Med Chem Lett. Mar. 1, 2010;20(5):1783-1786.
Creighton et al., Mechanisms and catalysts of disulfide bond formation in proteins. Trends Biotechnol. Jan. 1995;13(1):18-23.
Crimmins et al., Listeria monocytogenes multidrug resistance transporters activate a cytosolic surveillance pathway of innate immunity. Proc Natl Acad Sci U S A. Jul. 22, 2008;105(29):10191-10196.
Crittenden et al., Expression of Inflammatory Chemokines Combined with Local Tumor Destruction Enhances Tumor Regression and Long-term Immunity. Cancer Res. Sep. 1, 2003;63(17):5505-5512.
Curran and Allison, Tumor Vaccines Expressing Flt3 Ligand Synergize with CTLA-4 Blockade to Reject Preimplanted Tumors. Cancer Res. Oct. 1, 2009;69(19):7747-7755.
Dalby et al., Advanced transfection with Lipofectamine 2000 reagent: primary neurons, siRNA, and high-throughput applications. Methods. Jun. 2004;33(2):95-103.
Dalerba et al., MAGE, BAGE and GAGE gene expression in human rhabdomyosarcomas. Int J Cancer. Jul. 1, 2001;93(1):85-90.
Damasus-Awatai and Freeman-Wang, Human papilloma virus and cervical screening. Curr Opin Obstet Gynecol. Dec. 2003;15(6):473-477.
Das et al., Evaluation of a Western Equine Encephalitis recombinant E1 protein for protective immunity and diagnostics. Antiviral Res. Nov. 2004;64(2):85-92.

(56) References Cited

OTHER PUBLICATIONS

Davies et al., Characterisation of a recombinant Fv fragment of anti-MUC1 antibody HMFG1. Cancer Lett. Jul. 29, 1994;82(2):179-184.
Davies et al., Coordinated Regulation of Accessory Genetic Elements Produces Cyclic Di-Nucleotides for V. cholerae Virulence. Cell. Apr. 13, 2012;149(2):358-370.
De Backer et al., Characterization of the GAGE Genes That Are Expressed in Various Human Cancers and in Normal Testis. Cancer Res. Jul. 1, 1999;59(13):3157-3165.
de Grujil et al., Whole-cell cancer vaccination: from autologous to allogeneic tumor—and dendritic cell-based vaccines. Cancer Immunol Immunother. Oct. 2008;57(10):1569-1577.
de Villiers et al., Classification of papillomaviruses. Virology. Jun. 20, 2004;324(1):17-24.
Demidenko and Blagosklonny, Flavopiridol Induces p53 via Initial Inhibition of Mdm2 and P21 and, Independently of p53, Sensitizes Apoptosis-Reluctant Cells to Tumor Necrosis Factor. Cancer Res. May 15, 2004;64(10):3653-3660.
Desmet and Ishii, Nucleic acid sensing at the interface between innate and adaptive immunity in vaccination. Nat Rev Immunol. Jun. 22, 2012;12(7):479-491.
Dessureault et al., A phase-I Trial Using a Universal GM-CSF-producing and CD40L-expressing Bystander Cell Line (GM.CD40L) in the Formulation of Autologous Tumor Cell-based Vaccines for Cancer Patients with Stage IV disease. Ann Surg Oncol. 2007.
Di Lorenzo et al., Immunotherapy for the treatment of prostate cancer. Nat Rev Clin Oncol. May 24, 2011;8(9):551-561.
Disis and Cheever, HER-2/Neu Protein: A Target for Antigen-Specific Immunotherapy of Human Cancer. Adv Cancer Res. 1997;71:343-371.
Disis et al., Humoral Epitope-Spreading Following Immunization with a HER-2/neu Peptide Based Vaccine in Cancer Patients. J Clin Immunol. Sep. 2004;24(5):571-578.
Dosaka-Akita et al., Expression of N-Acetylglucosaminyltransferase V Is Associated with Prognosis and Histology in Non-Small Cell Lung Cancers. Clin Cancer Res. Mar. 1, 2004;10(5):1773-1779.
Drake et al., Androgen ablation mitigates tolerance to a prostate/prostate cancer-restricted antigen. Cancer Cell. Mar. 2005;7(3):239-249.
Dranoff et al., Vaccination with irradiated tumor cells engineered to secrete murine granulocyte-macrophage colony-stimulating factor stimulates potent, specific, and long-lasting anti-tumor immunity. Proc Natl Acad Sci U S A. Apr. 15, 1993;90(8):3539-3543.
Driessens et al., Highly Successful Therapeutic Vaccinations Combining Factor Dendritic Cells and Tumo Cells Secreting Granulocyte Macrophage Colony-stimulating Factor. Cancer Res. Nov. 15, 2004;64(22):8435-8442.
Dubensky and Reed, Adjuvants for cancer vaccines. Semin Immunol. Jun. 2010;22(3):155-161.
Dubensky et al., Abstract 4573: A novel tumor vaccine with cyclic dinucleotides—can induce potent anti-tumor responses in vivo. Cancer Res. Apr. 15, 2013;73(8 Suppl):4573-4573.
Duxbury et al., CEACAM6 as a novel target for indirect type 1 immunotoxin-based therapy in pancreatic adenocarcinoma. Biochem Biophys Res Commun. May 7, 2004;317(3):837-843.
Eager and Nemunaitis, GM-CSF Gene-Transduced Tumor Vaccines. Mol Ther. Jul. 2005;12(1):18-27.
Ebensen et al., Bis-(3',5')-cyclic dimeric adenosine monophosphate: strong Th1/Th2/Th17 promoting mucosal adjuvant. Vaccine. Jul. 18, 2011;29(32):5210-5220.
Ebensen et al., The Bacterial Second Messenger cdiGMP Exhibits Promising Activity as a Mucosal Adjuvant. Clin Vaccine Immunol. Aug. 2007;14(8):952-958.
Ebensen et al., The Bacterial Second Messenger cdiGMP Exhibits Promising Activity as a Mucosal Adjuvant. Vaccine. Feb. 9, 2007;25(8):1464-1469.

Einstein et al., Comparison of the immunogenicity and safety of Cervarix and Gardasil human papillomavirus (HPV) cervical cancer vaccines in healthy women aged 18-45 years. Hum Vaccin. Oct. 2009;5(10):705-719.
Elgh et al., Serological Diagnosis of Hantavirus Infections by an Enzyme-Linked Immunosorbent Assay Based on Detection of Immunoglobulin G and M Responses to Recombinant Nucleocapsid Proteins of Five Viral Serotypes. J Clin Microbiol. 1997.
Engels et al., Serologic Evidence for Exposure to Simian Virus 40 in North American Zoo Workers. J Infect Dis. Dec. 15, 2004;190(12):2065-2069.
Enjoji et al., RCAS1, a Useful Serum Marker to Predict the Recurrence of Cancer: Two Cases of Cholangiocarcinoma and Pancreatic Cancer. Dig Dis Sci. Oct. 2004;49(10):1654-1656.
Ericson et al., Expression of Cyclin-Dependent Kinase 6, but not Cyclin-Dependent Kinase 4, Alters Morphology of Cultured Mouse Astrocytes. Mol Cancer Res. Jul. 2003;1(9):654-664.
Ertem and Ferris, Synthesis of RNA oligomers on heterogeneous templates. Nature. Jan. 18, 1996;379(6562):238-240.
Estrada-Franco et al., Venezuelan Equine Encephalitis Virus, Southern Mexico. Emerg Infect Dis. Dec. 2004;10(12):2113-2121.
Ettmayer et al., Lessons Learned from Marketed and Investigational Prodrugs. J Med Chem. May 6, 2004;47(10):2393-2404.
Fang et al., Expression of Dnmt1, demethylase, MeCP2 and methylation of tumor-related genes in human gastric cancer. World J Gastroenterol. Dec. 1, 2004;10(23):3394-3398.
Fasso et al., SPAS-1 (stimulator of prostatic adenocarcinoma-specific T cells)/SH3GLB2: A prostate tumor antigen identified by CTLA-4 blockade. Proc Natl Acad Sci U S A. Mar. 4, 2008;105(9):3509-3514.
Faure et al., Inducible Hsp70 as Target of Anticancer Immunotherapy: Identification of HLA-A*0201-Restricted Epitopes. Int J Cancer. Mar. 1, 2004;108(6):863-870.
Fleishhauer et al., The DAM Gene Family Encodes a New Group of Tumor-specific Antigens Recognized by Human Leukocyte Antigen AI-restricted Cytotoxic T Lymphocytes. Cancer Res. Jul. 15, 1998;58(14):2969-2972.
Fong et al., Altered peptide ligand vaccination with Flt3 ligand expanded dendritic cells for tumor immunotherapy. Proc Natl Acad Sci U S A. Jul. 17, 2001;98(15):8809-8814.
Fuessel et al., Multiple tumor marker analyses (PSA, hK2, PSCA, trp-p8) in primary prostate cancers using quantitative RT-PCR. Int J Oncol. Jul. 2003;23(1):221-228.
Fujii et al., The VesiVax system: a method for rapid vaccine development. Front Biosci. Jan. 1, 2008;13:1968.
Gambus et al., Epitope mapping of a mouse monoclonal anti-MUC2 antibody suggests the existence of an immunodominant region in the COOH terminus of the MUC2 tandem-repeat sequence. Int J Cancer. Jan. 3, 1995;60(1):146-148.
Gao et al., GM-CSF-surface-modified B16.F10 melanoma cell vaccine. Vaccine. Jun. 19, 2006;24(25):5265-5268.
Geisbert and Jahrling, Differentiation of filoviruses by electron microscopy. Virus Res. Dec. 1995;39(2-3):129-150.
Ghazizadeh et al., Role of cdk4, p16INK4, and Rb Expression in the Prognosis of Bronchioloalveolar Carcinomas. Respiration. Jan.-Feb. 2005;72(1):68-73.
Gilliam et al., A phase II study of G17DT in gastric carcinoma. Eur J Surg Oncol. Jun. 2004;30(5):536-543.
Goldberg et al., Role of PD-1 and its ligand, B7-H1, in early fate decisions of CD8 T cells. Blood. Jul. 1, 2007;110(1):186-192.
Gonzalez et al., A comparative sequence analysis to revise the current taxonomy of the family Coronaviridae. Arch Virol. Nov. 2003;148(11):2207-2235.
Good et al., Development and regulation of cell-mediated immune responses to the blood stages of malaria: implications for vaccine research. Annu Rev Immunol. 2005;23:69-99.
Good et al., The immunological challenge to developing a vaccine to the blood stages of malaria parasites. Immunol Rev. Oct. 2004;201:254-267.
Grajkowski et al., Convenient Synthesis of a Propargylated Cyclic (3'-5') Diguanylic Acid and its "Click" Conjugation to a Biotinylated Azide. Bioconjug Chem. Nov. 17, 2010;21(11):2147-2152.

(56) References Cited

OTHER PUBLICATIONS

Grimm et al., Mouse alpha-fetoprotein-specific DNA-based immunotherapy of hepatocellular carcinoma leads to tumor regression in mice. Gastroenterology. Oct. 2000;119(4):1104-1112.
Groh et al., Efficient cross-priming of tumor antigen-specific T cells by dendritic cells sensitized with diverse anti-MICA opsonized tumor cells. Proc Natl Acad Sci USA. May 3, 2005;102(18):6461-6466.
Gueguen et al., An Antigen Recognized by Autologous CTLs on a Human Bladder Carcinoma. J Immunol. Jun. 15, 1998;160(12):6188-6194.
Gulley et al., Immunologic and Prognostic Factors Associated with Overall Survival Employing a Poxviral-based PSA Vaccine in Metastatic Castrate-resistant Prostate Cancer. Cancer Immunol Immunother. May 2010;59(5):663-674.
Gulmann et al., Adenomatous Polyposis Coli Gene, beta-Catenin, and E-Cadherin Expression in Proximal and Distal Gastric Cancers and Precursor Lesions. Appl Immunohistochem Mol Morphol. Sep. 2003;11(3):230-237.
Gupta et al., Refolding, purification, and crystallization of apical membrane antigen 1 from Plasmodium falciparum. Protein Expr Purif. May 2005;41(1):186-198.
Haddad et al., Novel antigen identification method for discovery of protective malaria antigens by rapid testing of DNA vaccines encoding exons from the parasite genome. Infect Immun. Mar. 2004;72(3):1594-1602.
Hakansson et al., Establishment and phenotypic characterization of human U937 cells with inducible P210 BCR/ABL expression reveals upregulation of CEACAM1 (CD66a). (2004) Leukemia 18:538-547.
Harris et al., The Biological and Therapeutic Importance of Gastrin Gene Expression in Pancreatic Adenocarcinomas. Cancer Res. Aug. 15, 2004;64(16):5624-5631.
Harty and Badovinac, Shaping and reshaping CD8+ T-cell memory. Nat Rev Immunol. Feb. 2008;8(2):107-19-119.
Hashido et al., Evaluation of an Enzyme-Linked Immunosorbent Assay Based on Binding Inhibition for Type-Specific Quantification of Poliovirus Neutralization-Relevant Antibodies. Microbiol Immunol. 1999;43(1):73-77.
Hassan et al., Mesothelin: A New Target for Immunotherapy. Clin Cancer Res. Jun. 15, 2004;10(12 Pt 1):3937-3942.
Havlasova et al., Mapping of immunoreactive antigens of Francisella tularensis live vaccine strain. Proteomics. Jul. 2002;2(7):857-867.
Havlasova et al., Proteomic analysis of anti-Francisella tularensis LVS antibody response in murine model of tularemia. Proteomics. May 2005;5(8):2090-2103.
Hayakawa, A facile synthesis of cyclic bis(3′0!5′0)diguanylic acid. Tetrahedron 2003;59:6465-6471.
He et al., Complexes of Poliovirus Serotypes with Their Common Cellular Receptor, CD155. J Virol. Apr. 2003;77(8):4827-4835.
Hernandez et al., Novel Kidney Cancer Immunotherapy Based on the Granulocyte-Macrophage Colony-stimulating Factor and Carbonic Anhydrase IX Fusion Gene. Clin Cancer Res. May 2003;9(5):1906-1916.
Hirose et al., Incidence of Diffuse Large B-Cell Lymphoma of Germinal Center B-Cell Origin in Whole Diffuse Large B-Cell Lymphoma: Tissue Fluorescence In Situ Hybridization Using t(14;18) Compared with Immunohistochemistry. Int J Hematol. 2005.
Hodi et al., Improved Survival with Ipilimumab in Patients with Metastatic Melanoma. N Engl J Med. Aug. 19, 2010;363(8):711-723.
Hoffman et al., Strategy for development of a pre-erythrocytic Plasmodium falciparum DNA vaccine for human use. Vaccine. Jun. 1997;15(8):842-845.
Hoke, History of U.S. Military Contributions to the Study of Viral Encephalitis. Mil Med. Apr. 2005;170(4 Suppl):92-105.
Hu et al., c-di-GMP as a vaccine adjuvant enhances protection against systemic methicillin-resistant *Staphylococcus aureus* (MRSA) infection. Vaccine. Jul. 30, 2009;27(35):4867-4873.
Hughes, Nanostructure-mediated drug delivery. Nanomedicine. Mar. 2005;1(1):22-30.
Hurwitz et al., The TRAMP Mouse as a Model for Prostate Cancer. Curr Protoc Immunol. Nov. 2001;Chapter 20:Unit 20.5.
Hussain and Paterson, What is needed for effective antitumor immunotherapy? Lessons learned using Listeria monocytogenes as a live vector for HPV-associated tumors. Cancer Immunol Immunother. Jun. 2005;54(6):577-586.
Hutchinson et al., Multiplex Analysis of Cytokines in the Blood of Cynomolgus Macaques Naturally Infected With Ebola Virus (Reston Serotype). J Med Virol. Nov. 2001;65(3):561-566.
Hyodo et al., Synthesis of cyclic bis(3′-5′)diguanylic acid (c-di-GMP) analogs. Tetrahedron 2006;62:3089-3094.
Iacobuzio-Donahue et al., Highly Expressed Genes in Pancreatic Ductal Adenocarcinomas: A Comprehensive Characterization and Comparison of the Transcription Profiles Obtained from Three Major Technologies. Cancer Res. Dec. 2003.
Iqbal et al., BCL2 Translocation Defines a Unique Tumor Subset within the Germinal Center B-Cell-Like Diffuse Large B-Cell Lymphoma. Am J Pathol. Jul. 2004;165(1):159-166.
Isherwood et al., Vaccination strategies for Francisella tularensis. Adv Drug Deliv Rev. Jun. 17, 2005;57(9):1403-1414.
Ishikawa and Barber, STING an Endoplasmic Reticulum Adaptor that Facilitates Innate Immune Signaling. Nature. Oct. 2, 2008;455(7213):674-678.
Ishikawa and Barber, The STING pathway and regulation of innate immune signaling in response to DNA pathogens. Cell Mol Life Sci. Apr. 2011;68(7):1157-1165.
Ito et al., Prostate Carcinoma Detection and Increased Prostate-Specific Antigen Levels after 4 Years in Dutch and Japanese Males Who Had No Evidence of Disease at Initial Screening. Cancer. Jan. 15, 2005;103(2):242-250.
Iwasaki and Medzhitov, Regulation of adaptive immunity by the innate immune system. Science. Jan. 15, 2010;327(5963):291-295.
Jainkittivong and Langlais, Herpes B virus infection. Oral Surg Oral Med Oral Pathol Oral Radiol Endod. Apr. 1998;85(4):399-403.
Jamieson et al., Human Torovirus: A New Nosocomial Gastrointestinal Pathogen. J Infect Dis. Nov. 1998;178(5):1263-1269.
Jansen and Shaw, Human Papillomavirus Vaccines and Prevention of Cervical Cancer. Annu Rev Med. 2004;55:319-331.
Jemal et al., Cancer statistics, 2010. CA Cancer J Clin. Sep.-Oct. 2010;60(5):277-300.
Jin et al., Identification and characterization of a loss-of-function human MPYS variant. Genes Immun. Jun. 2011;12(4):263-269.
Jung et al., Strategies Against Human Papillomavirus Infection and Cervical Cancer. J Microbiol. Dec. 2004;42(4):255-266.
Jungck et al., E-cadherin expression is homogeneously reduced in adenoma from patients with familial adenomatous polyposis: an immunohistochemical study of E-cadherin, beta-catenin and cyclooxygenase-2 expression. Int J Colorectal Dis. 2004.
Kantoff et al., Overall Survival Analysis of a Phase II Randomized Controlled Trial of a Poxviral-Based PSA-Targeted Immunotherapy in Metastatic Castration-Resistant Prostate Cancer. J Clin Oncol. Mar. 1, 2010;28(7):1099-1105.
Kantoff et al., Sipuleucel-T Immunotherapy for Castration-Resistant Prostate Cancer. N Engl J Med. Jul. 29, 2010;363(5):411-422.
Karaolis et al., Bacterial c-di-GMP Is an Immunostimulatory Molecule. J Immunol. Feb. 15, 2007;178(4):2171-2181.
Karaolis et al., Cyclic Di-GMP Stimulates Protective Innate Immunity in Bacterial Pneumonia. Infect Immun. Oct. 2007;75(10):4942-4950.
Kastenmuller et al., Protective T cell immunity in mice following protein-TLR7/8 agonist-conjugate immunization requires aggregation, type I IFN, and multiple DC subsets. J Clin Invest. May 2011;121(5):1782-1796.
Kasturi et al. Programming the magnitude and persistence of antibody responses with innate immunity. Nature 2011;470:543-7.
Kaufman et al., Parvovirus B19 does not bind to membrane-associated globoside in vitro. Virology. Feb. 5, 2005;332(1):189-198.
Kawai and Akira, The role of pattern-recognition receptors in innate immunity: update on Toll-like receptors. Nat Immunol. May 2010;11(5):373-384.

(56) References Cited

OTHER PUBLICATIONS

Kedl et al., Comparative Sequence Analysis of the Reovirus S4 Genes from 13 Serotype 1 and Serotype 3 Field Isolates. J Virol. Jan. 1995;69(1):552-559.
Kim et al., Comparison of HPV DNA vaccines employing intracellular targeting strategies. Gene Ther. Jun. 2004;11(12):1011-1018.
Krishnamachari et al., Nanoparticle Delivery Systems in Cancer Vaccines. Pharm Res 2011;28:215-236.
Krzych et al., T lymphocytes from volunteers immunized with irradiated Plasmodium falciparum sporozoites recognize liver and blood stage malaria antigens. J Immunol. Oct. 15, 1995;155(8):4072-4077.
Kubuschok et al., Expression of cancer testis antigens in pancreatic carcinoma cell lines, pancreatic adenocarcinoma and chronic pancreatitis. Int J Cancer. Apr. 20, 2004;109(4):568-575.
Kumamuru et al., T-cell receptor Vbeta gene usage by T cells reactive with the tumor-rejection antigen SART-1 in oral squamous cell carcinoma. Int J Cancer. Feb. 20, 2004;108(5):686-695.
Laheru and Jaffee, Immunotherapy for pancreatic cancer—science driving clinical progress. Nat Rev Cancer. Jun. 2005;5(6):459-467.
Lauvau et al., Priming of Memory But Not Effector CD8 T Cells by a Killed Bacterial Vaccine. Science. Nov. 23, 2001;294(5547):1735-1739.
Le et al., A Live-Attenuated Listeria Vaccine (ANZ-100) and a Live-Attenuated Listeria Vaccine Expressing Mesothelin (CRS-207) for Advanced Cancers: Phase I Studies of Safety and Immune Induction. Clin Cancer Res. Feb. 1, 2012;18(3):858-868.
Leber et al., Distinct TLR- and NLR-Mediated Transcriptional Responses to an Intracellular Pathogen. PLoS Pathog. Jan. 2008;4(1):e6.
Lee et al., A clinical grade cocktail of cytokines and $PGE_2$ results in uniform maturation of human monocyte-derived dendritic cells: implications for immunotherapy. Vaccine. Dec. 19, 2002;20 Suppl 4:A8-A22.
Lee et al., Immunomic analysis of human sarcoma. Proc Natl Acad Sci U S A. Mar. 4, 2003;100(5):2651-2656.
Li et al., Advanced Glycation End Products Induce Tubular Epithelial-Myofibroblast Transition through the RAGE-ERK1/2 MAP Kinase Signaling Pathway. Am J Pathol. Apr. 2004;164(4):1389-1397.
Li et al., Expression Profile of Cancer-Testis Genes in 121 Human Colorectal Cancer Tissue and Adjacent Normal Tissue. Clin Cancer Res. Mar. 1, 2005;11(5):1809-1814.
Liang et al., Microvessel density, cyclo-oxygenase 2 expression, K-ras mutation and p53 overexpression in colonic cancer. Br J Surg. Mar. 2004;91(3):355-361.
Libanova et al., The member of the cyclic di-nucleotide family bis-(3', 5')-cyclic dimeric inosine monophosphate exerts potent activity as mucosal adjuvant. Vaccine. Mar. 2, 2010;28(10):2249-2258.
Lim et al., Molecular and phenotypic spectrum of de novo Philadelphia positive acute leukemia. Int J Mol Med. Dec. 1999;4(6):665-667.
Lin et al., Melanoma-Associated Antigens in Esophageal Adenocarcinoma Identification of Novel MAGE-A10 Splice Variants. Clin Cancer Res. Sep. 1, 2004;10(17):5708-5716.
Lubong Sabado et al., In Vitro Priming Recapitulates In Vivo HIV-1 Specific T Cell Responses, Revealing Rapid Loss of Virus Reactive CD4+ T Cells in Acute HIV-1 Infection. PLoS One. 2009;4(1):e4256 (13 pages).
Lucas et al., MAGE-B5, MAGE-B6, MAGE-C2, and MAGE-C3: four new members of the MAGE family with tumor-specific expression. Int J Cancer. Jul. 1, 2000;87(1):55-60.
Luo et al., Selective binding of 2'-F-c-di-GMP to Ct-E88 and Cb-E43, new class I riboswitches from *Clostridium tetani* and *Clostridium botulinum* respectively. Molecular Biosystems 2013, 9(6):1535-9; Epub Apr. 5, 2013.
Lutz et al., A Lethally Irradiated Allogeneic Granulocyte-Macrophage Colony Stimulating Factor-Secreting Tumor Vaccine for Pancreatic Adenocarcinoma: A Phase II Trial of Safety, Efficacy, and Immune Activation. Ann Surg. Feb. 2011;253(2):328-335.
Machlenkin et al., Human CTL Epitopes Prostatic Acid Phosphatase-3 and Six-Transmembrane Epithelial Antigen of Prostate-3 as Candidates for Prostate Cancer Immunotherapy. Cancer Res. Jul. 15, 2005;65(14):6435-6442.
Madhun et al., Intranasal c-di-GMP-adjuvanted plant-derived H5 influenza vaccine induces multifunctional Th1 CD4+ cells and strong mucosal and systemic antibody responses in mice. Vaccine. Jul. 12, 2011;29(31):4973-4982.
Mandruzzato et al., A CASP-8 Mutation Recognized by Cytolytic T Lymphocytes on a Human Head and Neck Carcinoma. J Exp Med. Aug. 29, 1997;186(5):785-793.
Matsumoto et al., Expression of the SART-1 antigens in uterine cancers. Jpn J Cancer Res. Dec. 1998;89(12):1292-1295.
Matsushita et al., Preferentially Expressed Antigen of Melanoma (PRAME) in the Development of Diagnostic and Therapeutic Methods for Hematological Malignancies. Leuk Lymphoma. Mar. 2003;44(3):439-444.
Mayo et al., Mdm-2 Phosphorylation by DNA-dependent Protein Kinase Prevents Interaction with p53. Cancer Res. Nov. 15, 1997;57(22):5013-5016.
McCool et al., Roles of calreticulin and calnexin during mucin synthesis in LS180 and HT29/A1 human colonic adenocarcinoma cells. Biochem J. Aug. 1, 1999;341 ( Pt 3):593-600.
McCune et al., Active specific immunotherapy with tumor cells and Corynebacterium parvum: A phase I study. Cancer. May 1979;43(5):1619-1623.
McWhirter et al., A host type I interferon response is induced by cytosolic sensing of the bacterial second messenger cyclic-di-GMP. J Exp Med. Aug. 31, 2009;206(9):1899-1911.
Mellman et al., Cancer immunotherapy comes of age. Nature. Dec. 21, 2011;480(7378):480-489.
Millon et al., Detection of Prostate-Specific Antigen- or Prostate-Specific Membrane Antigen-Positive Circulating Cells in Prostatic Cancer Patients: Clinical Implications. Eur Urol. Oct. 1999;36(4):278-285.
Molijn et al., Molecular diagnosis of human papillomavirus (HPV) infections. J Clin Virol. Mar. 2005;32 Suppl 1:S43-51.
Moreau-Aubry et al., A Processed Pseudogene Codes for a New Antigen Recognized by a Cd8+ T Cell Clone on Melanoma. J Exp Med. May 1, 2000;191(9):1617-1624.
Morse et al., A Phase I Study of Active Immunotherapy with Carcinoembryonic Antigen Peptide (CAP-1)-pulsed, Autologous Human Cultured Dendritic Cells in Patients with Metastatic Malignancies Expressing Carcinoembryonic Antigen. Clin Cancer Res. 1999.
Muderhwa et al., Oil-in-water liposomal emulsions: Characterization and potential use in vaccine delivery. J Pharm Sci. Dec. 1999;88(12):1332-1339.
Mukhopadhyay et al., A structural perspective of the flavivirus life cycle. Nat Rev Microbiol. Jan. 2005;3(1):13-22.
Mulders et al., Tumor antigens and markers in renal cell carcinoma. Urol Clin North Am. Aug. 2003;30(3):455-465.
Muller et al., MeCP2 and MBD2 expression in human neoplastic and non-neoplastic breast tissue and its association with oestrogen receptor status. Br J Cancer. Nov. 17, 2003;89(10):1934-1939.
Muminova et al., Characterization of human mesothelin transcripts in ovarian and pancreatic cancer. BMC Cancer. May 12, 2004;4:19.
Nair et al., Induction of cytotoxic T cell responses and tumor immunity against unrelated tumors using telomerase reverse transcriptase RNA transfected dendritic cells. Nat Med. Sep. 2000;6(9):1011-1017.
Nakatsura et al., Cellular and humoral immune responses to a human pancreatic cancer antigen, coactosin-like protein, originally defined by the SEREX method. Eur J Immunol. Mar. 2002;32(3):826-836.
Nakatsura et al., Glypican-3, overexpressed specifically in human hepatocellular carcinoma, is a novel tumor marker. Biochem Biophys Res Commun. Jun. 20, 2003;306(1):16-25.
Nakatsura et al., Identification of Glypican-3 as a Novel Tumor Marker for Melanoma. Clin Cancer Res. Oct. 1, 2004;10(19):6612-6621.

(56) References Cited

OTHER PUBLICATIONS

Nelson and Griswold, A computer program for calculating antibody affinity constants. Comput Methods Programs Biomed. Jul.-Aug. 1988;27(1):65-68.
Neumann et al., Identification of an HLA-DR-restricted peptide epitope with a promiscuous binding pattern derived from the cancer testis antigen HOM-MEL-40/SSX2. Int J Cancer. Nov. 20, 2004;112(4):661-668.
Nicoletto et al., BRCA-1 and BRCA-2 mutations as prognostic factors in clinical practice and genetic counselling. Cancer Treat Rev. Oct. 2001;27(5):295-304.
Oberste et al., Evidence for Frequent Recombination within Species Human Enterovirus B Based on Complete Genomic Sequences of All Thirty-Seven Serotypes. J Virol. Jan. 2004;78(2):855-867.
Oberthuer et al., The Tumor-Associated Antigen PRAME Is Universally Expressed in High-Stage Neuroblastoma and Associated with Poor Outcome. Clin Cancer Res. Jul. 1, 2004;10(13):4307-4313.
Ogunniyi et al., c-di-GMP is an Effective Immunomodulator and Vaccine Adjuvant Against Pneumococcal Infection. Vaccine. Aug. 26, 2008;26(36):4676-4685.
Oliveira-Ferreira and Daniel-Ribeiro, Protective CD8+ T Cell Responses against the Pre-erythrocytic Stages of Malaria Parasites: an Overview. Mem Inst Oswaldo Cruz. Feb. 2001;96(2):221-227.
Olson et al., Liposomal gD Ectodomain (gD1-306) Vaccine Protects Against HSV2 Genital or Rectal Infection of Female and Male Mice. Vaccine. Dec. 11, 2009;28(2):548-560.
Ora et al., Hydrolytic reactions of cyclic bis(3'-5')diadenylic acid (c-di-AMP). J Physical Organic Chem. 2013; 26(3):218-225.
O'Riordan et al., Innate recognition of bacteria by a macrophage cytosolic surveillance pathway. Proc Natl Acad Sci U S A. Oct. 15, 2002;99(21):13861-13866.
Orvell et al., Antigenic relationships between six genotypes of the small hydrophobic protein gene of mumps virus. J Gen Virol. Oct. 2002;83(Pt 10):2489-2496.
Otte et al., MAGE-A Gene Expression Pattern in Primary Breast Cancer. Cancer Res. Sep. 15, 2001;61(18):6682-6687.
Ouyang et al., Structural Analysis of the STING Adaptor Protein Reveals a Hydrophobic Dimer Interface and Mode of Cyclic di-GMP Binding. Immunity. Jun. 29, 2012;36(6):1073-1086.
Oyston and Quarry, Tularemia vaccine: past, present and future. Antonie Van Leeuwenhoek. May 2005;87(4):277-281.
Padilla et al., Imaging of the varicella zoster virion in the viral highways: Comparison with herpes simplex viruses 1 and 2, cytomegalovirus, pseudorabies virus, and human herpes viruses 6 and 7. J Med Virol. 2003;70 Suppl 1:S103-S110.
Pardoll and Drake, Immunotherapy earns its spot in the ranks of cancer therapy. J Exp Med. Feb. 13, 2012;209(2):201-209.
Pardoll, The blockade of immune checkpoints in cancer immunotherapy. Nat Rev Cancer. Mar. 22, 2012;12(4):252-264.
Patel et al., Development of a simple restriction fragment length polymorphism assay for subtyping of coxsackie B viruses. J Virol Methods. Sep. 15, 2004;120(2):167-172.
Peh et al., Frequent presence of subtype A virus in Epstein-Barr virus-associated malignancies. Pathology. Oct. 2002;34(5):446-450.
Pham, N. L. et al. Exploiting cross-priming to generate protective CD8 T-cell immunity rapidly. Proc Natl Acad Sci U S A. Jul. 6, 2010;107(27):12198-12203.
Pisarev et al., Full-length dominant-negative survivin for cancer immunotherapy. Clin Cancer Res. Dec. 15, 2003;9(17):6523-6533.
Porsch-Ozcurumez et al., Comparison of Enzyme-Linked Immunosorbent Assay, Western Blotting, Microagglutination, Indirect Immunofluorescence Assay, and Flow Cytometry for Serological Diagnosis of Tularemia. Clin Diagn Lab Immunol. 2004.
Prantner et al., 5,6-Dimethylxanthenone-4-acetic Acid (DMXAA) Activates Stimulator of Interferon Gene (STING)-dependent Innate Immune Pathways and Is Regulated by Mitochondrial Membrane Potential. J Biol Chem. Nov. 16, 2012;287(47):39776-39788.

Rappuoli et al., Vaccines for the twenty-first century society. Nat Rev Immunol. Nov. 4, 2011;11(12):865-872.
Reed et al., New horizons in adjuvants for vaccine development. Trends Immunol. Jan. 2009;30(1):23-32.
Renkvist et al., a listing of human tumor antigens recognized by T cells. Cancer Immunol Immunother. Mar. 2001;50(1):3-15.
Reynolds et al., HLA-Independent Heterogeneity of CD8+ T Cell Responses to MAGE-3, Melan-A/MART-1, gp100, Tyrosinase, MC1R, and TRP-2 in Vaccine-Treated Melanoma Patients. J Immunol. Dec. 15, 1998;161(12):6970-6976.
Rezig et al., Molecular Characterization of Coxsackievirus B5 Isolates. J Med Virol. Feb. 2004;72(2):268-274.
Ries et al., Investigation of the expression of melanoma antigen-encoding genes (MAGE-A1 to -A6) in oral squamous cell carcinomas to determine potential targets for gene-based cancer immunotherapy. Int J Oncol. Mar. 2005;26(3):817-824.
Roden and Wu, Preventative and therapeutic vaccines for cervical cancer. Expert Rev Vaccines. Aug. 2003;2(4):495-516.
Roner et al., Identification of signals required for the insertion of heterologous genome segments into the reovirus genome. Proc Natl Acad Sci U S A. Dec. 19, 1995;92(26):12362-12366.
Ross et al., The Cyclic Diguanylic Acid Regulatory System of Cellulose Synthesis in Acetobacter xylinum. Chemical synthesis and biological activity of cyclic nucleotide dimer, trimer, and phosphothioate derivatives. J Biol Chem. Nov. 5, 1990;265(31):18933-18943.
Salazar-Onfray et al., Synthetic peptides derived from the melanocyte-stimulating hormone receptor MC1R can stimulate HLA-A2-restricted cytotoxic T lymphocytes that recognize naturally processed peptides on human melanoma cells. Cancer Res. Oct. 1997.
Santin et al., the serine protease stratum corneum chymotryptic enzyme (kallikrein 7) is highly overexpressed in squamous cervical cancer cells. Gynecol Oncol. Aug. 2004;94(2):283-288.
Sarcevic et al., Expression of Cancer/Testis Tumor Associated Antigens in Cervical Squamous Cell Carcinoma. Oncology. 2003;64(4):443-449.
Sarobe et al., Carcinoembryonic Antigen as a Target to Induce Anti-Tumor Immune Responses. Curr Cancer Drug Targets. Aug. 2004;4(5):443-454.
Sasaki et al., Sage mRNA expression in advanced-stage lung cancers. Eur J Surg Oncol. Dec. 2003;29(10):900-903.
Sasatomi et al., Expression of tumor rejection antigens in colorectal carcinomas. Cancer. Mar. 15, 2002;94(6):1636-1641.
Sawai et al., Preparation and Properties of Oligocytidylates with 2'-5' Internucleotide Linkage. Bull Chem Soc Jpn 1985;58(1):361-366.
Sawai et al., Synthesis of 2'-5' Linked Oligouridylates in Aqueous Medium Using the Pd$^{2+}$ Ion. Chem Pharm Bull. 1981;29(8):2237-2245.
Scanlan et al., Antigens recognized by autologous antibody in patients with renal-cell carcinoma. Int J Cancer. Nov. 12, 1999;83(4):456-464.
Scanlan et al., Cancer-related serological recognition of human colon cancer: identification of potential diagnostic and immunotherapeutic targets. Cancer Res. Jul. 15, 2002;62(14):4041-4047.
Scanlan et al., Expression of cancer-testis antigens in lung cancer: definition of bromodomain testis-specific gene (BRDT) as a new CT gene, CT9. Cancer Lett. Mar. 31, 2000;150(2):155-164.
Scanlan et al., Humoral immunity to human breast cancer: antigen definition and quantitative analysis of mRNA expression. Cancer Immun. Mar. 30, 2001;1:4.
Scanlan et al., The cancer/testis genes: review, standardization, and commentary. Cancer Immun. Jan. 23, 2004;4:1.
Scarcella et al., Expression of MAGE and GAGE in high-grade brain tumors: a potential target for specific immunotherapy and diagnostic markers. Clin Cancer Res. Feb. 1999;5(2):335-341.
Schmidt et al., Memory CD8 T cell responses exceeding a large but definable threshold provide long-term immunity to malaria. Proc Natl Acad Sci U S A. Sep. 16, 2008;105(37):14017-14022.
Schmittgen et al., Expression of prostate specific membrane antigen and three alternatively spliced variants of PSMA in prostate cancer patients. Int J Cancer. Nov. 1, 2003;107(2):323-329.

(56) References Cited

OTHER PUBLICATIONS

Schwartz et al., Hyperinduction of Host Beta Interferon by a Listeria monocytogenes Strain Naturally Overexpressing the Multidrug Efflux Pump MdrT. Infect Immun. Apr. 2012;80(4):1537-1545.

Schwartz et al., Novel targeted and immunotherapeutic strategies in chronic myeloid leukemia. Semin Hematol. Jan. 2003;40(1):87-96.

Seder et al., T-cell quality in memory and protection: implications for vaccine design. Nat Rev Immunol. Apr. 2008;8(4):247-258.

Sepehr et al., Distinct pattern of TP53 mutations in squamous cell carcinoma of the esophagus in Iran. Oncogene. Nov. 1, 2001;20(50):7368-7374.

Shanahan et al., Differential analog binding by two classes of c-di-GMP riboswitches. J Am Chem Soc. Oct. 5, 2011;133(39):15578-15592.

Shanahan et al., Identification of c-di-GMP Derivatives Resistant to an EAL Domain Phosphodiesterase. Biochemistry. Jan. 15, 2013;52(2):365-377.

Shigemasa et al., Expression of the protease inhibitor antileukoprotease and the serine protease stratum corneum chymotryptic enzyme (SCCE) is coordinated in ovarian tumors. Int J Gynecol Cancer. Nov.-Dec. 2001;11(6):454-461.

Shirakawa et al., A Cox-2 Promoter-Based Replication-Selective Adenoviral Vector to Target the Cox-2-Expressing Human Bladder Cancer Cells. Clin Cancer Res. Jul. 1, 2004;10(13):4342-4348.

Shirasawa et al., Receptor for advanced glycation end-products is a marker of type I lung alveolar cells. Genes Cells. Feb. 2004;9(2):165-174.

Shivapurkar et al., Presence of Simian Virus 40 DNA Sequences in Human Lymphoid and Hematopoietic Malignancies and Their Relationship to Aberrant Promoter Methylation of Multiple Genes. Cancer Res. Jun. 1, 2004;64(11):3757-3760.

Siegel et al., Induction of antitumour immunity using survivin peptide-pulsed dendritic cells in a murine lymphoma model. Br J Haematol. Sep. 2003;122(6):911-914.

Silverman, The Organic Chemistry of Drug Design and Drug Action, Published 1992 by Academic Press, pp. 352-397.

Simon et al., Cervical response to vaccination against HPV16 E7 in case of severe dysplasia. Eur J Obstet Gynecol Reprod Biol. Aug. 15, 2003;109(2):219-223.

Singh et al., Avian influenza viral nucleocapsid and hemagglutinin proteins induce chicken CD8+ memory T lymphocytes. Virology 2010;399:231-238.

Singh et al., Non-replicating adenovirus vectors expressing avian influenza virus hemagglutinin and nucleocapsid proteins induce chicken specific effector, memory and effector memory CD8(+) T lymphocytes. Virology. Sep. 15, 2010;405(1):62-69.

Sjolander et al., Serological divergence of Dobrava and Saaremaa hantaviruses: evidence for two distinct serotypes. Epidemiol Infect. Feb. 2002;128(1):99-103.

Skoberne et al., KBMA Listeria monocytogenes is an effective vector for DC-mediated induction of antitumor immunity. J Clin Invest. Dec. 2008;118(12):3990-4001.

Slager et al., Identification of multiple HLA-DR-restricted epitopes of the tumor- associated antigen CAMEL by CD4+ Th1/Th2 lymphocytes. J Immunol. Apr. 15, 2004;172(8):5095-5102.

Slager et al., Induction of CAMEL/NY-ESO-ORF2-specific CD8+ T cells upon stimulation with dendritic cells infected with a modified Ad5 vector expressing a chimeric Ad5/35 fiber. Cancer Gene Ther. Mar. 2004;11(3):227-236.

Small et al., Immunotherapy of Hormone-Refractory Prostate Cancer With Antigen-Loaded Dendritic Cells. J Clin Oncol. Dec. 1, 2000;18(23):3894-3903.

Smith et al., Neutralization of HIV-1 Subtypes: Implications for Vaccine Formulations. J Med Virol. Nov. 1998;56(3):264-268.

Smits et al., Phylogenetic and Evolutionary Relationships among Torovirus Field Variants: Evidence for Multiple Intertypic Recombination Events. J Virol. Sep. 2003;77(17):9567-9577.

Sofia et al., Nucleoside, Nucleotide, and Non-Nucleoside Inhibitors of Hepatitis C Virus NS5B RNA—Dependent RNA—Polymerase. J Med Chem. Mar. 22, 2012;55(6):2481-2531.

Sofia, Nucleotide Prodrugs for HCV Therapy. Antivir Chem Chemother. Aug. 23, 2011;22(1):23-49.

Stams et al., Expression Levels of TEL, AML1, and the Fusion Products TEL-AML1 and AML1-TEL versus Drug Sensitivity and Clinical Outcome in t(12;21)-Positive Pediatric Acute Lymphoblastic Leukemia. Clin Cancer Res. Apr. 15, 2005;11(8):2974-2980.

Steffens et al., Immunohistochemical analysis of tumor antigen saturation following injection of monoclonal antibody G250. Anticancer Res. Mar.-Apr. 1999;19(2A):1197-1200.

Stella, Prodrugs and Therapeutics. Expert Opinion on Therapeutic Patents 2004;14(3):277-280.

Stirnadel et al., Assessment of different sources of variation in the antibody responses to specific malaria antigens in children in Papua New Guinea. Int J Epidemiol. Jun. 2000;29(3):579-586.

Stolier et al., Initial experience with surgical treatment planning in the newly diagnosed breast cancer patient at high risk for BRCA-1 or BRCA-2 mutation. Breast J. Nov.-Dec. 2004;10(6):475-480.

Studahl et al., Herpesvirus DNA Detection in Cerebral Spinal Fluid: Differences in Clinical Presentation between Alpha-, Beta-, and Gamma-Herpesviruses. Scand J Infect Dis. 2000;32(3):237-248.

Sun and Bevan, Defective CD8 T Cell Memory Following Acute Infection Without CD4 T Cell Help. Science. Apr. 11, 2003;300(5617):339-342.

Suzuki et al., Identification of Natural Antigenic Peptides of a Human Gastric Signet Ring Cell Carcinoma Recognized by HLA-A31-Restricted Cytotoxic T Lymphocytes. J Immunol. Sep. 1, 1999;163(5):2783-2791.

Suzuki et al., Practical Synthesis of Cyclic Bis(3'-5')diadenylic Acid (c-di-AMP). Chem Lett. 2011;40(10):1113-1114.

Takahashi et al., 707-AP Peptide Recognized by Human Antibody Induces Human Leukocyte Antigen A2-Restricted Cytotoxic T Lymphocyte Killing of Melanoma. Clin Cancer Res. Aug. 1997;3(8):1363-1370.

Tamayo et al., Roles of Cyclic Diguanylate in the Regulation of Bacterial Pathogenesis. Annu Rev Microbiol. 2007;61:131-148.

Tamura et al., Identification of Cyclophilin B-derived Peptides Capable of Inducing Histocompatibility Leukocyte Antigen-A2-restricted and Tumor-specific Cytotoxic T Lymphocytes. Jpn J Cancer Res. Jul. 2001;92(7):762-767.

Tanaka and Chen, STING Specifies IRF3 Phosphorylation by TBK1 in the Cytosolic DNA Signaling Pathway. Sci Signal. Mar. 6, 2012;5(214):ra20.

Tanaka et al., Expression of Tumor-Rejection Antigens in Gynecologic Cancers. Jpn J Cancer Res. Nov. 2000;91(11):1177-1184.

Tannapfel et al., BRAF Gene Mutations Are Rare Events in Gastroenteropancreatic Neuroendocrine Tumors. Am J Clin Pathol. Feb. 2005;123(2):256-260I.

Tannock et al., Docetaxel plus Prednisone or Mitoxantrone plus Prednisone for Advanced Prostate Cancer. N Engl J Med. Oct. 7, 2004;351(15):1502-1512.

Testa et al., Prodrug Research: futile or fertile? Biochem Pharmacol. Dec. 1, 2004;68(11):2097-2106.

Tewari et al., Poly(I:C) is an effective adjuvant for antibody and multi-functional CD4+ T cell responses to Plasmodium falciparum circumsporozoite protein (CSP) and αDEC-CSP in Non Human Primates. Vaccine. Oct. 21, 2010;28(45):7256-7266.

Tezuka et al., Synthesis of 2'-Modified Cyclic Bis(3'-5')diadenylic Acids (c-di-AMPs) and Their Promotion of Cell Division in a Freshwater Green Alga. Chem Lett. 41: 1723-25, 2012 (doi:10.1246/cl.2012.1723).

Tijono et al., Identification of human-selective analogues of the vascular-disrupting agent 5,6-dimethylxanthenone-4-acetic acid (DMXAA). Br J Cancer. Apr. 2, 2013;108(6):1306-1315.

Topalian et al., Cancer Immunotherapy Comes of Age. J Clin Oncol, Dec. 20, 2011, vol. 29, No. 36, pp. 4828-4836.

Treurnicht et al., HHV-8 subtypes in South Africa: identification of a case suggesting a novel B variant. J Med Virol. Feb. 2002;66(2):235-240.

Trimble et al., Comparison of the CD8+ T cell responses and antitumor effects generated by DNA vaccine administered through gene gun, biojector, and syringe. Vaccine. Sep. 8, 2003;21(25-26):4036-4042.

(56) References Cited

OTHER PUBLICATIONS

Trincado et al., Human Cytomegalovirus Strains Associated With Congenital and Perinatal Infections. J Med Virol. Aug. 2000;61(4):481-487.
Tsang et al., Phenotypic Stability of a Cytotoxic T-Cell Line Directed Against an Immunodominant Epitope of Human Carcinoembryonic Antigen. Clin Cancer Res. Dec. 1997;3(12 Pt 1):2439-2449.
Tsao and Sober, Melanoma Treatment Update. Dermatol Clin. Apr. 2005;23(2):323-333.
Tsuruma et al., Phase I clinical study of anti-apoptosis protein, survivin-derived peptide vaccine therapy for patients with advanced or recurrent colorectal cancer. J Transl Med. Jun. 13, 2004;2(1):19 (11 pages).
Urata et al., Regio- and Diastereo-Selectivity of Montmorillonite-Catalyzed Oligomerization of Racemic Adenosine 5'-Phosphorimidazolide. Nucleosides Nucleotides Nucleic Acids. Apr. 2008;27(4):421-430.
Vallejo et al., Nucleotide Sequence and Restriction Fragment-Length Polymorphism Analysis of Human T-Cell Lymphotropic Virus Type II (HTLV-II) in Southern Europe: Evidence for the HTLV-IIa and HTLV-IIb Subtypes. J Acquir Immune Defic Syndr Hum.
Van Den Eynde et al., A New Antigen Recognized by Cytolytic T Lymphocytes on a Human Kidney Tumor Results From Reverse Strand Transcription. J Exp Med. Dec. 20, 1999;190(12):1793-1800.
Van Elsas et al., Elucidating the Autoimmune and Antitumor Effector Mechnaisms of a Treatment Based on Cytotoxic T Lymphocyte Antigen-4 Blockade in Combination with a B16 Melanoma Vaccine: Comparison of Prophylaxis and Therapy. J Exp Med. Aug. 2001.
Van Erp et al., Application of a sol particle immunoassay to the determination of affinity constants of monoclonal antibodies. J Immunoassay. 1991;12(3):425-443.
Vance et al., Patterns of Pathogenesis: Discrimination of Pathogenic and Nonpathogenic Microbes by the Innate Immune System. Cell Host Microbe. Jul. 23, 2009;6(1):10-21.
Vandamme et al., African Origin of Human T-Lymphotropic Virus Type 2 (HTLV-2) Supported by a Potential New HTLV-2d Subtype in Congolese Bambuti Efe Pygmies. J Virol. May 1998;72(5):4327-4340.
Vilas Boas et al., Cytomegalovirus Glycoprotein B Genotypes and Central Nervous System Disease in AIDS Patients. J Med Virol. Nov. 2003;71(3):404-407.
Vilchez and Butel, Emergent Human Pathogen Simian Virus 40 and Its Role in Cancer. Clin Microbiol Rev. Jul. 2004;17(3):495-508.
Virok et al., Chlamydial Infection Induces Pathobiotype-Specific Protein Tyrosine Phosphorylation in Epithelial Cells. Infect Immun. Apr. 2005;73(4):1939-1946.
Von Lindern et al., The Translocation (6;9), Associated with a Specific Subtype of Acute Myeloid Leukemia, Results in the Fusion of Two Genes, dek and can, and the Expression of a Chimeric, Leukemia-Specific dek-can mRNA. Mol Cell Biol. 1992.
Waitz et al., Potent Induction of Tumor Immunity by Combining Tumor Cryoablation with Anti-CTLA-4 Therapy. Cancer Res. Jan. 15, 2012;72(2):430-439.
Waltregny et al., Screening of histone deacetylases (HDAC) expression in human prostate cancer reveals distinct class I HDAC profiles between epithelial and stromal cells. Eur J Histochem. Jul.-Sep. 2004;48(3):273-290.
Wang et al., Alterations of APC, c-met, and p53 Genes in Tumor Tissue and Serum of Patients with Gastric Cancers. J Surg Res. Aug. 2004;120(2):242-248.
Wang et al., Cloning Genes Encoding MHC Class II-Restricted Antigens: Mutated CDC27 as a Tumor Antigen. Science. May 21, 1999;284(5418):1351-1354.
Wang et al., Identification of a Novel Major Histocompatibility Complex Class II-restricted Tumor Antigen Resulting from a Chromosomal Rearrangement Recognized by CD4$^+$ T Cells. J Exp Med. May 17, 1999;189(10):1659-1668.
Ward et al., Binding activities of a repertoire of single immunoglobulin variable domains secreted from *Escherichia coli*. Nature. Oct. 12, 1989;341(6242):544-546.
Weaver et al., Genetic determinants of Venezuelan equine encephalitis emergence. Arch Virol Suppl. 2004;(18):43-64.
Weaver et al., Venezuelan Equine Encephalitis. Annu Rev Entomol. 2004;49:141-174.
Wells et al., Swine Influenza Virus Infections Transmission. From Ill Pigs to Humans at a Wisconsin Agricultural Fair and Subsequent Probable Person-to-Person Transmission. JAMA. Jan. 23-30, 1991;265(4):478-481.
Wentworth et al., An Influenza A (H1N1) Virus, Closely Related to Swine Influenza Virus, Responsible for a Fatal Case of Human Influenza. J Virol. Apr. 1994;68(4):2051-2058.
Wille-Reece et al., HIV Gag protein conjugated to a Toll-like receptor 7/8 agonist improves the magnitude and quality of Th1 and CD8$^+$ T cell responses in nonhuman primates. Proc Natl Acad Sci U S A. Oct. 18, 2005;102(42):15190-15194.
Wille-Reece et al., Immunization with HIV-1 Gag Protein Conjugated to a TLR7/8 Agonist Results in the Generation of HIV-1 Gag-Specific Th1 and CD8$^+$ T Cell Responses. J Immunol. Jun. 15, 2005;174(12):7676-7683.
Wille-Reece et al., Toll-like receptor agonists influence the magnitude and quality of memory T cell responses after prime-boost immunization in nonhuman primates. J Exp Med. May 15, 2006;203(5):1249-1258.
Wilson et al., Simplified conjugation chemistry for coupling peptides to F(ab') fragments: autologous red cell agglutination assay for HIV-1 antibodies. J Immunol Methods. Oct. 14, 1994;175(2):267-273.
Witte et al., Innate Immune Pathways Triggered by Listeria monocytogenes and Their Role in the Induction of Cell-Mediated Immunity. Adv Immunol. 2012;113:135-156.
Woodward et al., Supporting Online Material for c-di-AMP Secreted by Intracellular Listeria monocytogenes Activates a Host Type I Interferon Response. May 27, 2010 on Science Express May 27, 2010;DOI:10.1126/science.1189801 (15 pages).
Woycechowsky and Raines, Native Disulfide Bond Formation in Proteins. Curr Opin Chem Biol. Oct. 2000;4(5):533-539.
Yan and Aguilar, Synthesis of 3',5'-cyclic diguanylic acid (cdiGMP) using 1-(4-chlorophenyl)-4-ethoxypiperidin-4-yl as a protecting group for 2'-hydroxy functions of ribonucleosides. Nucleosides Nucleotides Nucleic Acids. 2007;26(2):189-204.
Yan et al., Synthesis and immunostimulatory properties of the phosphorothioate analogues of cdiGMP. Bioorg Med Chem Lett. Oct. 15, 2008;18(20):5631-5634.
Yarmush et al., Coupling of antibody-binding fragments to solid-phase supports: site-directed binding of F(ab')$_2$ fragments. J Biochem Biophys Methods. Dec. 1992;25(4):285-297.
Yi et al., Single Nucleotide Polymorphisms of Human STING Can Affect Innate Immune Response to Cyclic Dinucleotides. PLoS One. Oct. 21, 2013;8(10):e77846.
Zaremba et al., Identification of an Enhancer Agonist Cytotoxic T Lymphocyte Peptide from Human Carcinoembryonic Antigen. Cancer Res. Oct. 15, 1997;57(20):4570-4577.
Zeier et al., New Ecological Aspects of Hantavirus Infection: A Change of A Paradigm and a Challenge of Prevention—A Review. Virus Genes. Mar. 2005;30(2):157-180.
Zhang et al., c-di-GMP Displays A Monovalent Metal Ion-Dependent Polymorphism. J Am Chem Soc. Dec. 29, 2004;126(51):16700-16701.
Zhao et al., Thiophosphate Analogs of c-di-GMP: Impact on Polymorphism. Nucleosides Nucleotides Nucleic Acids. May 2009;28(5):352-378.
Zhou et al., Endo-S-c-di-GMP Analogues-Polymorphism and Binding Studies with Class I Riboswitch. Molecules. Nov. 9, 2012;17(11):13376-13389.
Zhou et al., Potent suppression of c-di-GMP synthesis via I-site allosteric inhibition of diguanylate cyclases with 2'-F-c-di-GMP. Bioorg Med Chem. Jul. 15, 2013;21(14):4396-4404.

(56) References Cited

OTHER PUBLICATIONS

Zimmerman et al., Expression of annexin II in conventional renal cell carcinoma is correlated with Fuhrman grade and clinical outcome. Virchows Arch. Oct. 2004;445(4):368-374.

Ziyaeyan et al., The Seroprevalence of Parvovirus BI9 Infection among To-Be-Married Girls, Pregnant Women, and Their Neonates in Shi raz, Iran. Jpn J Infect Dis. Apr. 2005;58(2):95-97.

Extended European Search Report and Written Opinion issued in PCT/US2013/044744 (EP 13799826) dated Nov. 20, 2015, 10 pages.

International Search Report and Written Opinion issued in PCT/US2013/044744 dated Nov. 7, 2013, 10 pages.

International Search Report and Written Opinion issued in PCT/US2013/075189 dated Mar. 11, 2014, 11 pages.

International Search Report and Written Opinion issued in PCT/US2014/038525 dated Sep. 9, 2014, 8 pages.

International Search Report and Written Opinion issued in PCT/US2014/038526 dated Sep. 19, 2014, 8 pages.

Non Final Office Action issued in U.S. Appl. No. 13/912,960 dated Jul. 15, 2015, 10 pages.

Non Final Office Action issued in U.S. Appl. No. 14/106,687 dated Nov. 20, 2015, 12 pages.

Non Final Office Action issued in U.S. Appl. No. 14/280,667 dated Nov. 19, 2015, 10 pages.

Non Final Office Action issued in U.S. Appl. No. 14/280,668 dated Dec. 3, 2015, 10 pages.

Search Report and Written Opinion issued by IPOS in Singapore patent application No. 11201407875U dated Sep. 15, 2015, 7 pages.

Communication from the European Patent Office dated Dec. 2, 2016 for European application No. 14791304.0, 9 pages.

Libanova, et al. "Cyclic di-nucleotides: new era for small molecules as adjuvants" Microbial Biotechnology (2012) 5(2), 168-176.

Sawai et al., "Synthesis of oligoinosinates with 2'-5' internucleotide linkage in aqueous solution using Pb2+ ion", Bulletin of the Chemical Society of Japan, (1981), vol. 54, No. 9, pp. 2759-2762.

Chan et al. "Structural basis of activity and allosteric control of diguanylate cyclase", PNAS, vol. 101, No. 49, Dec. 7, 2004, pp. 17084-17089.

Gaffney et al. "One-flask Syntheses of c-di-GMP and the [Rp, Rp] and [Rp, Sp] Thiophosphate Analogs", Org Lett. 12(14), Jul. 16, 2010, pp. 3269-3271.

Kim et al. "Co-Crystal Structures of PKG Iβ (92-227) with cGMP and cAMP Reveal the Molecular Details of Cyclic-Nucleotide Binding", PLoS ONE 6(4): e18413, Apr. 19, 2011, pp. 1-15.

O'Neill, L. "Sensing the Dark Side of DNA", Science, vol. 339, Feb. 15, 2013, pp. 763-764.

Yin et al. "Cyclic di-GMP Sensing via the Innate Immune Signaling Protein STING", Molecular Cell, 46(6), Jun. 29, 2012, pp. 735-745.

Ablasser et al., "cGAS produces a 2'-5'-linked cyclic dinucleotide second messenger that activates STING," Nature, Jun. 20, 2013;498(7454):380-4. doi: 10.1038/nature12306. Epub May 30, 2013.

Barker et al., "STING-Dependent Recognition of Cyclic di-AMPMediates Type I Interferon Responses during Chlamydia trachomatis Infection," mBio, vol. 4, No. 3, Apr. 30, 2013;4(3):e00018-13.

Bowie "Innate Sensing of bacterial cyclic dinucleotides: more than just STING," Nature Immunology, Dec. 2012;13(12):1137-9.

Burdette et al., "STING and the innate immune response to nucleic acids in the cytosol," Nature Immunology, Jan. 2013;14(1):19-26.

Burdette et al., "Sting is a direct innate immune sensor of cyclic di-GMP," Nature, Sep. 25, 2011;478(7370):515-8.

Civril et al., "Structural mechanism of cytosolic DNA sensing by cGAS," Nature, Jun. 20, 2013;498(7454):332-7. doi: 10.1038/nature12305. Epub May 30, 2013.

Conlon et al., "Mouse, but not Human STING, Binds and Signals in Response to the Vascular Disrupting Agent 5,6-Dimethylxanthenone-4-Acetic Acid," J Immunol, May 15, 2013;190(10):5216-25. doi: 10.4049/jimmunol.1300097. Epub Apr. 12, 2013.

Diner et al., "The innate immune DNA sensor cGAS produces a non-canonical cyclic dinucleotide that activates human STING," Cell Rep., May 30, 2013;3(5):1355-61. doi: 10.1016/j.celrep.2013.05.009. Epub 2013 M.

Dubensky et al., "Rationale, progress and development of vaccines utilizing STING-activating cyclic dinucleotides adjuvants," Therapeutic Advances in Vaccines, Nov. 2013;1(4):131-43.

Gao et al., "Cyclic [G(2',5')pA(3',5')p] Is the Metazoan Second Messenger Produced by DNA-Activated Cyclic GMP-AMP Synthase," Cell Press, May 23, 2013;153(5):1094-107. doi: 10.1016/j.cell.2013.04.046. Epub May 3, 2013.

Gao et al., "Structure-Function Analysis of STING Activation by c[G(2',5')pA(3',5')p] and targeting by antiviral DMXAA," Cell Press, Aug. 15, 2013;154(4):748-62. doi: 10.1016/j.cell.2013.07.023. Epub Aug. 1, 2013.

Huang et al., "The Structural basis for the sensing and binding of cyclic di-GMP by STING," Nature Structural and Molecular Biology, Jun. 24, 2012;19(7):728-30.

Jin et al., "MPYS is Required for IFN Response Factor 3 Activation and Type I IFN Production in the Response of Cultured Phagocytes to Bacterial Second Messengers Cyclic-di-AMP and Cyclic-di-GMP," J. Immunol., Sep. 1, 2011;187(5):2595-601.

Lam et al., "Adenovirus Detection by the cGAS/STING/TBK1 DNASensing Cascade," Journal of Virology, Jan. 2014;88(2):974-81. doi: 10.1128/JVI.02702-13. Epub Nov. 6, 2013.

Mathew et al., "Cytosolic delivery of antisense oligonucleotides by listeriolysin O-containing liposomes," Genbe Therapy, Jul. 2003;10(13):1105-15.

Miyabe et al., "A New Adjuvant delivery system 'cyclic di-GMP/YSK05 liposome' for cancer immunotherapy," J Control Release, Jun. 28, 2014;184:20-7. doi: 10.1016/j.jconrel.2014.04.004. Epub Apr. 13, 2014.

Parvatiyar et al., "The Helicase DDX41 recognizes the bacterial secondary messengers cyclic di-GMP and cyclic di-AMP to activate a type I interferon immune response," Nature Immunology, Dec. 2012;13(12):1155-61. doi: 10.1038/ni.2460. Epub.

Roembke et al., "A cyclic dinucleotide containing 2-aminopurine is a general fluorescent sensor for c-di-GMP and 3',3'-cGAMP," Mol. BioSyst., Jun. 2014;10(6):1568-75. doi: 10.1039/c3mb70518h. Epub.

Sauer et al., "The N-ethyl-N-nitrosourea-induced Goldenticket mouse mutant reveals an essential function of Sting in the in vivo interferon response to Listeria monocytogenes and cyclic dinucleotides." Infect Immun, Feb. 2011;79(2):688-94. doi: 10.1128/IAI.00999-.

Shu et al., "Structure of STING bound to cyclic di-GMP reveals the mechanism of cyclic dinucleotide recognition by the immune system," Nature Structural & Molecular Biology, Jun. 24 2012;19(7):722-4.

Sun et al., "Cyclic GMP-AMP synthase is a cytosolic DNA sensor that activates the type I interferon pathway," Science, Feb. 15, 2013;339(6121):786-91. doi: 10.1126/science.1232458. Epub Dec. 20, 2012.

Woodward et al., "c-di-AMP secreted by intracellular Listeria monocytogenes activates a host type I interferon response," Science, Jun. 25, 2010;328(5986):1703-5. doi: 10.1126/science.1189801. Epub May 27, 2010.

Wu et al., "Cyclic GMP-AMP is an endogenous second messenger in innate immune signaling by cytosolic DNA," Science, Feb. 15, 2013;339(6121):826-30. doi: 10.1126/science.1229963. Epub Dec. 20, 2012.

Zhang et al., "Cyclic GMP-AMP containing mixed phosphodiester linkages is an endogenous high-affinity ligand for STING," Molecular Cell, Jul. 25, 2013;51(2):226-35. doi: 10.1016/j.molcel.2013.05.022. Epub Jun. 6, 2013.

Libanova et al. "Cyclic di-nucleotides: new era for small molecules as adjuvants", Microbial Biotechnology, Feb. 20, 2012, vol. 5, No. 2, pp. 168-176.

Howgate, et al. "Conversion of 2',3'-O-isopropylideneadenosine into 9-(6-deoxy-B-D-allofuranosyl)-and 9-(6-deoxy-α-L-talofuranosyl)-adenines" Carbohydrate Research, vol. 21, Issue 2, Feb. 1972, pp. 309-315. Abstract Only.

Quyang, et al. "Structural analysis of the STING adaptor protein reveals a hydrophobic dimer interface and mode of cyclic di-GMP binding" Immunity (2012) 36 p. 1073-86.

(56) References Cited

OTHER PUBLICATIONS

Principles of Protein X-ray Crystallography, Springer, https/books.google., 2007, p. 19.
Amiot, et al. "New Approach for the Synthesis of c-di-GMP and Its Analogues", Synthesis 2006, No. 24, pp. 4230-4236.
Patel et al., Filing receipt plus Specification minus claims for U.S. Appl. No. 61/817,269, filed Apr. 29, 2013.
Patel et al., Filing receipt minus Specification plus claims for U.S. Appl. No. 61/817,269, filed Apr. 29, 2013.
Porter et al. (eds.), Merck Manual of Diagnosis and Therapy, 19th Ed., Chapter 124, Section 9, Whitehouse Station, NJ, 2011.
Venes et al. (eds.), Taber's Cyclopedic Medical Dictionary, 21st Ed., F.A. Davis Co., Inc., Philadelphia, PA, 2009, only p. 1163 supplied, see "Immunotherapy".
Su et al., STING Activation in Cancer Immunotherapy, Theranostics, 9(25), 7759-7771, 2019.

* cited by examiner

FIG. 2

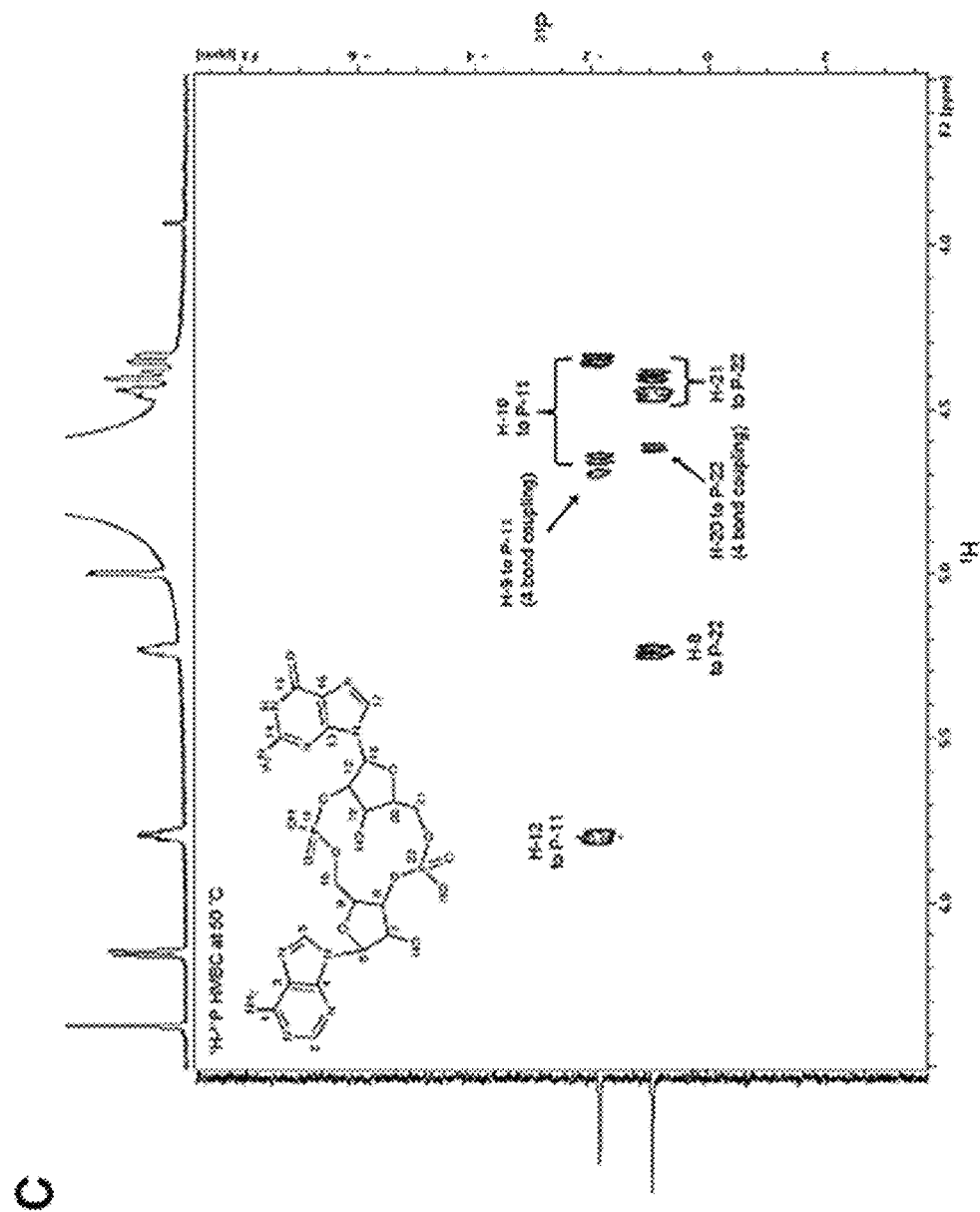
FIG. 6 (CON'T)

CYCLIC DI-NUCLEOTIDE INDUCTION OF TYPE I INTERFERON

CROSS REFERENCE TO RELATED APPLICATIONS

This application is a continuation of U.S. patent application Ser. No. 16/279,950, filed on Feb. 19, 2019, which application is a continuation of U.S. patent application Ser. No. 14/268,967, filed on May 2, 2014, which application, under 35 U.S.C. § 119(e), claims priority to the filing date of U.S. Provisional Patent Application Ser. No. 61/819,499, filed on May 3, 2013; the disclosure of which applications are incorporated herein by reference.

GOVERNMENT RIGHTS

This invention was made with government support under grant nos. AI063302, AI075039, AI080749, AI082357, and OD008677 awarded by the National Institutes of Health. The government has certain rights in the invention.

INTRODUCTION

Interferons (also referred to as "IFN" or "IFNs") are proteins having a variety of biological activities, some of which are antiviral, immunomodulating and antiproliferative. They are relatively small, species-specific, single chain polypeptides, produced by mammalian cells in response to exposure to a variety of inducers such as viruses, polypeptides, mitogens and the like. Interferons protect animal tissues and cells against viral attack and are an important host defense mechanism. In most cases, interferons provide better protection to tissues and cells of the kind from which they have been produced than to other types of tissues and cells, indicating that human-derived interferon could be more efficacious in treating human diseases than interferons from other species. Interferons may be classified as Type-I, Type-Hand Type-Ill interferons. Mammalian Type-I interferons include IFN-α (alpha), IFN-β (beta), IFN-κ (kappa), IFN-δ (delta), IFN-ε (epsilon), IFN-τ (tau), IFN-ω (omega), and IFN-ζ (zeta, also known as limitin).

Agents that induce interferon production find use as vaccine adjuvants and in formulations that initiate effector and memory T-cell responses. Effective adjuvants enhance specific immune responses to antigens while minimizing toxic side effects, reducing the dose and dosage of vaccinations, and broadening the immune response. There remains a need for effective adjuvants that may be coformulated with antigens derived from intracellular pathogens and cancer cells to activate an effective cellular and humoral immune response to treat intracellular pathogens and reduce tumor burden. The immunomodulatory activity of interferon proteins, and the signaling pathways that regulate interferon production, are drawing interest as a target for designing new adjuvants.

Interferons have potential in the treatment of a large number of human cancers since these molecules have anti-cancer activity that acts at multiple levels. First, interferon proteins can directly inhibit the proliferation of human tumor cells. The anti-proliferative activity is also synergistic with a variety of approved chemotherapeutic agents such as cisplatin, 5FU and paclitaxel. Secondly, the immunomodulatory activity of interferon proteins can lead to the induction of an anti-tumor immune response. This response includes activation of NK cells, stimulation of macrophage activity and induction of MHC class I surface expression, leading to the induction of anti-tumor cytotoxic T lymphocyte activity. In addition, interferons play a role in cross-presentation of antigens in the immune system. Moreover, some studies further indicate that IFN-β protein may have anti-angiogenic activity. Angiogenesis, new blood vessel formation, is critical for the growth of solid tumors. Evidence indicates that IFN-β may inhibit angiogenesis by inhibiting the expression of pro-angiogenic factors such as bFGF and VEGF. Lastly, interferon proteins may inhibit tumor invasiveness by modulating the expression of enzymes, such as collagenase and elastase, which are important in tissue remodeling.

Interferons also appear to have antiviral activities that are based on two different mechanisms. For instance, type I interferon proteins (α and β) can directly inhibit the replication of human hepatitis B virus ("HBV") and hepatitis C virus ("HCV"), but can also stimulate an immune response that attacks cells infected with these viruses.

SUMMARY

Methods and compositions are provided for increasing the production of a type I interferon (IFN) in a cell. Aspects of the methods include increasing the level of a 2'-5' phosphodiester linkage comprising cyclic-di-nucleotide in a cell in a manner sufficient to increase production of the type I interferon (IFN) by the cell. Also provided are compositions and kits for practicing the subject methods.

In one aspect, provided herein is a method for increasing the production of a type I interferon (IFN) in a cell by increasing the level of a 2'-5' phosphodiester linkage containing cyclic-di-nucleotide in the cell in a manner sufficient to increase production of the type I interferon (IFN) by the cell.

In certain embodiments, the method includes the step of contacting the cell with the cyclic-di-nucleotide. In certain embodiments, the cyclic-di-nucleotide has two 2'-5' phosphodiester linkages. In other embodiments, the cyclic-di-nucleotide has a 2'-5' phosphodiester linkage and a 3'-5' phosphodiester linkage.

In certain embodiments, the cyclic-di-nucleotide comprises a guanosine nucleoside. In some embodiments, the cyclic-di-nucleotide contains two guanosine nucleosides. In certain embodiments, the cyclic-di-nucleotide comprises an adenosine nucleoside. In some embodiments, the cyclic-di-nucleotide contains two adenosine nucleosides. In other embodiments, the cyclic-di-nucleotide comprises an adenosine nucleoside and a guanosine nucleoside.

In certain embodiments, the cyclic-di-nucleotide has the following formula:

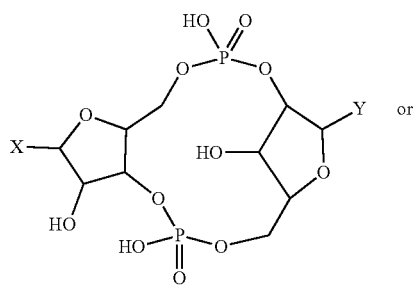

-continued

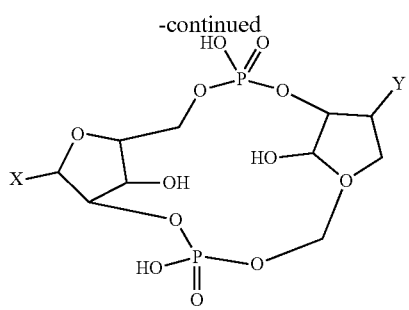

wherein X and Y are each:

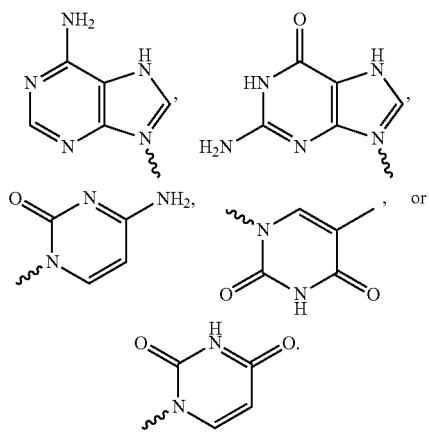

In some embodiments, the cyclic-di-nucleotide has the following formula:

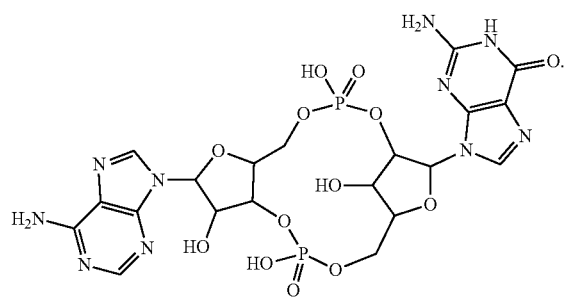 [SMILES: Nc1nc2c(ncn2C2OC3COP(=O)(O)OC4C(COP(=O)(O)OC2C3O)OC(n2cnc3c(N)ncnc32)C4O)c(=O)[nH]1]

In certain embodiments of the method, the level of the cyclic-di-nucleotide is increased by increasing the activity of a cGAMP synthase (cGAS) in the cell. In some embodiments, the activity of the cGAS is increased by enhancing expression of a nucleic acid encoding cGAS. In some embodiments, the activity of the cGAS is increased by introducing a nucleic acid encoding the cGAS into the cell.

In certain embodiments, the method is for increasing the production of interferon (IFN) alpha. In other embodiments, the IFN is interferon beta.

In certain embodiments, the method is for increasing the production of a type I interferon (IFN) in a mammalian cell. In particular embodiments, mammalian cell is a human cell. In some embodiments, the cell is in vitro. In other embodiments, the cell is in vivo.

In another aspect, provided herein is a method for increasing the production of a type I interferon (IFN) in a subject, the method includes the step of administering to the subject an amount of a 2'-5' phosphodiester linkage comprising cyclic-di-nucleotide active agent effective to increase the production of the type I interferon in the subject.

The active agent can include, but is not limited to, any of the 2'-5' phosphodiester linkage containing cyclic-di-nucleotides described herein. In certain embodiments, the cyclic-di-nucleotide has two 2'-5' phosphodiester linkages. In other embodiments, the cyclic-di-nucleotide has a 2'-5' phosphodiester linkage and a 3'-5' phosphodiester linkage.

In some embodiments, the cyclic-di-nucleotide contains a guanosine nucleoside. In certain embodiments, the cyclic-di-nucleotide contains two guanosine nucleosides. In some embodiments, the cyclic-di-nucleotide contains an adenosine nucleoside. In specific embodiments, the cyclic-di-nucleotide contains two adenosine nucleosides. In other embodiments, the cyclic-di-nucleotide contains an adenosine and a guanosine nucleoside. In some embodiments, the cyclic-di-nucleotide has the following formula:

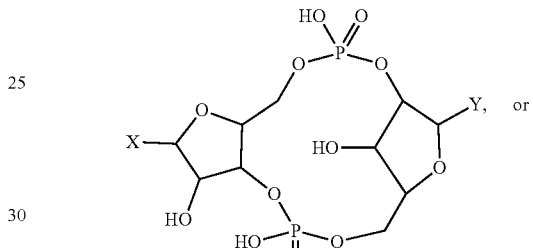

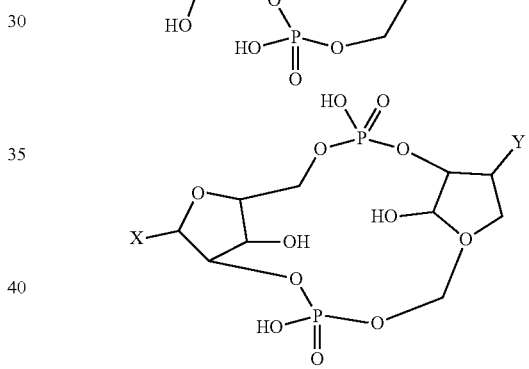

wherein X and Y are each:

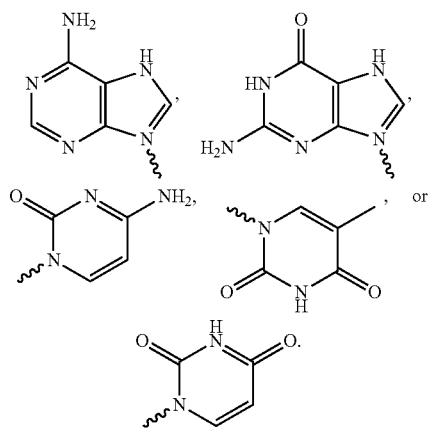

In some embodiments of the subject method, the cyclic-di-nucleotide has the following formula:

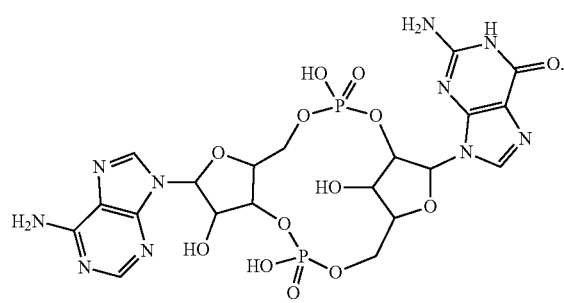

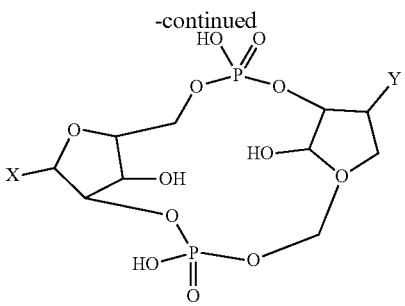

wherein X and Y are each:

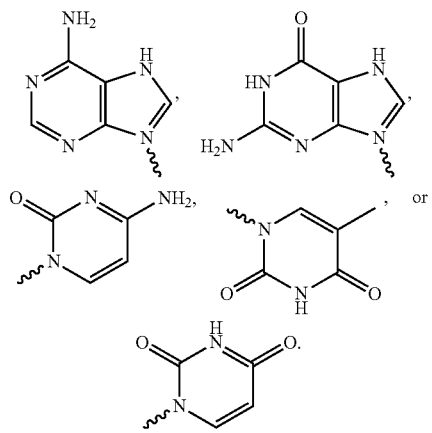

In some embodiments of the subject method, the cyclic-di-nucleotide has the following formula:

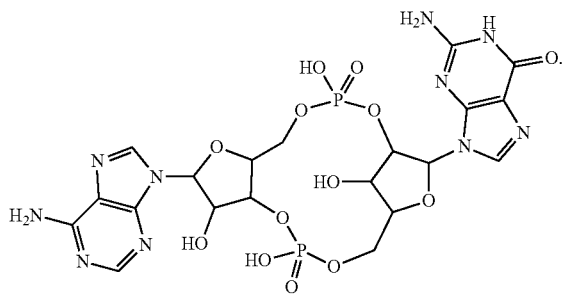 [SMILES: Nc1nc2c(ncn2C2OC3COP(=O)(O)OC4C(COP(=O)(O)OC2C3O)OC(n2cnc3c(N)ncnc32)C4O)c(=O)[nH]1]

In certain embodiments, the 2'-5' phosphodiester linkage comprising cyclic-di-nucleotide active agent includes an agent that increases cellular activity of a cGAMP synthase (cGAS). In specific embodiments, the agent comprises a nucleic acid encoding the cGAS.

In certain embodiments, the method is for increasing the production of interferon (IFN) alpha in a subject. In other embodiments, the method is for increasing the production of interferon beta in a subject.

In certain embodiments, the subject has a viral infection. In certain embodiments, the subject has a bacterial infection. In other embodiments, the subject has a neoplastic disease. In certain embodiments, the subject is mammal. In some embodiments, the mammal is a human.

In another aspect, provided herein is a method for increasing a stimulator of interferon genes (STING) mediated response in a subject, the method includes the step of administering to the subject an amount of a STING active agent effective to increase a STING mediated response in the subject. In certain embodiments, the STING mediated response is non-responsive to a cyclic-di-nucleotide having two 3'-5' phosphodiester bonds.

The STING active agent can include, but is not limited to, any of the 2'-5' phosphodiester linkage containing cyclic-di-nucleotides described herein. In certain embodiments, the cyclic-di-nucleotide has two 2'-5' phosphodiester linkages. In other embodiments, the cyclic-di-nucleotide has a 2'-5' phosphodiester linkage and a 3'-5' phosphodiester linkage.

In some embodiments, the cyclic-di-nucleotide contains a guanosine nucleoside. In certain embodiments, the cyclic-di-nucleotide contains two guanosine nucleosides. In some embodiments, the cyclic-di-nucleotide contains an adenosine nucleoside. In specific embodiments, the cyclic-di-nucleotide contains two adenosine nucleosides. In other embodiments, the cyclic-di-nucleotide contains an adenosine and a guanosine nucleoside. In some embodiments, the cyclic-di-nucleotide has the following formula:

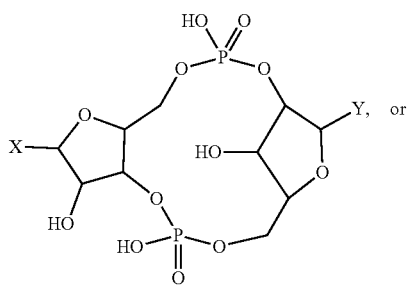

In certain embodiments, the STING active agent includes an agent that increases cellular activity of a cGAMP synthase (cGAS). In specific embodiments, the agent comprises a nucleic acid encoding the cGAS.

In certain embodiments, the STING active agent includes an agent that increases cellular activity of STING. In specific embodiments, the agent comprises a nucleic acid encoding the STING.

In certain embodiments, the subject has a viral infection. In certain embodiments, the subject has a bacterial infection. In other embodiments, the subject has a neoplastic disease. In certain embodiments, the subject is mammal. In some embodiments, the mammal is a human.

In another aspect, provided herein is a cyclic-di-nucleotide comprising a 2'-5' phosphodiester linkage. Such cyclic-di-nucleotides are useful, for example, in practicing the subject methods, including, but not limited to, methods for increasing the production of a type I interferon in a cell or a subject.

In certain embodiments, the cyclic-di-nucleotide has two 2'-5' phosphodiester linkages. In other embodiments, the cyclic-di-nucleotide has a 2'-5' phosphodiester linkage and a 3'-5' phosphodiester linkage.

In certain embodiments, the cyclic-di-nucleotide contains a guanosine nucleoside. In some embodiments, the cyclic-di-nucleotide contains two guanosine nucleosides. In certain embodiments, the cyclic-di-nucleotide contains an adenosine nucleoside. In some embodiments, the cyclic-di-nucleotide contains two adenosine nucleosides. In other embodiments, the cyclic-di-nucleotide contains an adenosine and a guanosine nucleoside.

In some embodiments, the cyclic-di-nucleotide has the following formula:

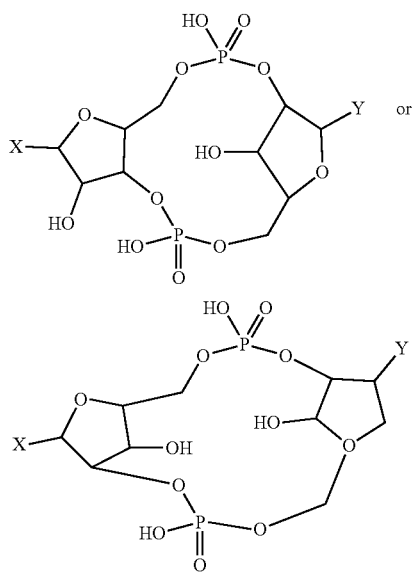

wherein X and Y are each:

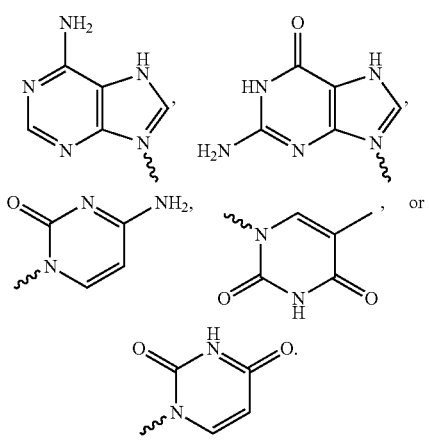

In certain embodiments, the cyclic-di-nucleotide has the following formula:

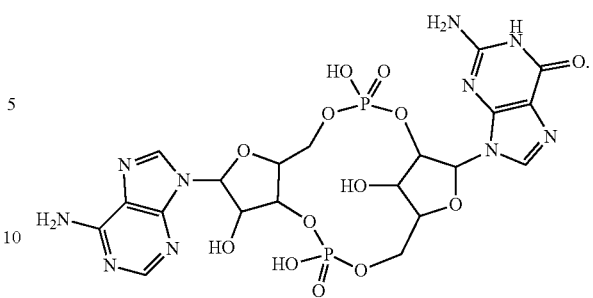

In another aspect, provided herein is a composition containing a 2'-5' phosphodiester linkage containing cyclic-di-nucleotide and a pharmaceutically acceptable carrier.

In certain embodiments, the cyclic-di-nucleotide has two 2'-5' phosphodiester linkages. In other embodiments, the cyclic-di-nucleotide has a 2'-5' phosphodiester linkage and a 3'-5' phosphodiester linkage.

In certain embodiments of the composition, the cyclic-di-nucleotide contains a guanosine nucleoside. In some embodiments, the cyclic-di-nucleotide contains two guanosine nucleosides. In certain embodiments, the cyclic-di-nucleotide contains an adenosine nucleoside. In some embodiments, the cyclic-di-nucleotide contains two adenosine nucleosides. In other embodiments, the cyclic-di-nucleotide contains an adenosine and a guanosine nucleoside.

In certain embodiments of the composition, the cyclic-di-nucleotide has the following formula:

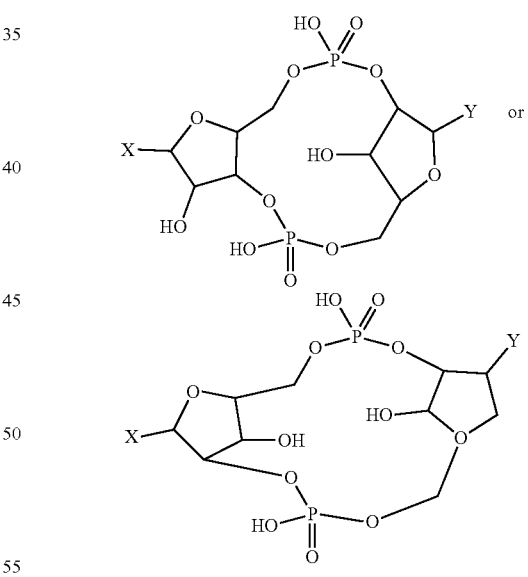

wherein X and Y are each:

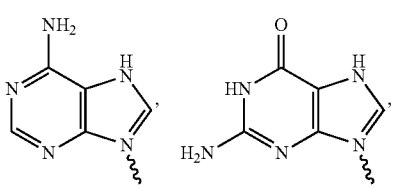

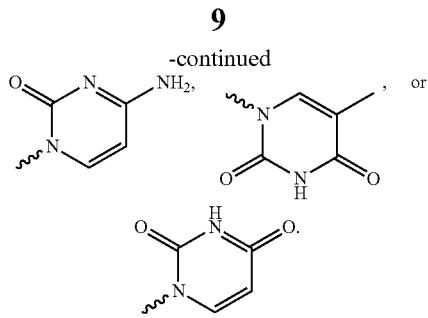

In certain embodiments of the composition, the cyclic-di-nucleotide has the following formula:

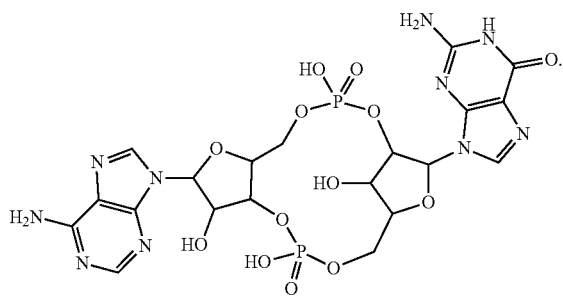 [SMILES: Nc1nc2c(ncn2C2OC3COP(=O)(O)OC4C(COP(=O)(O)OC2C3O)OC(n2cnc3c(N)ncnc32)C4O)c(=O)[nH]1]

BRIEF DESCRIPTION OF THE FIGURES

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures:

FIG. 2 shows the sequence alignment of hSTING variants. hSTING was cloned from THP-1 cells (THP: SEQ ID NO:06) compared to the reference STING allele (NCBI NP_938023.1; hREF: SEQ ID NO:05).

DETAILED DESCRIPTION

Figures 1A, 1B, 1C:
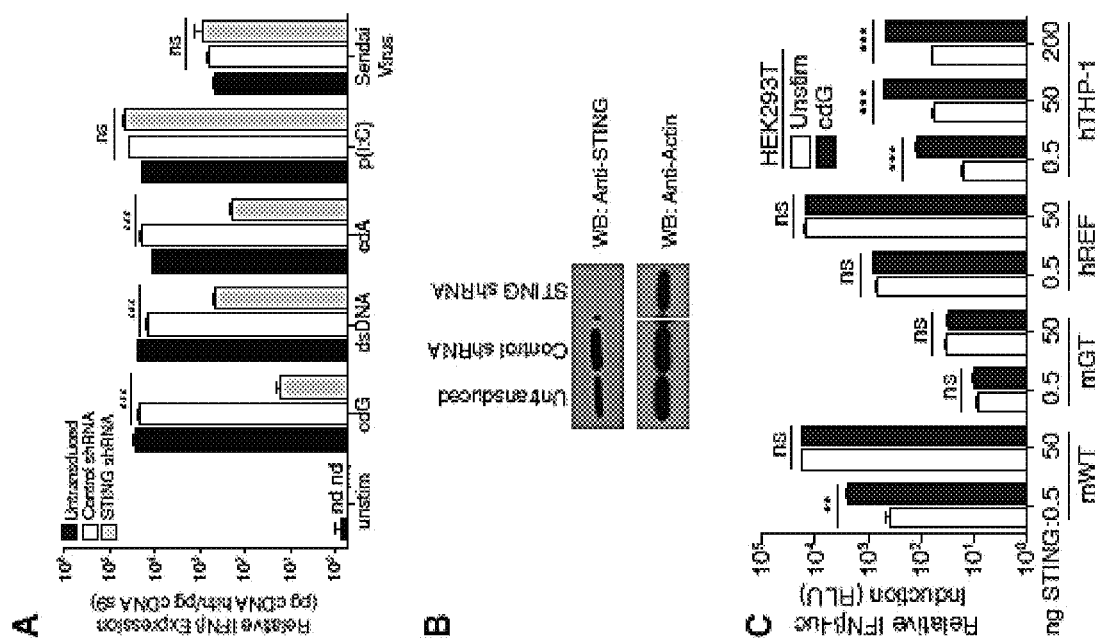
FIG. 1, panels A-F show the variable responsiveness of human STING variants to cyclic-di-nucleotides maps to arginine 232. (Panel A) THP-1 cells were transduced with vectors encoding an shRNA targeting STING or a control shRNA. Cells were then stimulated with cyclic-di-GMP (cdG), dsDNA, cyclic-di-AMP (cdA), poly-inosine:cytosine (pI:C), or Sendai Virus, and induction of human interferon-β mRNA was assessed by quantitative reverse transcriptase PCR. (Panel B) Western blotting confirmed that knockdown of STING was effective. (Panel C) HEK293T cells were transfected with the indicated amounts of various mouse (m) or human (h) STING expression plasmid and then stimulated 6 h later by transfection with synthetic cdG (5 μM). GT denotes the null I199N allele of Sting from Goldenticket (Gt) mice. STING activation was assessed by use of a co-transfected IFN-luciferase reporter construct. (Panel D) Gt (STING-null) macrophages were transduced with retroviral vectors encoding the indicated STING alleles and were then stimulated 48 h later by transfection with cdG (5 μM) or dsDNA 70-mer oligonucleotide (0.5 μg/mL). IFN induction was measured by qRT-PCR. ND, not detected. (Panel E) Binding assay of STING to 32P-c-di-GMP. STING proteins were expressed in HEK293T cells and cell lysates were subjected to UVcrosslinking with $^{32}$P-cdG, and resolved by SDS-PAGE. Binding was quantified by autoradiography. Western blots of cell lysates with an anti-STING polyclonal antibody confirmed similar expression of the various STING proteins. (Panel F) Responsiveness of mSTING to cGAMP is affected by mutations of R231. The indicated mutants were tested as in C.

Methods and compositions are provided for increasing the production of a type I interferon (IFN) in a cell. Aspects of the methods include increasing the level of a 2'-5' phosphodiester linkage comprising cyclic-di-nucleotide in a cell in a manner sufficient to increase production of the type I interferon (IFN) by the cell. Also provided are compositions and kits for practicing embodiments of the subject methods.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating recited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be constructed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Methods

As summarized above, methods of increasing the production of a type I interferon (IFN) in a cell, e.g., in vitro or in vivo are provided. By increasing type-I interferon production is meant that the subject methods increase type-I interferon production in a cell, as compared to a control. The magnitude of the increase may vary, and in some instances is 2-fold or greater, such as 5-fold or greater, including 10-fold or greater, as compared to a suitable control. As such, in some instances, the methods are methods of increasing type-I interferon production in a cell, e.g., by a magnitude of 2-fold or greater, such as 5-fold or greater, including 10-fold or greater, as compared to a suitable control. In those embodiments where, prior to practice of the methods, interferon production is not-detectable, the increase may result in detectable amounts of interferon production. Interferon production can be measured using any suitable method, including, but not limited to, vesicular stomatitis virus (VSV) challenge bioassay, enzyme-linked immunosorbent assay (ELISA) replicon based bioassays or by using a reporter gene (e.g., luciferase) cloned under regulation of a Type I interferon signaling pathway. See, e.g., Meager *J. Immunol. Methods* 261:21-36 (2002); Vrolijk et al. C. J. *Virol. Methods* 110:201-209 (2003); and Francois et al. *Antimicrob Agents Chemother* 49(9):3770-3775 (2005).

The methods may be used to increase the production of any type I interferon including, but not limited to: IFN-α (alpha), IFN-β (beta), IFN-κ (kappa), IFN-δ (delta), IFN-ε (epsilon), IFN-τ (tau), IFN-ω (omega), and IFN-ζ (zeta, also known as limitin). In some embodiments, the method is for increasing the production of IFN-α. In some embodiments, the method is for increasing IFN-β.

Aspects of the methods include increasing the level of a 2'-5' phosphodiester linkage comprising cyclic-di-nucleotide in a cell in a manner sufficient to increase production of the type I interferon by the cell. By increasing the level of a 2'-5' phosphodiester linkage comprising cyclic-di-nucleotide is meant that the subject methods increase the amount of a 2'-5' phosphodiester linkage comprising cyclic-di-nucleotide as compared to a control. As demonstrated in the Experimental Section below, 2'-5' phosphodiester linkage comprising cyclic-di-nucleotides can increase the levels of type I interferon production. The magnitude of the increase may vary, and in some instances is 2-fold or greater, such as 5-fold or greater, including 10-fold or greater, 15-fold greater, 20-fold greater, 25-fold greater, 30-fold greater, 35-fold greater, 40-fold greater, 45-fold greater, 50-fold greater, or 100 fold greater, as compared to a suitable control.

Increasing the level of a 2'-5' phosphodiester linkage comprising cyclic-di-nucleotide levels can be accomplished using a variety of different approaches. In some instances, the method includes providing a target cell with a cyclic-di-nucleotide active agent that increases 2'-5' phosphodiester linkage comprising cyclic-di-nucleotide levels in the target cell. Cyclic-di-nucleotide active agents may vary, and include, but are not limited to: small molecules, nucleic acid, protein, and peptide agents.

In some embodiments, the cyclic-di-nucleotide active agent increases IFN-α (alpha), IFN-β (beta), IFN-κ (kappa), IFN-δ (delta), IFN-ε (epsilon), IFN-τ (tau), IFN-ω (omega), and/or IFN-ζ (zeta, also known as limitin) in a cell or subject as compared to a control that has not been contacted with the cyclic-di-nucleotide active agent. In such embodiments, the increase is from 1.5-fold increase to 50-fold increase or more, including 2-fold increase to 45-fold increase, 5-fold increase to 40-fold increase, 10-fold increase to 35-fold increase, 15-fold increase to 30-fold increase, 20-fold increase to 30-fold increase, and the like.

In some instances, the cyclic-di-nucleotide active agent is a 2'-5' phosphodiester linkage containing cyclic-di-nucleotide or a functional analogue thereof. 2'-5' phosphodiester linkage containing cyclic-di-nucleotide include, but are not limited to, those 2'-5' phosphodiester linkage containing cyclic-di-nucleotides described herein.

As used herein "cyclic-di-nucleotide" refers to a compound containing two nucleosides (i.e., a first and second nucleoside), wherein the 2' or 3' carbon of each nucleoside is linked to the 5' carbon of the other nucleoside by a phosphodiester bond. Therefore, a 2'-5' phosphodiester linkage containing cyclic-di-nucleotide refers to a cyclic-di-nucleotide, wherein the 2' carbon of at least the first or second nucleosides is linked to the 5' carbon of the other nucleoside. 2'-5' phosphodiester linkage containing cyclic-di-nucleotide are discussed in greater detail below.

Functional analogues of 2'-5' phosphodiester linkage containing cyclic-di-nucleotides are those compounds that exhibit similar functional activity (e.g., increasing the production of a type I IFN) and may have a similar structure to a 2'-5' phosphodiester linkage containing cyclic-di-nucleotide. In some instances, the functional analogue is a small molecule agent. Naturally occurring or synthetic small molecule compounds of interest include numerous chemical classes, such organic molecules, including small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Such molecules may be identified, among other ways, by employing suitable screening protocols.

In some instances, the cyclic-di-nucleotide active agent is an agent that increases the cellular activity of a cyclic GMP-AMP synthase (cGAS). As discussed in the Experimental Section, below, increasing the levels cGMP synthase (cGAS) can increase the production and/or activity of cyclic-di-nucleotide in a cell. As such, a target cell may be contacted with an agent that increases cGMP synthase production and/or cellular activity in a manner sufficient to increase the production of Type I interferon in the cell. In some embodiments, the cyclic-di-nucleotide active agent is a nucleic acid encoding a cGAS. Nucleic acids encoding various cGAS enzymes include, but are not limited to, those described in: Sun et al. *Science* 339(6121):786-91 and those deposited in GENBANK and assigned deposit numbers: NM_138441.2 and NP_612450.2 (human); NM_173386.4 and NP_775562.2 (*Mus musculus*).

In certain embodiments, the nucleic acid encoding cGAS has the following sequence:

(SEQ ID NO: 01)
agcctgggttcccttcgggtcgcagactcttgtgtgcccgccagtagt gcttggtttccaacagctgctgctggctcttcctcttgcggccttttcct gaaacggattcttctttcggggaacagaaagcgccagccatgcagccttg gcacggaaaggccatgcagagagcttccgaggccggagccactgccccca aggcttccgcacggaatgccaggggcgccccgatggatcccaccgagtct ccggctgccccgaggccgccctgcctaaggcgggaaagttcggccccgc caggaagtcgggatcccggcagaaaaagagcgccccggacacccaggaga ggccgcccgtccgcgcaactgggggccgcgccaaaaaggcccctcagcgc gcccaggacacgcagccgtctgacgccaccagcgcccctggggcagaggg gctggagcctcctgcggctcgggagccggctcttttccagggctggttctt gccgccagaggggcgcgcgctgctccacgaagccaagacctccgcccggg ccctgggacgtgcccagccccggcctgccggtctcggcccccattctcgt acggagggatgcggcgcctgggggcctcgaagctccgggcggttttggaga agttgaagctcagccgcgatgatatctccacggcggcggggatggtgaaa ggggttgtggaccacctgctgctcagactgaagtgcgactccgcgttcag aggcgtcgggctgctgaacaccgggagctactatgagcacgtgaagattt ctgcacctaatgaatttgatgtcatgtttaaactggaagtccccagaatt caactagaagaatattccaacactcgtgcatattactttgtgaaatttaa aagaaatccgaaagaaaatcctctgagtcagttttttagaaggtgaaatat tatcagcttctaagatgctgtcaaagtttaggaaaatcattaaggaagaa attaacgacattaaagatacagatgtcatcatgaagaggaaagaggagg gagccctgctgtaacacttcttattagtgaaaaaatatctgtggatataa ccctggctttggaatcaaaaagtagctggcctgctagcacccaagaaggc ctgcgcattcaaaactggctttcagcaaaagttaggaagcaactacgact aaagccatttttaccttgtacccaagcatgcaaaggaaggaaatggtttcc aagaagaaacatggcggctatccttctctcacatcgaaaaggaaattttg aacaatcatggaaaatctaaaacgtgctgtgaaaacaaagaagagaaatg ttgcaggaaagattgtttaaaactaatgaaataccttttagaacagctga aagaaaggtttaaagacaaaaaacatctggataaattctcttcttatcat gtgaaaactgccttctttcacgtatgtacccagaaccctcaagacagtca gtgggaccgcaaagacctgggcctctgctttgataactgcgtgacatact ttcttcagtgcctcaggacagaaaaacttgagaattatttattcctgaa ttcaatctattctctagcaacttaattgacaaaagaagtaaggaatttct gacaaagcaaattgaatatgaaagaaacaatgagtttccagttttgatg

```
                       -continued
aattttgagattgtattttagaaagatctaagaactagagtcaccctaa atcctggagaatacaagaaaaatttgaaaaggggccagacgctgtggctc ac.
```

In some embodiments, the nucleic acid encoding cGAS is a nucleic acid with 40% to 99%, 45% to 99%, 50% to 99%, 55% to 99%, 60% to 99%, 65% to 99%, 70% to 99%, 75% to 99%, 80% to 99%, 85% to 99%, 90% to 99% or, 95% to 99% sequence identity with a wild type cGAS nucleic acid sequence. In some embodiments, the nucleic acid encoding cGAS is a nucleic acid with 40% to 50%, 50% to 60%, 60% to 70%, 70% to 80%, 80% to 90%, or 90 to 99% sequence identity with a wild type cGAS nucleic acid sequence. In some embodiments, the nucleic acid encoding cGAS is a nucleic acid with 40% or more, 45% or more, 50% or more, 55% or more, 60% or more, 70% or more, 75% or more, 80% or more, 85% or more, 90% or more, 95% or more or 99% or more sequence identity with a wild type cGAS nucleic acid sequence.

In some instances, the cyclic-di-nucleotide active agent is a vector containing a nucleic acid encoding cGAS. Vectors may be provided directly to the subject cells. In other words, the cells are contacted with vectors having the nucleic acid encoding the cyclic-di-nucleotide active agent(s) (e.g., a nucleic acid encoding cGAS) such that the vectors are taken up by the cells. Methods for contacting cells with nucleic acid vectors that are plasmids, such as electroporation, calcium chloride transfection, and lipofection, are well known in the art. For viral vector delivery, the cells are contacted with viral particles comprising the nucleic acid encoding the cyclic-di-nucleotide agent(s). Retroviruses, for example, lentiviruses, are particularly suitable to the method of the invention. Commonly used retroviral vectors are "defective", i.e., unable to produce viral proteins required for productive infection. Rather, replication of the vector requires growth in a packaging cell line. To generate viral particles comprising nucleic acids of interest, the retroviral nucleic acids comprising the nucleic acid are packaged into viral capsids by a packaging cell line. Different packaging cell lines provide a different envelope protein (ecotropic, amphotropic or xenotropic) to be incorporated into the capsid, this envelope protein determining the specificity of the viral particle for the cells (ecotropic for murine and rat; amphotropic for most mammalian cell types including human, dog and mouse; and xenotropic for most mammalian cell types except murine cells). The appropriate packaging cell line may be used to ensure that the cells are targeted by the packaged viral particles. Methods of introducing the retroviral vectors comprising the nucleic acid encoding the reprogramming factors into packaging cell lines and of collecting the viral particles that are generated by the packaging lines are well known in the art.

Vectors used for providing the nucleic acids encoding the cyclic-di-nucleotide activity active agent(s) to the subject cells may include suitable promoters for driving the expression, that is, transcriptional activation, of the nucleic acid of interest. In other words, the nucleic acid of interest will be operably linked to a promoter. This may include ubiquitously acting promoters, for example, the CMV-β-actin promoter, or inducible promoters, such as promoters that are active in particular cell populations or that respond to the presence of drugs such as tetracycline. By transcriptional activation, it is intended that transcription will be increased above basal levels in the target cell by 10 fold or more, by 100 fold or more, by 1000 fold or more. In addition, vectors used for providing cyclic-di-nucleotide active agent(s) to the subject cells may include nucleic acid sequences that encode for selectable markers in the target cells, so as to identify cells that have taken up the cyclic-di-nucleotide activity active agent(s).

Cyclic-di-nucleotide active agent(s) may also be provided to cells as polypeptides. For example, in some instances the cyclic-di-nucleotide active agent is a cGAS polypeptide. Amino acid sequences of various cGAS enzymes include, but are not limited to, those described in: Sun et al. *Science* 339(6121):786-91 and those deposited in GENBANK and assigned deposit numbers: NM_138441.2 and NP_612450.2 (human); NM_173386.4 and NP_775562.2 (*Mus musculus*).

In certain embodiments, the cGAS polypeptide has the following sequence:

```
                                              (SEQ ID NO: 02)
MQPWHGKAMQRASEAGATAPKASARNARGAPMDPTESPAAPEAALPKAG

KFGPARKSGSRQKKSAPDTQERPPVRATGARAKKAPQRAQDTQPSDATS

APGAEGLEPPAAREPALSRAGSCRQRGARCSTKPRPPPGPWDVPSPGLP

VSAPILVRRDAAPGASKLRAVLEKLKLSRDDISTAAGMVKGVVDHLLLR

LKCDSAFRGVGLLNTGSYYEHVKISAPNEFDVMFKLEVPRIQLEEYSNT

RAYYFVKFKRNPKENPLSQFLEGEILSASKMLSKFRKIIKEEINDIKDT

DVIMKRKRGGSPAVTLLISEKISVDITLALESKSSWPASTQEGLRIQNW

LSAKVRKQLRLKPFYLVPKHAKEGNGFQEETWRLSFSHIEKEILNNHGK

SKTCCENKEEKCCRKDCLKLMKYLLEQLKERFKDKKHLDKFSSYHVKTA

FFHVCTQNPQDSQWDRKDLGLCFDNCVTYFLQCLRTEKLENYFIPEFNL

FSSNLIDKRSKEFLTKQIEYERNNEFPVFDEF.
```

In some embodiments, the cGAS polypeptide is a polypeptide that has 40% to 99%, 45% to 99%, 50% to 99%, 55% to 99%, 60% to 99%, 65% to 99%, 70% to 99%, 75% to 99%, 80% to 99%, 85% to 99%, 90% to 99% or, 95% to 99% sequence identity with a wild type cGAS amino acid sequence. In some embodiments, the cGAS polypeptide is a polypeptide that has 40% to 50%, 50% to 60%, 60% to 70%, 70% to 80%, 80% to 90%, or 90 to 99% sequence identity with a wild type cGAS amino acid sequence. In some embodiments, the cGAS polypeptide is a polypeptide that has 40% or more, 45% or more, 50% or more, 55% or more, 60% or more, 70% or more, 75% or more, 80% or more, 85% or more, 90% or more, 95% or more or 99% or more sequence identity with a wild type cGAS amino acid sequence.

Such polypeptides may optionally be fused to a polypeptide domain that increases solubility of the product. The domain may be linked to the polypeptide through a defined protease cleavage site, e.g., a TEV sequence, which is cleaved by TEV protease. The linker may also include one or more flexible sequences, e.g., from 1 to 10 glycine residues. In some embodiments, the cleavage of the fusion protein is performed in a buffer that maintains solubility of the product, e.g., in the presence of from 0.5 to 2 M urea, in the presence of polypeptides and/or polynucleotides that increase solubility, and the like. Domains of interest include endosomolytic domains, e.g., influenza HA domain; and other polypeptides that aid in production, e.g., IF2 domain, GST domain, GRPE domain, and the like. The polypeptide may be formulated for improved stability. For example, the peptides may be PEGylated, where the polyethyleneoxy group provides for enhanced lifetime in the blood stream.

Additionally or alternatively, the cyclic-di-nucleotide active agent(s) may be fused to a polypeptide permeant domain to promote uptake by the cell. A number of permeant domains are known in the art and may be used in the non-integrating polypeptides of the present invention, including peptides, peptidomimetics, and non-peptide carriers. For example, a permeant peptide may be derived from the third alpha helix of Drosophila melanogaster transcription factor Antennapedia, referred to as penetratin, which comprises the amino acid sequence RQIKIWFQNRRMKWKK (SEQ ID NO:03). As another example, the permeant peptide comprises the HIV-1 tat basic region amino acid sequence, which may include, for example, amino acids 49-57 of naturally-occurring tat protein. Other permeant domains include poly-arginine motifs, for example, the region of amino acids 34-56 of HIV-1 rev protein, nona-arginine, octa-arginine, and the like. (See, for example, Futaki et al. Curr Protein Pept Sci. 4(2): 87-96 (2003); and Wender et al. Proc. Natl. Acad. Sci. U.S.A 97(24):13003-8 (2000); published U.S. Patent applications 20030220334; 20030083256; 20030032593; and 20030022831, herein specifically incorporated by reference for the teachings of translocation peptides and peptoids). The nona-arginine (R9) sequence is one of the more efficient PTDs that have been characterized (Wender et al. 2000; Uemura et al. 2002). The site at which the fusion is made may be selected in order to optimize the biological activity, secretion or binding characteristics of the polypeptide. The optimal site will be determined by routine experimentation.

In practicing embodiments of the methods provided herein, an effective amount of the active agent, i.e., a cyclic-di-nucleotide active agent (such as described above), is provided in the target cell or cells. As used herein "effective amount" or "efficacious amount" means the amount of the active agent that, when contacted with the cell, e.g., by being introduced into the cell in vitro, by being administered to a subject, etc., is sufficient to result in increased levels of a cyclic-di-nucleotide in the cell. The "effective amount" will vary depending on cell and/or the organism and/or compound and or the nature of the desired outcome and/or the disease and its severity and the age, weight, etc., of the subject to be treated.

In some instances, the effective amount of the active agent is provided in the cell by contacting the cell with the active agent. Contact of the cell with the active agent may occur using any convenient protocol. The protocol may provide for in vitro or in vivo contact of the active agent with the target cell, depending on the location of the target cell. For example, where the target cell is an isolated cell, e.g., a cell in vitro (i.e., in culture), or a cell ex vivo ("ex vivo" being cells or organs are modified outside of the body, where such cells or organs are typically returned to a living body), the active agent may be introduced directly into the cell under cell culture conditions permissive of viability of the target cell. Such techniques include, but are not necessarily limited to: viral infection, transfection, conjugation, protoplast fusion, electroporation, particle gun technology, calcium phosphate precipitation, direct microinjection, viral vector delivery, and the like. The choice of method is generally dependent on the type of cell being contacted and the nature of the active agent, and the circumstances under which the transformation is taking place (e.g., in vitro, ex vivo, or in vivo). A general discussion of these methods can be found in Ausubel, et al, Short Protocols in Molecular Biology, 3rd ed., Wiley & Sons, 1995. As another example, where the target cell or cells are part of a multicellular organism, the active agent may be administered to the organism or subject in a manner such that the agent is able to contact the target cell(s), e.g., via an in vivo protocol. By "in vivo," it is meant in the target construct is administered to a living body of an animal.

In some embodiments, the cyclic-di-nucleotide active agent is employed to modulate c-di-AMP activity in mitotic or post-mitotic cells in vitro or ex vivo, i.e., to produce modified cells that can be reintroduced into an individual. Mitotic and post-mitotic cells of interest in these embodiments include any eukaryotic cell, e.g., pluripotent stem cells, for example, ES cells, iPS cells, and embryonic germ cells; somatic cells, for example, hematopoietic cells, fibroblasts, neurons, muscle cells, bone cells, vascular endothelial cells, gut cells, and the like, and their lineage-restricted progenitors and precursors; and neoplastic, or cancer, cells, i.e., cells demonstrating one or more properties associated with cancer cells, e.g., hyperproliferation, contact inhibition, the ability to invade other tissue, etc. In certain embodiments, the eukaryotic cells are cancer cells. In certain embodiments, the eukaryotic cells are hematopoietic cells, e.g., macrophages, NK cells, etc. Cells may be from any mammalian species, e.g., murine, rodent, canine, feline, equine, bovine, ovine, primate, human, etc. Cells may be from established cell lines or they may be primary cells, where "primary cells", "primary cell lines", and "primary cultures" are used interchangeably herein to refer to cells and cells cultures that have been derived from a subject and allowed to grow in vitro for a limited number of passages, i.e., splittings, of the culture. For example, primary cultures are cultures that may have been passaged 0 times, 1 time, 2 times, 4 times, 5 times, 10 times, or 15 times, but not enough times go through the crisis stage. Typically, the primary cell lines of the present invention are maintained for fewer than 10 passages in vitro.

If the cells are primary cells, they may be harvested from an individual by any convenient method. For example, blood cells, e.g., leukocytes, e.g., macrophages, may be harvested by apheresis, leukocytapheresis, density gradient separation, etc., while cells from tissues such as skin, muscle, bone marrow, spleen, liver, pancreas, lung, intestine, stomach, etc. may be harvested by biopsy. An appropriate solution may be used for dispersion or suspension of the harvested cells. Such solution will generally be a balanced salt solution, e.g., normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc. The cells may be used immediately, or they may be stored, frozen, for long periods of time, being thawed and capable of being reused. In such cases, the cells may be frozen in 10% DMSO, 50% serum, 40% buffered medium, or some other such solution as is commonly used in the art to preserve cells at such freezing temperatures, and thawed in a manner as commonly known in the art for thawing frozen cultured cells.

The cyclic-di-nucleotide active agent(s) may be produced by eukaryotic cells or by prokaryotic cells, it may be further processed by unfolding, e.g., heat denaturation, DTT reduction, etc. and may be further refolded, using methods known in the art.

Modifications of interest that do not alter primary sequence include chemical derivatization of polypeptides, e.g., acylation, acetylation, carboxylation, amidation, etc. Also included are modifications of glycosylation, e.g., those made by modifying the glycosylation patterns of a polypeptide during its synthesis and processing or in further processing steps; e.g., by exposing the polypeptide to enzymes which affect glycosylation, such as mammalian glycosylating or deglycosylating enzymes. Also embraced are sequences that have phosphorylated amino acid residues, e.g., phosphotyrosine, phosphoserine, or phosphothreonine.

Also included in the subject invention are cyclic-di-nucleotide active agent polypeptides (e.g., cGAS polypeptides) that have been modified using ordinary molecular biological techniques and synthetic chemistry so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. D-amino acids may be substituted for some or all of the amino acid residues.

The cyclic-di-nucleotide active agent (s) may be prepared by in vitro synthesis, using any suitable method. Various commercial synthetic apparatuses are available, for example, automated synthesizers by Applied Biosystems, Inc., Beckman, etc. By using synthesizers, naturally occurring amino acids may be substituted with unnatural amino acids. The particular sequence and the manner of preparation will be determined by convenience, economics, purity required, and the like.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

The cyclic-di-nucleotide active agent(s) may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will include 20% or more by weight of the desired product, such as 75% or more by weight of the desired product, including 95% or more by weight of the desired product, and for therapeutic purposes, may be 99.5% or more by weight, in relation to contaminants related to the method of preparation of the product and its purification (where the percentages may be based upon total protein).

To modulate cyclic-di-nucleotide activity and/or production, the cyclic-di-nucleotide active agent(s)—be they small molecules (e.g., 2'-5' phosphodiester linkage containing cyclic-di-nucleotides) polypeptides or nucleic acids that encode cyclic-di-nucleotide active agent polypeptides (e.g., cGAS)—may be provided to the cells for a sufficient period of time, e.g., from 30 minutes to 24 hours, e.g., 1 hour, 1.5 hours, 2 hours, 2.5 hours, 3 hours, 3.5 hours 4 hours, 5 hours, 6 hours, 7 hours, 8 hours, 12 hours, 16 hours, 18 hours, 20 hours, or any other period from 30 minutes to 24 hours, which may be repeated with a frequency of every day to every 4 days, e.g., every 1.5 days, every 2 days, every 3 days, or any other frequency from about every day to about every four days. The agent(s) may be provided to the subject cells one or more times, e.g., one time, twice, three times, or more than three times, and the cells allowed to incubate with the agent(s) for some amount of time following each contacting event e.g., 16-24 hours, after which time the media is replaced with fresh media and the cells are cultured further.

In certain embodiments, two or more, three or more, four or more, five or more, six or more, seven or more, eight or more, nine or more, or ten or more different cyclic-di-nucleotide active agents are provided to a cell in a manner sufficient to increase production of a type I interferon by the cell. In some instances, the active agents include two or more different 2'-5' phosphodiester linkage comprising cyclic-di-nucleotides. In certain embodiments, the active agents include a 2'-5' phosphodiester linkage containing cyclic-di-nucleotide and a nucleic acid encoding cGAS or a cGAS polypeptide. In instances in which two or more different cyclic-di-nucleotide active agents are provided to the cell, i.e., a cyclic-di-nucleotide active agent cocktail, the cyclic-di-nucleotide active agent(s) may be provided simultaneously, e.g., as two cyclic-di-nucleotides delivered simultaneously or a cyclic-di-nucleotide and a vector containing a nucleic acid encoding cGAS delivered simultaneously. Alternatively, they may be provided consecutively, e.g., the first cyclic-di-nucleotide active agent being provided first, followed by the cyclic-di-nucleotide active agent, etc. or vice versa.

An effective amount of cyclic-di-nucleotide active agent(s) are provided to the cells to result in a change in cyclic-di-nucleotide levels. An effective amount of cyclic-di-nucleotide active agent is the amount to result in a 2-fold increase or more in the amount of cyclic-di-nucleotide production observed relative to a negative control, e.g., a cell contacted with an empty vector or irrelevant polypeptide. That is to say, an effective amount or dose of a cyclic-di-nucleotide active agent will result in a 2-fold increase, a 3-fold increase, a 4-fold increase or more in the amount of cyclic-di-nucleotide observed, in some instances a 5-fold increase, a 6-fold increase or more, sometimes a 7-fold or 8-fold increase or more in the amount of activity observed, e.g., an increase of 10-fold, 50-fold, or 100-fold or more, in some instances, an increase of 200-fold, 500-fold, 700-fold, or 1000-fold or more, in the amount of activity observed. The amount of activity may be measured by any suitable method. For example, the amount of interferon produced by the cell may be assessed after contact with the cyclic-di-nucleotide active agent(s), e.g., 2 hours, 4 hours, 8 hours, 12 hours, 24 hours, 36 hours, 48 hours, 72 hours or more after contact with the cyclic-di-nucleotide active agent(s).

Contacting the cells with the cyclic-di-nucleotide active agent(s) may occur in any culture media and under any culture conditions that promote the survival of the cells. For example, cells may be suspended in any appropriate nutrient medium that is convenient, such as Iscove's modified DMEM or RPMI 1640, supplemented with fetal calf serum or heat inactivated goat serum (about 5-10%), L-glutamine, a thiol, particularly 2-mercaptoethanol, and antibiotics, e.g., penicillin and streptomycin. The culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors.

Following the methods described above, a cell may be modified ex vivo to have an increase in cyclic-di-nucleotide levels. In some embodiments, it may be desirous to select for the modified cell, e.g., to create an enriched population of modified cells. Any convenient modification to the cells that marks the cells as modified with a cyclic-di-nucleotide active agent may be used. For example, a selectable marker may be inserted into the genome of the cell, so that the population of cells may be enriched for those comprising the genetic modification by separating the genetically marked cells from the remaining population. Separation may be by any convenient separation technique appropriate for the selectable marker used. For example, if a fluorescent marker has been inserted, cells may be separated by fluorescence activated cell sorting, whereas if a cell surface marker has been inserted, cells may be separated from the heterogeneous population by affinity separation techniques, e.g., magnetic separation, affinity chromatography, "panning" with an affinity reagent attached to a solid matrix, or other convenient technique. Techniques providing accurate separation include fluorescence activated cell sorters, which can have varying degrees of sophistication, such as multiple color channels, low angle and obtuse light scattering detecting channels, impedance channels, etc. The cells may be selected against dead cells by employing dyes associated with dead cells (e.g., propidium iodide). Any technique may be employed which is not unduly detrimental to the viability of the genetically modified cells.

Cell compositions that are highly enriched for cells comprising cyclic-di-nucleotide active agent(s) are achieved in this manner. By "highly enriched", it is meant that the genetically modified cells will be 70% or more, 75% or more, 80% or more, 85% or more, 90% or more of the cell composition, for example, about 95% or more, or 98% or more of the cell composition. In other words, the composition may be a substantially pure composition of cells comprising cyclic-di-nucleotide active agent(s).

Cells comprising cyclic-di-nucleotide active agent(s) produced by the methods described herein may be used immediately. Alternatively, the cells may be frozen at liquid nitrogen temperatures and stored for long periods of time, being thawed and capable of being reused. In such cases, the cells may be frozen in 10% DMSO, 50% serum, 40% buffered medium, or some other such solution as is commonly used in the art to preserve cells at such freezing temperatures, and thawed in a manner as commonly known in the art for thawing frozen cultured cells.

The cells comprising cyclic-di-nucleotide active agent(s) may be cultured in vitro under various culture conditions. The cells may be expanded in culture, i.e., grown under conditions that promote their proliferation. Culture medium may be liquid or semi-solid, e.g., containing agar, methylcellulose, etc. The cell population may be suspended in an appropriate nutrient medium, such as Iscove's modified DMEM or RPMI 1640, normally supplemented with fetal calf serum (about 5-10%), L-glutamine, a thiol, particularly 2-mercaptoethanol, and antibiotics, e.g., penicillin and streptomycin. The culture may contain growth factors to which the regulatory T cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors.

Cells that have been modified with cyclic-di-nucleotide active agent(s) may be transplanted to a subject to treat a disease or as an antiviral, antipathogenic, or anticancer therapeutic or for biological research. The subject may be a neonate, a juvenile, or an adult. Of particular interest are mammalian subjects. Mammalian species that may be treated with the present methods include canines and felines; equines; bovines; ovines; etc. and primates, particularly humans. Animal models, particularly small mammals, e.g., murine, lagomorpha, etc., may be used for experimental investigations.

Cells may be provided to the subject alone or with a suitable substrate or matrix, e.g., to support their growth and/or organization in the tissue to which they are being transplanted. In some instances, at least $1 \times 10^3$ cells will be administered, for example $5 \times 10^3$ cells, $1 \times 10^4$ cells, $5 \times 10^4$ cells, $1 \times 10^5$ cells, $1 \times 10^6$ cells or more. The cells may be introduced to the subject via any of the following routes: parenteral, subcutaneous, intravenous, intracranial, intraspinal, intraocular, or into spinal fluid. The cells may be introduced by injection, catheter, or the like. Examples of methods for local delivery, that is, delivery to the site of injury, include, e.g., through an Ommaya reservoir, e.g., for intrathecal delivery (see, e.g., U.S. Pat. Nos. 5,222,982 and 5,385,582, incorporated herein by reference); by bolus injection, e.g., by a syringe, e.g., into a joint; by continuous infusion, e.g., by cannulation, e.g., with convection (see e.g., US Application No. 20070254842, incorporated here by reference); or by implanting a device upon which the cells have been reversibly affixed (see e.g., US Application Nos. 20080081064 and 20090196903, incorporated herein by reference).

In other aspects of the invention, the cyclic-di-nucleotide active agent(s) are employed to increase the production of type I interferon in vivo. In these in vivo embodiments, the cyclic-di-nucleotide active agent(s) are administered directly to the individual. In some embodiments, the cyclic-di-nucleotide active agent administered to the subject contains a 2'-5' phosphodiester linkage containing cyclic-di-nucleotide.

Cyclic-di-nucleotide active agent(s) may be administered by any suitable methods for the administration of peptides, small molecules and nucleic acids to a subject. The cyclic-di-nucleotide active agent(s) can be incorporated into a variety of formulations. More particularly, the cyclic-di-nucleotide active agent(s) of the present invention can be formulated into pharmaceutical compositions by combination with appropriate pharmaceutically acceptable carriers or diluents. Pharmaceutical compositions that can be used in practicing the subject methods are described below.

In such instances, an effective amount of the cyclic-di-nucleotide active agent is administered to the subject. By an "effective amount" or a "therapeutically effective amount" of the cyclic-di-nucleotide active agent it is meant an amount that is required to reduce the severity, the duration and/or the symptoms of the disease. In some embodiments, the effective amount of a pharmaceutical composition containing a cyclic-di-nucleotide active agent, as provided herein, is between 0.025 mg/kg and 1000 mg/kg body weight of a human subject. In certain embodiments, the pharmaceutical composition is administered to a human subject at an amount of 1000 mg/kg body weight or less, 950 mg/kg body weight or less, 900 mg/kg body weight or less, 850 mg/kg body weight or less, 800 mg/kg body weight or less, 750 mg/kg body weight or less, 700 mg/kg body weight or less, 650 mg/kg body weight or less, 600 mg/kg body weight or less, 550 mg/kg body weight or less, 500 mg/kg body weight or less, 450 mg/kg body weight or less, 400 mg/kg body weight or less, 350 mg/kg body weight or less, 300 mg/kg body weight or less, 250 mg/kg body weight or less, 200 mg/kg body weight or less, 150 mg/kg body weight or less, 100 mg/kg body weight or less, 95 mg/kg body weight or less, 90 mg/kg body weight or less, 85 mg/kg body weight or less, 80 mg/kg body weight or less, 75 mg/kg body weight or less, 70 mg/kg body weight or less, or 65 mg/kg body weight or less.

In another aspect, provided herein is a method for increasing a stimulator of interferon genes (STING) mediated response in a subject, e.g., a STING mediated immune response. In certain embodiments, the method includes the step of administering to the subject an amount of a STING active agent effective to increase a STING mediated response in the subject. A "STING" mediated response refers to any response that is mediated by STING, including, but not limited to, immune responses to bacterial pathogens, viral pathogens, and eukaryotic pathogens. See, e.g., Ishikawa et al. *Immunity* 29: 538-550 (2008); Ishikawa et al. *Nature* 461: 788-792 (2009); and Sharma et al. *Immunity* 35: 194-207 (2011). STING also functions in certain autoimmune diseases initiated by inappropriate recognition of self DNA (see, e.g., Gall et al. *Immunity* 36: 120-131 (2012), as well as for the induction of adaptive immunity in response to DNA vaccines (see, e.g., Ishikawa et al. *Nature* 461: 788-792 (2009). By increasing a STING mediated response in a subject is meant an increase in a STING mediated response in a subject as compared to a control subject (e.g., a subject who is not administered a STING active agent). In certain embodiments, the method is for increasing a stimulator of interferon genes (STING) mediated response in a subject, wherein the STING mediated response is non-responsive to a cyclic-di-nucleotide having two 3'-5' phosphodiester bonds (i.e., a canonical cyclic dinucleotide).

As described in the Experimental Section below, cyclic-di-nucleotides having 2'-5' phosphodiester bonds have been shown to activate STING signaling. Moreover, such cyclic-di-nucleotides having 2'-5' phosphodiester bonds have been shown to stimulate alleles of STING that are non-responsive to cyclic-di-nucleotides that have two phosphodiester bonds. As such, in some embodiments, the STING active agent is a cyclic-di-nucleotide active agent described herein (e.g., cyclic-di-nucleotide, nucleic acid encoding cGAS).

In other embodiments the STING active agent is a nucleic acid encoding STING or a STING polypeptide. Nucleic acids encoding various STINGs include, but are not limited to, those described in: Nitta et al. *Hepatology* 57(1): 46-58 (2013) and Jin et al. *J. Immunol.* 190(6): 2835-2843 (2013) and those deposited in GENBANK and assigned deposit numbers: NM_198282.2 and NP_938023.1 (human); NM_028261.1 and NP_082537.1 (*Mus musculus*); and NM_057386.4 and NP_476734.1 (*Drosophila melanogaster*).

In certain embodiments, the nucleic acid encoding STING has the following sequence:

(SEQ ID NO: 04)
gttcattttcactcctcctcctaggtcacacttttcagaaaaagaatc tgcatcctggaaaccagaagaaaatatgagacggggaatcatcgtgtga tgtgtgtgctgcctttggctgagtgtgtggagtcctgctcaggtgttagg tacagtgtgtttgatcgtggtggcttgagggaaccgctgttcagagct gtgactgcggctgcactcagagaagctgcccttggctgctcgtagcgccg ggccttctctcctcgtcatcatccagagcagccagtgtccgggaggcaga agatgccccactccagcctgcatccatccatcccgtgtcccagggtcac ggggcccagaaggcagccttggttctgctgagtgcctgcctggtgaccct ttgggggctaggagagccaccagagcacactctccggtacctggtgctcc acctagcctccctgcagctgggactgctgttaaacggggtctgcagcctg gctgaggagctgcgccacatccactccaggtaccggggcagctactggag -continued
gactgtgcgggcctgcctgggctgccccctccgccgtggggccctgttgc tgctgtccatctatttctactactccctcccaaatgcggtcggcccgccc ttcacttggatgcttgccctcctgggcctctcgcaggcactgaacatcct cctgggcctcaagggcctggccccagctgagatctctgcagtgtgtgaaa aagggaattcaacgtggcccatgggctggcatggtcatattacatcgga tatctgcggctgatcctgccagagctccaggcccggattcgaacttacaa tcagcattacaacaacctgctacggggtgcagtgagccagcggctgtata ttctcctcccattggactgtggggtgcctgataacctgagtatggctgac cccaacattcgcttcctggataaactgcccagcagaccggtgaccatgc tggcatcaaggatcgggtttacagcaacagcatctatgagcttctggaga acgggcagcgggcgggcacctgtgtcctggagtacgccacccccttgcag actttgtttgccatgtcacaatacagtcaagctggctttagccgggagga taggcttgagcaggccaaactcttctgccggacacttgaggacatcctgg cagatgcccctgagtctcagaacaactgccgcctcattgcctaccaggaa cctgcagatgacagcagcttctcgctgtcccaggaggttctccggcacct gcggcaggaggaaaaggaagaggttactgtgggcagcttgaagacctcag cggtgcccagtacctccacgatgtcccaagagcctgagctcctcatcagt ggaatggaaaagccctccctctccgcacggatttctcttgagacccagg gtcaccaggccagagcctccagtggtctccaagcctctggactgggggct ctcttcagtggctgaatgtccagcagagctatttccttccacaggggcc ttgcagggaagggtccaggacttgacatcttaagatgcgtcttgtccct tgggccagtcatttccctctctgagcctcggtgtcttcaacctgtgaaa tgggatcataatcactgccttacctccctcacggttgttgtgaggactga gtgtgtggaagttttttcataaactttggatgctagtgtacttagggggtg tgccaggtgtctttcatgggcttccagacccactcccacccttctcc ccttccttttgcccggggacgccgaactctctcaatggtatcaacaggctc cttcgccctctggctcctggtcatgttccattattggggagcccagcag aagaatggagaggaggaggaggctgagtttggggtattgaatccccggc tcccacctgcagcatcaaggttgctatggactctcctgccgggcaactc ttgcgtaatcatgactatctctaggattctggcaccacttccttccctgg cccttaagcctagctgtgtatcggcaccccacccactagagtactcc ctctcacttgcggtttcctttatactccacccctttctcaacggtccttt ttaaagcacatctcagattacccaaaaaaaaaaaaaaaaaa.

In some embodiments, the nucleic acid encoding STING is a nucleic acid with 40% to 99%, 45% to 99%, 50% to 99%, 55% to 99%, 60% to 99%, 65% to 99%, 70% to 99%, 75% to 99%, 80% to 99%, 85% to 99%, 90% to 99% or, 95% to 99% sequence identity with a wild type STING nucleic acid sequence. In some embodiments, the nucleic acid encoding STING is a nucleic acid with 40% to 50%, 50% to 60%, 60% to 70%, 70% to 80%, 80% to 90%, or 90 to 99% sequence identity with a wild type STING nucleic acid sequence. In some embodiments, the nucleic acid encoding STING is a nucleic acid with 40% or more, 45% or more, 50% or more, 55% or more, 60% or more, 70% or more, 75% or more, 80% or more, 85% or more, 90% or more, 95% or more or 99% or more sequence identity with a wild type STING nucleic acid sequence.

Amino acid sequences of STING include, but are not limited to, those described in: Nitta et al. *Hepatology* 57(1): 46-58 (2013) and Jin et al. *J. Immunol.* 190(6): 2835-2843 (2013) and those deposited in GENBANK and assigned deposit numbers: NM_198282.2 and NP_938023.1 (human); NM_028261.1 and NP_082537.1 (*Mus musculus*); and NM_057386.4 and NP_476734.1 (*Drosophila melanogaster*).

In certain embodiments, the STING polypeptide has the following sequence:

(SEQ ID NO: 05)
MPHSSLHPSIPCPRGHGAQKAALVLLSACLVTLWGLGEPPEHTLRYLVLH

LASLQLGLLLNGVCSLAEELRHIHSRYRGSYWRTVRACLGCPLRRGALLL

LSIYFYYSLPNAVGPPFTWMLALLGLSQALNILLGLKGLAPAEISAVCEK

GNFNVAHGLAWSYYIGYLRLILPELQARIRTYNQHYNNLLRGAVSQRLYI

LLPLDCGVPDNLSMADPNIRFLDKLPQQTGDHAGIKDRVYSNSIYELLEN

GQRAGTCVLEYATPLQTLFAMSQYSQAGFSREDRLEQAKLFCRTLEDILA

DAPESQNNCRLIAYQEPADDSSFSLSQEVLRHLRQEEKEEVTVGSLKTSA

VPSTSTMSQEPELLISGMEKPLPLRTDFS.

In other embodiments, the STING polypeptide has the following sequence:

(SEQ ID NO: 06)
MPHSSLHPSIPCPRGHGAQKAALVLLSACLVTLWGLGEPPEHTLRYLVLH

LASLQLGLLLNGVCSLAEELHHIHSRYRGSYWRTVRACLGCPLRRGALLL

LSIYFYYSLPNAVGPPFTWMLALLGLSQALNILLGLKGLAPAEISAVCEK

GNFNVAHGLAWSYYIGYLRLILPELQARIRTYNQHYNNLLRGAVSQRLYI

LLPLDCGVPDNLSMADPNIRFLDKLPQQTADRAGIKDRVYSNSIYELLEN

GQRAGTCVLEYATPLQTLFAMSQYSQAGFSREDRLEQAKLFCQTLEDILA

DAPESQNNCRLIAYQEPADDSSFSLSQEVLRHLRQEEKEEVTVGSLKTSA

VPSTSTMSQEPELLISGMEKPLPLRTDFS.

In some embodiments, the STING polypeptide is a polypeptide that has 40% to 99%, 45% to 99%, 50% to 99%, 55% to 99%, 60% to 99%, 65% to 99%, 70% to 99%, 75% to 99%, 80% to 99%, 85% to 99%, 90% to 99% or, 95% to 99% sequence identity with a wild type STING amino acid sequence. In some embodiments, the cGAS polypeptide is a polypeptide that has 40% to 50%, 50% to 60%, 60% to 70%, 70% to 80%, 80% to 90%, or 90 to 99% sequence identity with a wild type STING amino acid sequence. In some embodiments, the STING polypeptide is a polypeptide that has 40% or more, 45% or more, 50% or more, 55% or more, 60% or more, 70% or more, 75% or more, 80% or more, 85% or more, 90% or more, 95% or more or 99% or more sequence identity with a wild type STING amino acid sequence.

The above methods find use in a variety of different applications. Certain applications are now reviewed in the following Utility section.

Utility

The methods and compositions provided herein find use in a variety of applications, where such applications include increasing type I interferon (e.g., interferon-β) in a subject is desired. In addition, the methods and compositions provided herein find use in a variety of applications, where such applications include increasing STING mediated response in a subject is desired. Specific applications of interest include those in which a subject is treated for a disease condition that would benefit from an increase in type I interferon by providing the subject with a therapeutically effective amount of a cyclic-di-nucleotide active agent. In some instances, it may be desirable to increase a type I interferon or STING mediated response in a healthy individual, e.g., for the prevention of a disease or condition. As such, in some embodiments, the methods and compositions provided herein can be used to produce an 'adjuvant' effect in a vaccine to prevent an infection or other disease, wherein the active agent stimulates immunological memory to protect against future disease or infection.

In some embodiments, subjects suitable for treatment with a method described herein include individuals having an immunological or inflammatory disease or disorder including, but not limited to a cancer, an autoimmune disease or disorder, an allergic reaction, a chronic infectious disease and an immunodeficiency disease or disorder.

In some embodiments, subjects suitable for treatment with a method of the present invention include individuals having a cellular proliferative disease, such as a neoplastic disease (e.g., cancer). Cellular proliferative disease is characterized by the undesired propagation of cells, including, but not limited to, neoplastic disease conditions, e.g., cancer. Examples of cellular proliferative disease include, but not limited to, abnormal stimulation of endothelial cells (e.g., atherosclerosis), solid tumors and tumor metastasis, benign tumors, for example, hemangiomas, acoustic neuromas, neurofibromas, trachomas, and pyogenic granulomas, vascular malfunctions, abnormal wound healing, inflammatory and immune disorders, Bechet's disease, gout or gouty arthritis, abnormal angiogenesis accompanying, for example, rheumatoid arthritis, psoriasis, diabetic retinopathy, other ocular angiogenic diseases such as retinopathy of prematurity (retrolental fibroblastic), macular degeneration, corneal graft rejection, neurovascular glaucoma and Oster Webber syndrome, psoriasis, restenosis, fungal, parasitic and viral infections such cytomegaloviral infections. Subjects to be treated according to the methods of the invention include any individual having any of the above-mentioned disorders.

In other embodiments, subjects suitable for treatment with a subject method include individuals who have been clinically diagnosed as infected with a virus. In some embodiments, the virus is a hepatitis virus (e.g., HAV, HBV, HCV, delta, etc.), particularly HCV, are suitable for treatment with the methods of the instant invention. Individuals who are infected with HCV are identified as having HCV RNA in their blood, and/or having anti-HCV antibody in their serum. Such individuals include naïve individuals (e.g., individuals not previously treated for HCV, particularly those who have not previously received IFN-α-based or ribavirin-based therapy) and individuals who have failed prior treatment for HCV.

In some embodiments, subjects suitable for treatment with a method provided herein include an individual with a neurodegenerative disease or disorder, including, but not limited to, Parkinson's disease, Alzheimer's disease, Huntington's disease, and Amyotrophic lateral sclerosis (ALS).

In other embodiments, subjects suitable for treatment with a method of the present invention include individuals having multiple sclerosis. Multiple sclerosis refers to an autoimmune neurodegenerative disease, which is marked by inflammation within the central nervous system with lymphocyte attack against myelin produced by oligodendrocytes, plaque formation and demyelization with destruction of the myelin sheath of axons in the brain and spinal cord, leading to significant neurological disability over time. Typically, at onset an otherwise healthy person presents with the acute or sub acute onset of neurological symptomatology (attack) manifested by unilateral loss of vision, vertigo, ataxia, dyscoordination, gait difficulties, sensory impairment characterized by paresthesia, dysesthesia, sensory loss, urinary disturbances until incontinence, diplopia, dysarthria or various degrees of motor weakness until paralysis. The symptoms may be painless, remain for several days to a few weeks, and then partially or completely resolve. After a period of remission, a second attack will occur. During this period after the first attack, the patient is defined to suffer from probable MS. Probable MS patients may remain undiagnosed for years. When the second attack occurs the diagnosis of clinically definite MS (CDMS) is made (Poser criteria 1983; C. M. Poser et al., Ann. Neurol. 1983; 13, 227).

The terms "subject" and "patient" mean a member or members of any mammalian or non-mammalian species that may have a need for the pharmaceutical methods, compositions and treatments described herein. Subjects and patients thus include, without limitation, primate (including humans), canine, feline, ungulate (e.g., equine, bovine, swine (e.g., pig)), avian, and other subjects. Humans and non-human animals having commercial importance (e.g., livestock and domesticated animals) are of particular interest.

"Mammal" means a member or members of any mammalian species, and includes, by way of example, canines; felines; equines; bovines; ovines; rodentia, etc. and primates, particularly humans. Non-human animal models, particularly mammals, e.g., primate, murine, lagomorpha, etc. may be used for experimental investigations.

"Treating" or "treatment" of a condition or disease includes: (1) preventing at least one symptom of the conditions, i.e., causing a clinical symptom to not significantly develop in a mammal that may be exposed to or predisposed to the disease but does not yet experience or display symptoms of the disease, (2) inhibiting the disease, i.e., arresting or reducing the development of the disease or its symptoms, or (3) relieving the disease, i.e., causing regression of the disease or its clinical symptoms. As used herein, the term "treating" is thus used to refer to both prevention of disease, and treatment of pre-existing conditions. For example, where the cyclic-di-nucleotide active agent is administered, the prevention of cellular proliferation can be accomplished by administration of the subject compounds prior to development of overt disease, e.g., to prevent the regrowth of tumors, prevent metastatic growth, etc. Alternatively the compounds are used to treat ongoing disease, by stabilizing or improving the clinical symptoms of the patient.

Combination Therapy

For use in the subject methods, the cyclic-di-nucleotide active agent described herein may be administered in combination with other pharmaceutically active agents, including other agents that treat the underlying condition or a symptom of the condition. "In combination with" as used herein refers to uses where, for example, the first compound is administered during the entire course of administration of the second compound; where the first compound is administered for a period of time that is overlapping with the administration of the second compound, e.g., where administration of the first compound begins before the administration of the second compound and the administration of the first compound ends before the administration of the second compound ends; where the administration of the second compound begins before the administration of the first compound and the administration of the second compound ends before the administration of the first compound ends; where the administration of the first compound begins before administration of the second compound begins and the administration of the second compound ends before the administration of the first compound ends; where the administration of the second compound begins before administration of the first compound begins and the administration of the first compound ends before the administration of the second compound ends. As such, "in combination" can also refer to regimen involving administration of two or more compounds. "In combination with" as used herein also refers to administration of two or more compounds that may be administered in the same or different formulations, by the same of different routes, and in the same or different dosage form type.

Examples of other agents for use in combination therapy of neoplastic disease include, but are not limited to, thalidomide, marimastat, COL-3, BMS-275291, squalamine, 2-ME, SU6668, neovastat, Medi-522, EMD121974, CAI, celecoxib, interleukin-12, IM862, TNP470, avastin, gleevec, herceptin, and mixtures thereof. Examples of chemotherapeutic agents for use in combination therapy include, but are not limited to, daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphor-amide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES).

Other antiviral agents can also be delivered in the treatment methods of the invention. For example, compounds that inhibit inosine monophosphate dehydrogenase (IM-PDH) may have the potential to exert direct anti viral activity, and such compounds can be administered in combination with the mutant Listeria, as described herein. Drugs that are effective inhibitors of hepatitis C NS3 protease may be administered in combination with the mutant Listeria, as described herein. Hepatitis C NS3 protease inhibitors inhibit viral replication. Other agents such as inhibitors of HCV NS3 helicase are also attractive drugs for combinational therapy, and are contemplated for use in combination therapies described herein. Ribozymes such as Heptazyme™ and phosphorothioate oligonucleotides which are complementary to HCV protein sequences and which inhibit the expression of viral core proteins are also suitable for use in combination therapies described herein. Examples of other agents for use in combination therapy of multiple sclerosis include, but are not limited to; glatiramer; corticosteroids; muscle relaxants, such as Tizanidine (Zanaflex) and baclofen (Lioresal); medications to reduce fatigue, such as amantadine (Symmetrel) or modafinil (Provigil); and other medications that may also be used for depression, pain and bladder or bowel control problems that can be associated with MS.

In the context of a combination therapy, combination therapy compounds may be administered by the same route of administration (e.g., intrapulmonary, oral, enteral, etc.) that the cyclic-di-nucleotide active agents are administered. In the alternative, the compounds for use in combination therapy with the cyclic-di-nucleotide active agent may be administered by a different route of administration.

Adjuvants

In certain embodiments, the cyclic di-nucleotide active agent functions as an adjuvant when administered together with a drug or vaccine to treat or prevent a disease or condition, including, but not limited to, those diseases and conditions provided herein. In some embodiments, the cyclic di-nucleotide active agents are administered together with a vaccine. Such active agents that are administered with a vaccine can function as an adjuvant to enhance the immune response elicited by the vaccine, including stimulating immunological memory to protect against future diseases and/or infections.

In certain embodiments, the cyclic di-nucleotide or STING active agents administered as an adjuvant for a vaccine can enhance the effectiveness of the vaccine by, e.g., increasing the immunogenicity of weaker antigens, reducing the amount of antigen required to elicit a immune response, reducing the frequency of immunization necessary to maintain protective immunity, enhance the efficacy of vaccines in immunocompromised or other individuals with reduced immune responses, and/or increase immunity at a target tissue, such as mucosal immunity. In such embodiments, the cyclic di-nucleotide active agents, when co-administered with one or more antigens, can induce a particular cytokine profile to promote cellular and humoral immunity against the antigen and increase the effectiveness of vaccination.

Antigens used to prepare vaccines may be derived from a variety of microorganisms such as viruses, bacteria and parasites that contain substances that are not normally present in the body, as well as tumor cells. These substances can be used as antigens to produce an immune response to destroy both the antigen and cells containing the antigen, such as a bacterial cell or cancer cell. In certain instances, isolated or crude antigens of microbial pathogens can be used in vaccines to treat infectious disease; isolated or crude tumor cell antigens can be used in vaccines to treat cancer; isolated or crude antigens known to be associated with a pathologically aberrant cell can be used to treat a variety of diseases in which it is beneficial to target particular cells for destruction.

Microorganisms that may be a source of antigen include clinically relevant microorganisms, such as bacteria, including pathogenic bacteria; viruses (e.g., Influenza, Measles, Coronavirus); parasites (e.g., Trypanosome, *Plasmodium, Leishmania*); fungi (e.g., *Aspergillus, Candida, Coccidioides, Cryptococcus*); and the like. For example, the antigen may be from bacteria, particularly pathogenic bacteria, such as the causative agent of anthrax (*Bacillus anthracis*), plague (*Yersinia pestis*), tuberculosis (*Mycobacterium tuberculosis*), salmonellosis (*Salmonella enterica*), stomach cancer (*Helicobacter pylori*), sexually transmitted diseases (*Chlamydia trachomatis* or *Neisseria* gonorrhea), and the like. Other representative examples include antigens from certain viruses, such as influenza virus(es), Norwalk virus, smallpox virus, West Nile virus, SARS virus, MERS virus, respiratory syncytial virus, measles virus, and the like. Fungi of interest include, but are not limited to *Candida albicans* or *Aspergillus* spp., and parasites of interest include the causative agents of trypanosomiasis, leishmania, pneumonic plague, and lyme disease (*Borrelia burgdorferi*).

A pathologically aberrant cell to be used in a vaccine can be obtained from any source such as one or more individuals having a pathological condition or ex vivo or in vitro cultured cells obtained from one or more such individuals, including a specific individual to be treated with the resulting vaccine.

A vaccine formulation for use with an adjuvant containing cyclic di-nucleotide active agents may include, e.g., attenuated and inactivated viral and bacterial pathogens from infected patients or propagated cultures, purified macromolecules, polysaccharides, toxoids, recombinant antigens, organisms containing a foreign gene from a pathogen, synthetic peptides, polynucleic acids, antibodies and tumor cells.

Recombinant antigens may be obtained, for example, by isolating and cloning a gene encoding any immunogenic polypeptide, in, e.g., bacterial, yeast, insect, reptile or mammalian cells using recombinant methods well known in the art and described, for example in Sambrook et al., Molecular Cloning: A Laboratory Manual, Cold Spring Harbor Laboratory, New York (1992) and in Ansubel et al., Current Protocols in Molecular Biology, John Wiley and Sons, Baltimore, Md. (1998). A number of genes encoding surface antigens from viral, bacterial and protozoan pathogens have been successfully cloned, expressed and used as antigens for vaccine development. For example, the major surface antigen of hepatitis B virus, HbsAg, the b subunit of choleratoxin, the enterotoxin of *E. coli*, the circumsporozoite protein of the malaria parasite, and a glycoprotein membrane antigen from Epstein-Barr virus, as well as tumor cell antigens, have been expressed in various well known vector/host systems, purified and used in vaccines.

A vaccine formulation containing cyclic di-nucleotide or STING active agents may advantageously contain other vaccine adjuvants and carriers. These carriers and adjuvants include, but are not limited to, ion exchange resins, alumina, aluminum stearate, lecithin, serum proteins, such as human serum albumin, buffer substances such as phosphates, glycine, sorbic acid, potassium sorbate, partial glyceride mixtures of saturated vegetable fatty acids, phosphate buffered saline solution, water, emulsions (e.g. oil/water emulsion), salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances and polyethylene glycol.

Any convenient method for determining if a vaccine compound or formulation induces an innate, humoral, cell-mediated, or any combination of these types of immune response may be employed. For example, the ability of a vaccine compound or formulation to induce an innate immune response through STING can be determined using methods described herein as well as other methods. Such methods for detecting an innate immune response can be generally performed within hours of vaccine administration. The ability of a vaccine compound or formulation to induce a humoral response can be determined by measuring the titer of antigen-specific antibodies in an animal primed with the vaccine and boosted with the antigen, or determining the presence of antibodies cross-reactive with an antigen by ELISA, Western blotting or other well-known methods. Cellular immune responses can be determined, for example, by measuring cytotoxic T cell response to antigen using a variety of methods, such as, e.g., FACS sorting, and other methods well known in the art. Methods of detecting humoral and cellular immune responses can be generally performed days or weeks after vaccine administration.

Cyclic-Di-Nucleotides

In another aspect, provided herein are 2'-5' phosphodiester linkage containing cyclic-di-nucleotides. As used herein, "cyclic-di-nucleotide" refers to a compound containing two nucleosides (i.e., a first and second nucleoside), wherein the 2' or 3' carbon of each nucleoside is linked to the 5' carbon of the other nucleoside by a phosphodiester bond. Therefore, a 2'-5' phosphodiester linkage containing cyclic-di-nucleotide refers to a cyclic-di-nucleotide, wherein the 2' carbon of at least one of the nucleosides is linked to the 5' carbon of the other nucleoside. As discussed herein, 2'-5' phosphodiester linkage containing cyclic-di-nucleotides can be used in practicing the methods described herein for increasing production of a type I interferon in a cell or subject. As used herein a "cyclic-di-nucleotide" also includes all of the stereoisomeric forms of the cyclic-di-nucleotides described herein.

As used herein, a "nucleoside" refers to a composition containing a nitrogenous base covalently attached to a sugar (e.g., ribose or deoxyribose) or an analog thereof. Examples of nucleosides include, but are not limited to cytidine, uridine, adenosine, guanosine, thymidine and inosine. In some embodiments, the nucleoside contains a deoxyribose sugar. Analogs of nucleosides include, but are not limited to deoxyadenosine analogues (e.g., Didanosine and Vidarabine); deoxycytidine analogues (e.g., Cytarabine, Emtricitabine, Lamivudine, and Zalcitabine); deoxyguanosine analogues (Abacavir and Entecavir); (deoxy-) thymidine analogues (e.g., Stavudine, Telbivudine, and Zidovudine); and deoxyuridine analogues (e.g., Idoxuridine and Trifluridine).

While not being bound by any particular theory of operation, and as shown in the examples below, cyclic-di-nucleotides can increase type-I IFN production in a cell. In certain embodiments, cyclic-di-nucleotides increase type-I IFN production through a mechanism that involves stimulator of interferon genes (STING).

Cyclic-di-nucleotides include those specifically described herein as well as isoforms (e.g., tautomers) of those specifically described herein that can be used in practicing the subject methods. Cyclic-di-nucleotides can be obtained using any suitable method. For example, cyclic-di-nucleotides may be made by chemical synthesis using nucleoside derivatives as starting material. Cyclic-di-nucleotides can also be produced by in vitro synthesis, using recombinant purified cGAMP synthase (cGAS), as described in the Experimental Section below. Moreover, the structures of such cyclic-di-nucleotides can be confirmed using NMR analysis.

Cyclic-di-nucleotides provided herein can be described by the following nomenclature: cyclic[$X_1$(A-5')p$X_2$(B-5')p], wherein $X_1$ and $X_2$ are the first and second nucleoside, A is the carbon of the first nucleoside (e.g., 2' or 3' position) that is linked to the 5' carbon of the second nucleoside via a phosphodiester bond and B is the carbon of the second nucleoside (e.g., 2' or 3' position) that is linked to the 5' carbon of the first nucleoside by a phosphodiester bond. For instance, based on this nomenclature, cyclic[G(2'-5')pA(3'-5')p] has the following formula:

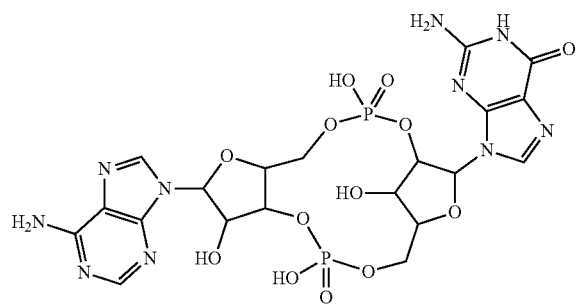 [SMILES: Nc1nc2c(ncn2C2OC3COP(=O)(O)OC4C(COP(=O)(O)OC2C3O)OC(n2cnc3c(N)ncnc32)C4O)c(=O)[nH]1]

In certain embodiments, the cyclic-di-nucleotide contains a 2'-5' phosphodiester bond. In particular embodiments, the cyclic-di-nucleotide further contains a 3'-5' phosphodiester bond (e.g., cyclic[$X_1$(2'-5')p$X_2$(3'-5')p] or cyclic[$X_1$(3'-5')p$X_2$(2'-5')p]). In other embodiments, the cyclic-di-nucleotide contains two 2'-5' phosphodiester bonds (cyclic[$X_1$(2'-5')p$X_2$(2'-5')p]).

In certain embodiments, the cyclic-di-nucleotide is:
cyclic[A(2'-5')pA2'-5')p];
cyclic[T(2'-5')pT(2'-5')p];
cyclic[G(2'-5')pG(2'-5')p];
cyclic[C(2'-5')pC(2'-5')p]; or
cyclic[U(2'-5')pU(2'-5')p].

In certain embodiments, the cyclic-di-nucleotide is:
cyclic[A(2'-5')pA(3'-5')p];
cyclic[T(2'-5')pT(3'-5')p];
cyclic[G(2'-5')pG(3'-5')p];
cyclic[C(2'-5')pC(3'-5')p];
cyclic[U(2'-5')pU(3'-5')p];
cyclic[A(2'-5')pT(3'-5')p];
cyclic[T(2'-5')pA(3'-5')p];
cyclic[A(2'-5')pG(3'-5')p];
cyclic[G(2'-5')pA(3'-5')p];
cyclic[A(2'-5')pC (3'-5')p];
cyclic[C(2'-5')pA(3'-5')p];
cyclic[A(2'-5')pU(3'-5')p];
cyclic[U(2'-5')pA(3'-5')p];
cyclic[T(2'-5')pG(3'-5')p];
cyclic[G(2'-5')pT(3'-5')p];
cyclic[T2'-5')pC(3'-5')p];
cyclic[C(2'-5')pT(3'-5')p];
cyclic[T(2'-5')pU(3'-5')p];
cyclic[U(2'-5')pT(3'-5')p];
cyclic[G(2'-5')pC(3'-5')p];
cyclic[C(2'-5')pG(3'-5')p];
cyclic[G(2'-5')pU(3'-5')p];
cyclic[U(2'-5')pG(3'-5')p];
cyclic[C(2'-5')pU(3'-5')p]; or
cyclic[U(2'-5')pC(3'-5')p].

In certain embodiments, the cyclic-di-nucleotide has the following formula:

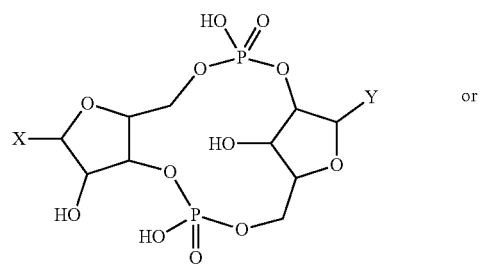

or

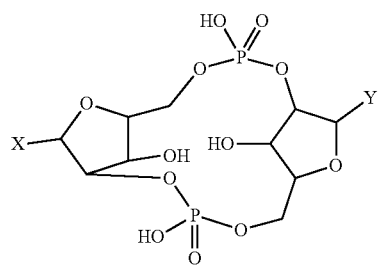

wherein X and Y can be any organic molecule including a nitrogenous base. As used herein a "nitrogenous base" refers to nitrogen-containing molecules having the chemical properties of a base including, but not limited to, pyrimidine derivatives (e.g., cytosine, thymine, and uracil) and purine derivatives (e.g., adenine and guanine), as well as substituted pyrimidine and purine derivatives, pyrimidine and purine analogs, and their tautomers. In certain embodiments, X and Y are each one of the following:

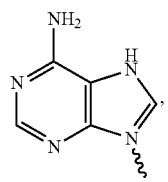 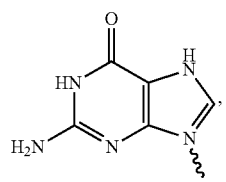

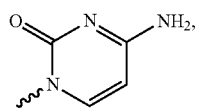, 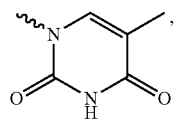, or

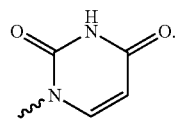.

In certain embodiments, the cyclic-di-nucleotide has the following formula (cyclic[G(2'5')pA(3'5')p]):

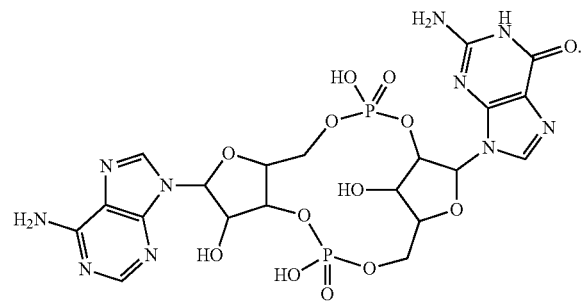 [SMILES: Nc1nc2c(ncn2C2OC3COP(=O)(O)OC4C(COP(=O)(O)OC2C3O)OC(n2cnc3c(N)ncnc32)C4O)c(=O)[nH]1]

In certain embodiments, the cyclic-di-nucleotide has the following formula (cyclic[G(3'5')pA(2'5')p]):

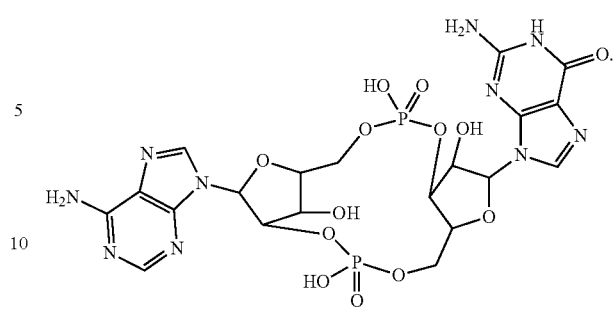

In other embodiments, the cyclic-di-nucleotide has the following formula cyclic[G(2'5')pA(2'5')p]:

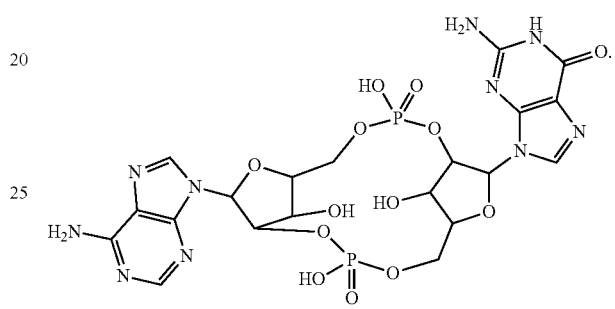

In other embodiments, the cyclic-di-nucleotide has the following formula cyclic[A(2'5')pA(3'5')p]:

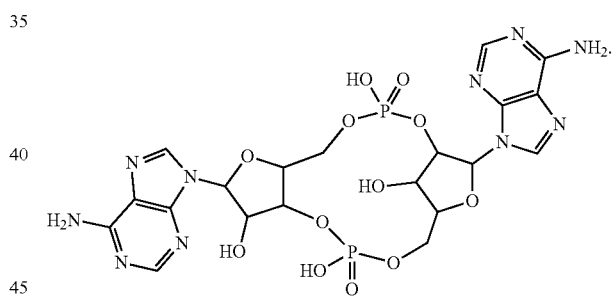

In yet other embodiments, the cyclic-di-nucleotide has the following formula cyclic[G(2'5')pG(3'5')p]:

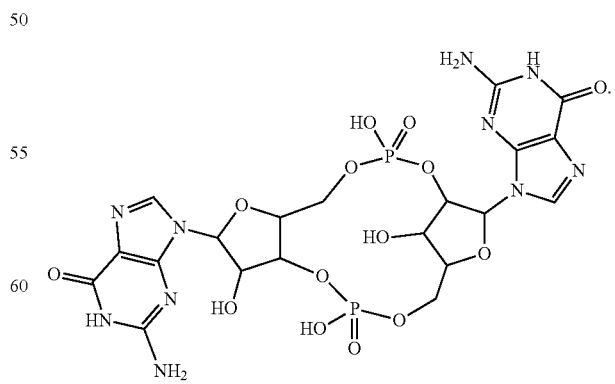

In certain embodiments, the cyclic-di-nucleotide has the following formula cyclic[A(2'5')pA(2'5')p]:

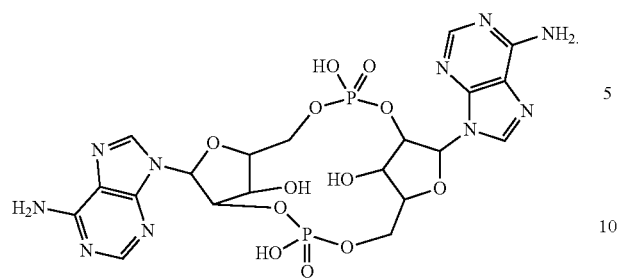
In certain embodiments, the cyclic-di-nucleotide has the following formula cyclic[G(2'5')pG(2'5')p]:
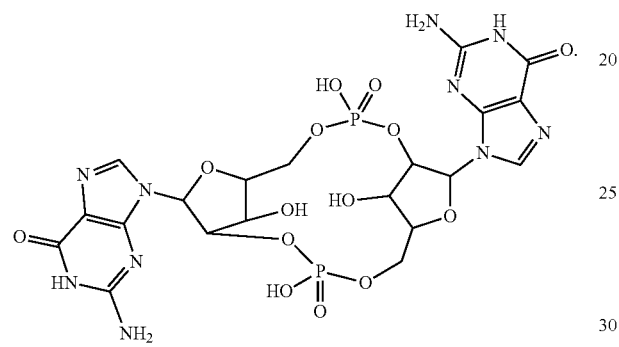
In certain embodiments, the cyclic-di-nucleotide has one of the following formulas:
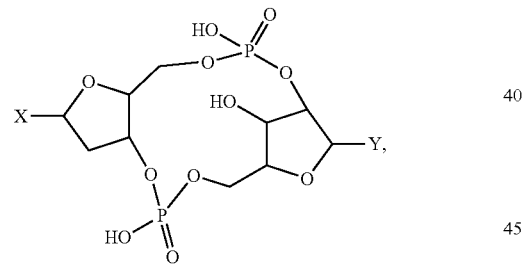
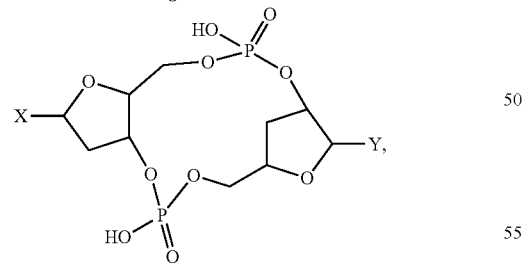
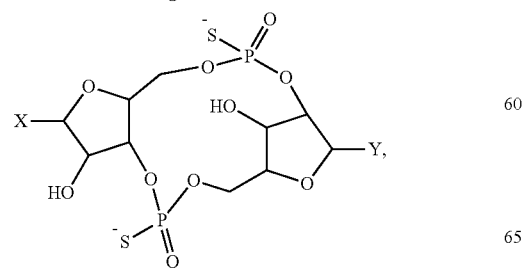
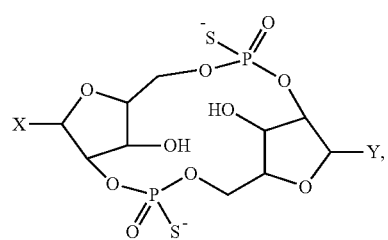
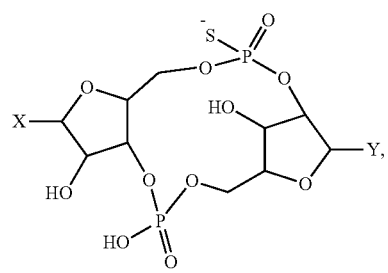
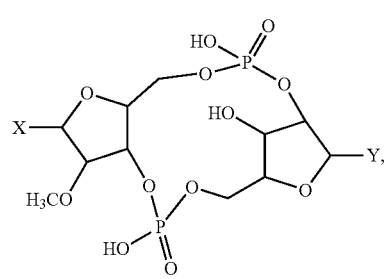
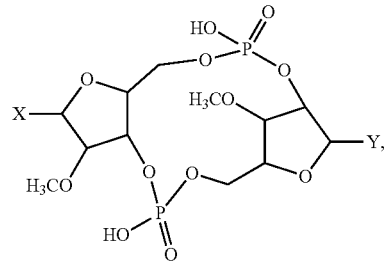
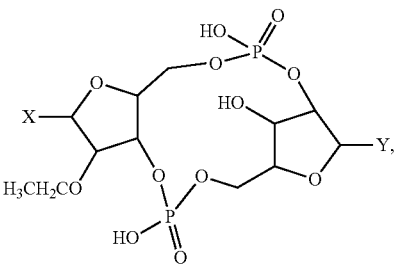
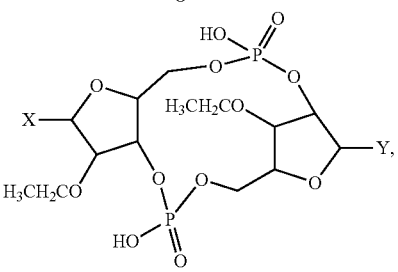

37
-continued
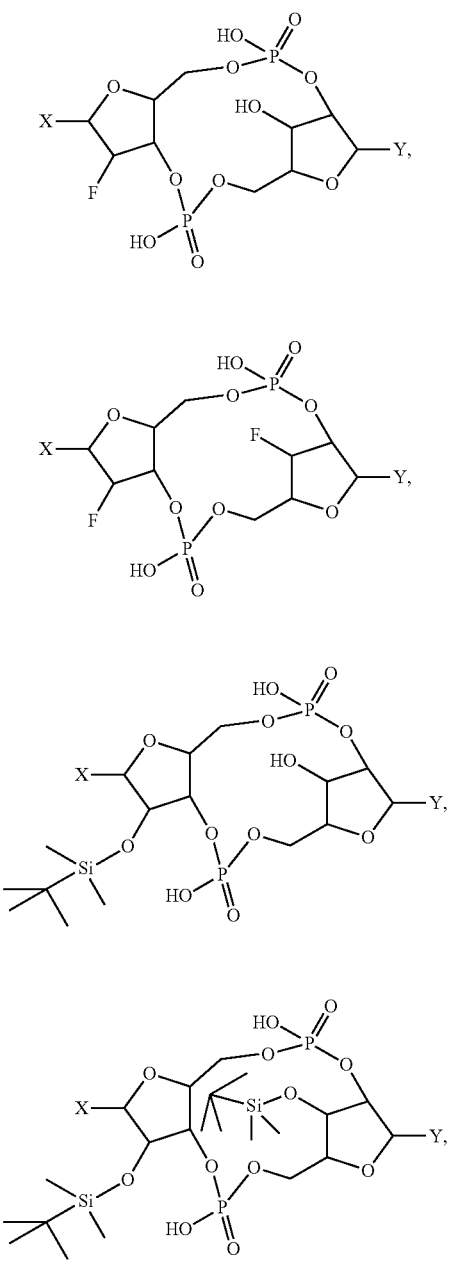
38
-continued
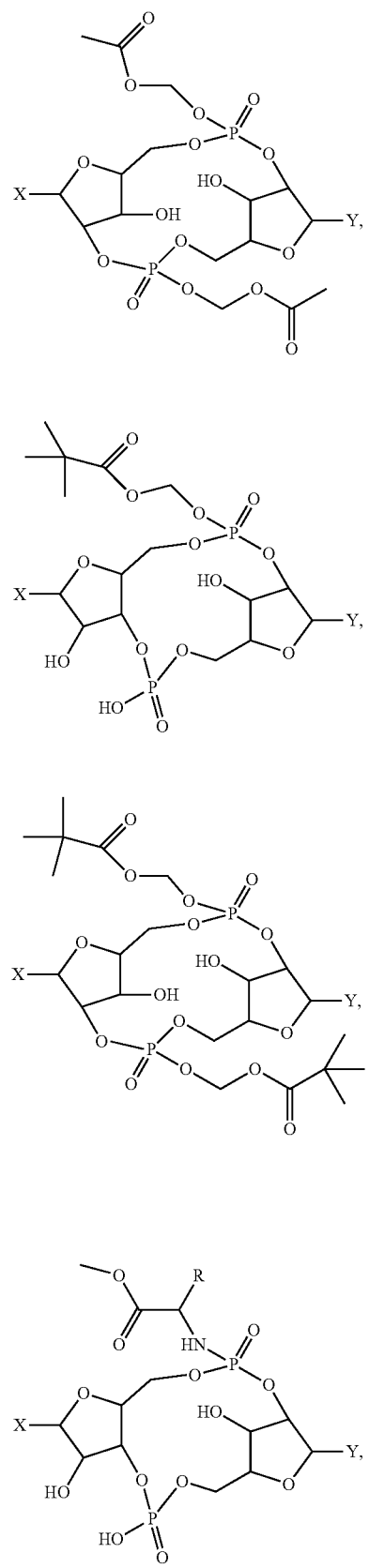

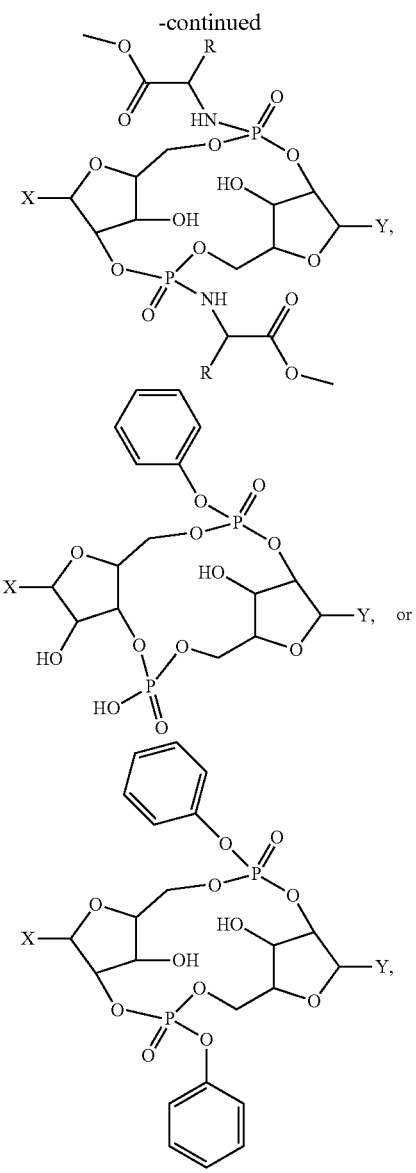

wherein R is any amino acid side chain.

Pharmaceutical Compositions

In another aspect, provided herein is a pharmaceutical composition that contains any of the cyclic-di-nucleotide active agents provided herein and a pharmaceutically acceptable carrier. In certain embodiments of the pharmaceutical composition, the cyclic-di-nucleotide active agent is one or more cyclic-di-nucleotides.

The term "pharmaceutically acceptable" means approved by a regulatory agency of the Federal or a state government or listed in the U.S. Pharmacopeia or other generally recognized foreign pharmacopeia for use in animals, and more particularly in humans. The term "carrier" refers to a diluent, adjuvant, excipient, or vehicle with which the mitochondrial transport protein inhibitor is administered. Such pharmaceutical carriers can be, for example, sterile liquids, such as saline solutions in water and oils, including those of petroleum, animal, vegetable or synthetic origin, such as peanut oil, soybean oil, mineral oil, sesame oil and the like. A saline solution is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. The inhibitors can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc. Examples of suitable pharmaceutical carriers are described in "Remington's Pharmaceutical Sciences" by E. W. Martin, hereby incorporated by reference herein in its entirety. Such compositions will contain a therapeutically effective amount of the mitochondrial transport protein (e.g., a Miro protein, a TRAK protein, or Khc) inhibitor, preferably in purified form, together with a suitable amount of carrier so as to provide the form for proper administration to the patient. The formulation should suit the mode of administration.

The pharmaceutical composition can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249: 1527-1533 (1990).

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use may be sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

The pharmaceutical composition can be formulated for intravenous, oral, via implant, transmucosal, transdermal, intramuscular, intrathecal, or subcutaneous administration.

In some embodiments, the pharmaceutical composition is formulated for intravenous administration. In other embodiments, the pharmaceutical composition is formulated for subcutaneous administration. The following delivery systems, which employ a number of routinely used pharmaceutical carriers, are only representative of the many embodiments envisioned for administering the instant compositions.

Injectable drug delivery systems include solutions, suspensions, gels, microspheres and polymeric injectables, and can comprise excipients such as solubility-altering agents (e.g., ethanol, propylene glycol and sucrose) and polymers (e.g., polycaprolactones and PLGAs). Implantable systems include rods and discs, and can contain excipients such as PLGA and polycaprolactone. Osteopontin or nucleic acids of the invention can also be administered attached to particles using a gene gun.

Oral delivery systems include tablets and capsules. These can contain excipients such as binders (e.g., hydroxypropylmethylcellulose, polyvinyl pyrolidone, other cellulosic materials and starch), diluents (e.g., lactose and other sugars, starch, dicalcium phosphate and cellulosic materials), disintegrating agents (e.g., starch polymers and cellulosic materials) and lubricating agents (e.g., stearates and talc).

Transmucosal delivery systems include patches, tablets, suppositories, pessaries, gels and creams, and can contain excipients such as solubilizers and enhancers (e.g., propylene glycol, bile salts and amino acids), and other vehicles (e.g., polyethylene glycol, fatty acid esters and derivatives, and hydrophilic polymers such as hydroxypropylmethylcellulose and hyaluronic acid).

Dermal delivery systems include, for example, aqueous and nonaqueous gels, creams, multiple emulsions, microemulsions, liposomes, ointments, aqueous and nonaqueous solutions, lotions, aerosols, hydrocarbon bases and powders, and can contain excipients such as solubilizers, permeation enhancers (e.g., fatty acids, fatty acid esters, fatty alcohols and amino acids), and hydrophilic polymers (e.g., polycarbophil and polyvinylpyrolidone). In one embodiment, the pharmaceutically acceptable carrier is a liposome or a transdermal enhancer.

In certain embodiments, the pharmaceutical composition containing the cyclic-di-nucleotide active agent is formulated to cross the blood brain barrier (BBB). One strategy for drug delivery through the blood brain barrier (BBB) entails disruption of the BBB, either by osmotic means such as mannitol or leukotrienes, or biochemically by the use of vasoactive substances such as bradykinin. A BBB disrupting agent can be co-administered with the therapeutic compositions when the compositions are administered by intravascular injection. Other strategies to go through the BBB may entail the use of endogenous transport systems, including caveoil-1 mediated transcytosis, carrier-mediated transporters such as glucose and amino acid carriers, receptor-mediated transcytosis for insulin or transferrin, and active efflux transporters such as p-glycoprotein. Active transport moieties may also be conjugated to the therapeutic compounds for use in the invention to facilitate transport across the endothelial wall of the blood vessel. Alternatively, drug delivery of the ND pharmaceutical composition behind the BBB may be by local delivery, for example by intrathecal delivery, e.g., through an Ommaya reservoir (see, e.g., U.S. Pat. Nos. 5,222,982 and 5,385,582, incorporated herein by reference); by bolus injection, e.g., by a syringe, e.g., intravitreally or intracranially; by continuous infusion, e.g., by cannulation, e.g., with convection (see, e.g., US Application No. 20070254842, incorporated here by reference); or by implanting a device upon which the inhibitor pharmaceutical composition has been reversibly affixed (see e.g., US Application Nos. 20080081064 and 20090196903, incorporated herein by reference).

In certain embodiments, the pharmaceutical composition containing the cyclic-di-nucleotide or STING active agents is formulated in a delivery vehicle, e.g., to enhance cytosolic transport. Any convenient protocol may be employed to facilitate delivery of the cyclic-di-nucleotide active agent across the plasma membrane of a cell and into the cytosol. In certain embodiments, the cyclic-di-nucleotide or STING active agents and an antigen effective for use in a vaccine may be formulated together to be delivered by the same delivery vehicle in the pharmaceutical composition.

In some instances, the cyclic-di-nucleotide or STING active agents may be encapsulated in a delivery vehicle comprising liposomes in the pharmaceutical composition. Methods of using liposomes for drug delivery and other therapeutic uses are known in the art. See, e.g., U.S. Pat. Nos. 8,329,213, 6,465,008, 5,013,556, US Application No. 20070110798, and Andrews et al., Mol Pharm 2012 9:1118, which are incorporated herein by reference. Liposomes may be modified to render their surface more hydrophilic by adding polyethylene glycol ("pegylated") to the bilayer, which increases their circulation time in the bloodstream. These are known as "stealth" liposomes and are especially useful as carriers for hydrophilic (water soluble) molecules, such as the cyclic-di-nucleotide active agents.

In certain embodiments, nano- or microparticles made from biodegradable materials such as poly(lactic acid), poly(γ-glutamic acid), poly(glycolic acid), polylactic-co-glycolic acid. Polyethylenimine, or alginate microparticles, and cationic microparticles, including dendrimers, such as cyclodextrins, may be employed as delivery vehicles for cyclic-di-nucleotide or STING active agents to promote cellular uptake. See, e.g., U.S. Pat. No. 8,187,571, Krishnamachari et al., Adv Drug Deliv Rev 2009 61:205, Garzon et al., 2005 Vaccine 23:1384, incorporated herein by reference.

In another embodiment, photochemical internalization may be employed to enhance cytosolic uptake of cyclic-di-nucleotide or STING active agents. See, e.g., US Application No. 20120226217, incorporated herein by reference. In such embodiments, the cyclic-di-nucleotide or STING active agents may be co-adminstered with a photosensitizing agent. Then, exposure of the target cells to light of a specific wavelength triggers internalization of the cyclic-di-nucleotide or STING active agents.

In certain embodiments, the delivery vehicle for delivering the cyclic-di-nucleotide or STING active agents can also be targeting delivery vehicles, e.g., a liposome containing one or more targeting moieties or biodistribution modifiers on the surface of the liposome. A targeting moiety can be any agent that is capable of specifically binding or interacting with a desired target.

The specific binding agent can be any molecule that specifically binds to a protein, peptide, biomacromolecule, cell, tissue, etc. that is being targeted (e.g., a protein peptide, biomacromolecule, cell, tissue, etc. wherein the cyclic-di-nucleotide or STING active agent exerts its desired effect). Depending on the nature of the target site, the specific binding agent can be, but is not limited to, an antibody against an epitope of a peptidic analyte, or any recognition molecule, such as a member of a specific binding pair. For example, suitable specific binding pairs include, but are not limited to: a member of a receptor/ligand pair; a ligand-binding portion of a receptor; a member of an antibody/ antigen pair; an antigen-binding fragment of an antibody; a hapten; a member of a lectin/carbohydrate pair; a member of an enzyme/substrate pair; biotin/avidin; biotin/streptavidin; digoxin/antidigoxin; a member of a peptide aptamer binding pair; and the like.

In certain embodiments, the specific binding moiety includes an antibody. An antibody as defined here may include fragments of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein. The antibodies may also include Fab', Fv, F(ab')$_2$, and or other antibody fragments that retain specific binding to antigen.

In certain embodiments, the targeting moiety is a binding agent that specifically interacts with a molecule expressed on a tumor cell or an immune cell (e.g., CD4, CD8, CD69, CD62L, and the like), such that the targeting delivery vehicle containing the cyclic-di-nucleotide or STING active agents is delivered to the site of a tumor or to specific immune cells.

Where desired, any combinations of the above listed delivery vehicles may be used advantageously to enhance delivery of the cyclic-di-nucleotide or STING active agents to the target cells.

Components of the pharmaceutical composition can be supplied either separately or mixed together in unit dosage form, for example, as a dry lyophilized powder or water free concentrate. Where the composition is to be administered by infusion, it can be dispensed with an infusion bottle containing sterile pharmaceutical grade water or saline. Where the composition is administered by injection, an ample of sterile water for injection or saline can be provided so that the ingredients may be mixed prior to administration.

In some embodiments, the pharmaceutical composition is supplied as a dry sterilized lyophilized powder that is capable of being reconstituted to the appropriate concentration for administration to a subject. In some embodiments, the pharmaceutical composition is supplied as a water free concentrate. In some embodiments, the pharmaceutical composition is supplied as a dry sterile lyophilized powder at a unit dosage of at least 0.5 mg, at least 1 mg, at least 2 mg, at least 3 mg, at least 5 mg, at least 10 mg, at least 15 mg, at least 25 mg, at least 30 mg, at least 35 mg, at least 45 mg, at least 50 mg, at least 60 mg, or at least 75 mg.

Solutions, suspensions and powders for reconstitutable delivery systems include vehicles such as suspending agents (e.g., gums, xanthans, cellulosics and sugars), humectants (e.g., sorbitol), solubilizers (e.g., ethanol, water, PEG and propylene glycol), surfactants (e.g., sodium lauryl sulfate, Spans, Tweens, and cetyl pyridine), preservatives and antioxidants (e.g., parabens, vitamins E and C, and ascorbic acid), anti-caking agents, coating agents, and chelating agents (e.g., EDTA).

In some embodiments, the pharmaceutical composition is formulated as a salt form. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

In certain embodiments, the pharmaceutical composition contains a prodrug derivative of any of the cyclic-di-nucleotide or STING active agents provided herein. Such prodrugs can be subsequently converted to an active form of the cyclic-di-nucleotide or STING active agent in the body of the subject administered the pharmaceutical composition.

Kits

Kits with unit doses of the subject cyclic-di-nucleotide active agents, e.g., one or more cyclic-di-nucleotides, e.g., in oral or injectable doses, are provided. In the subject kits, the one or more components are present in the same or different containers, as may be convenient or desirable.

In addition to the containers containing the unit doses will be instructions describing the use and attendant benefits of the cyclic-di-nucleotide in treating a pathological condition of interest. Instructions may be provided in a variety of different formats. In certain embodiments, the instructions may include complete protocols for practicing the subject methods or means for obtaining the same (e.g., a website URL directing the user to a webpage which provides the instructions), where these instructions may be printed on a substrate, where substrate may be one or more of: a package insert, the packaging, reagent containers and the like.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXPERIMENTAL

I. Results and Discussion

Recognition of pathogen-derived nucleic acid is a major mechanism by which innate immune responses are initiated in mammals (Barbalat et al., Annu Rev Immunol (2011) 29: 185). Several families of germ-line encoded nucleic acid sensors have been described, including the Toll-like receptors (TLRs) and RIG-I-like receptors (RLRs)(Palm et al., Immunol Rev (2009) 227: 221; Takeuchi et al., Cell (2010) 140: 805). Upon binding nucleic acids, these sensors initiate signaling cascades that lead to the production of cytokines and other immune effector proteins that provide host defense.

The cytosolic presence of foreign double-stranded (ds) DNA triggers a potent antiviral response dominated by the production of type I interferons (IFNs) (Ishii et al., Nat. Immunol. (2006) 7: 40; Stetson et al., Immunity (2006) 24: 93). However, the molecular mechanism linking dsDNA to interferon production has not been well characterized (Burdette & Vance, Nat. Immunol. (2013) 14: 19). A host protein, STING, was identified and shown to be required for the IFN response to cytosolic dsDNA (Ishikawa & Barber, Nature (2008) 455: 674; Ishikawa et al., Nature (2009) 461: 788; Sun et al., Proc Natl Acad Sci USA (2009) 106: 8653; and Zhong et al., Immunity (2008) 29: 538). STING was also shown to be required for the interferon response to bacterially-derived second messengers called cyclic-di-nucleotides (CDNs)(Jin et al., J Immunol (2011) 187: 2595; and Sauer et al., Infect Immun (2011) 79: 688). CDNs are secreted or released into the cytosol by certain bacterial pathogens (Woodward et al., Science (2010) 328: 1703) and bind directly to STING (Burdette et al., Nature (2011) 478: 515). Interestingly, however, a mutant (R231A) allele of mouse STING was identified that abolished responsiveness to CDNs but did not appreciably affect the interferon response to cytosolic DNA (Id). In contrast, 293T cells expressing wild-type mouse STING are responsive to CDNs but not to dsDNA. Thus, although the IFN responses to cytosolic CDNs and dsDNA both require STING, the responses to these chemically distinct ligands can be genetically uncoupled.

Based on two studies (Sun, et al., Science (2013) 339: 786; and Wu et al., Science (2013) 339: 826), it was proposed that the cytosolic presence of dsDNA leads to the production of a CDN, cyclic-GMP-AMP (cGAMP), by a DNA-dependent sensor called cGAMP synthase (cGAS). cGAMP was shown to bind and activate STING. However, it remained unclear how the STING R231A mutant could still initiate responses to dsDNA despite lacking responsiveness to CDNs. Therefore, the mechanism by which cGAS activates STING was investigated.

Figure 2:
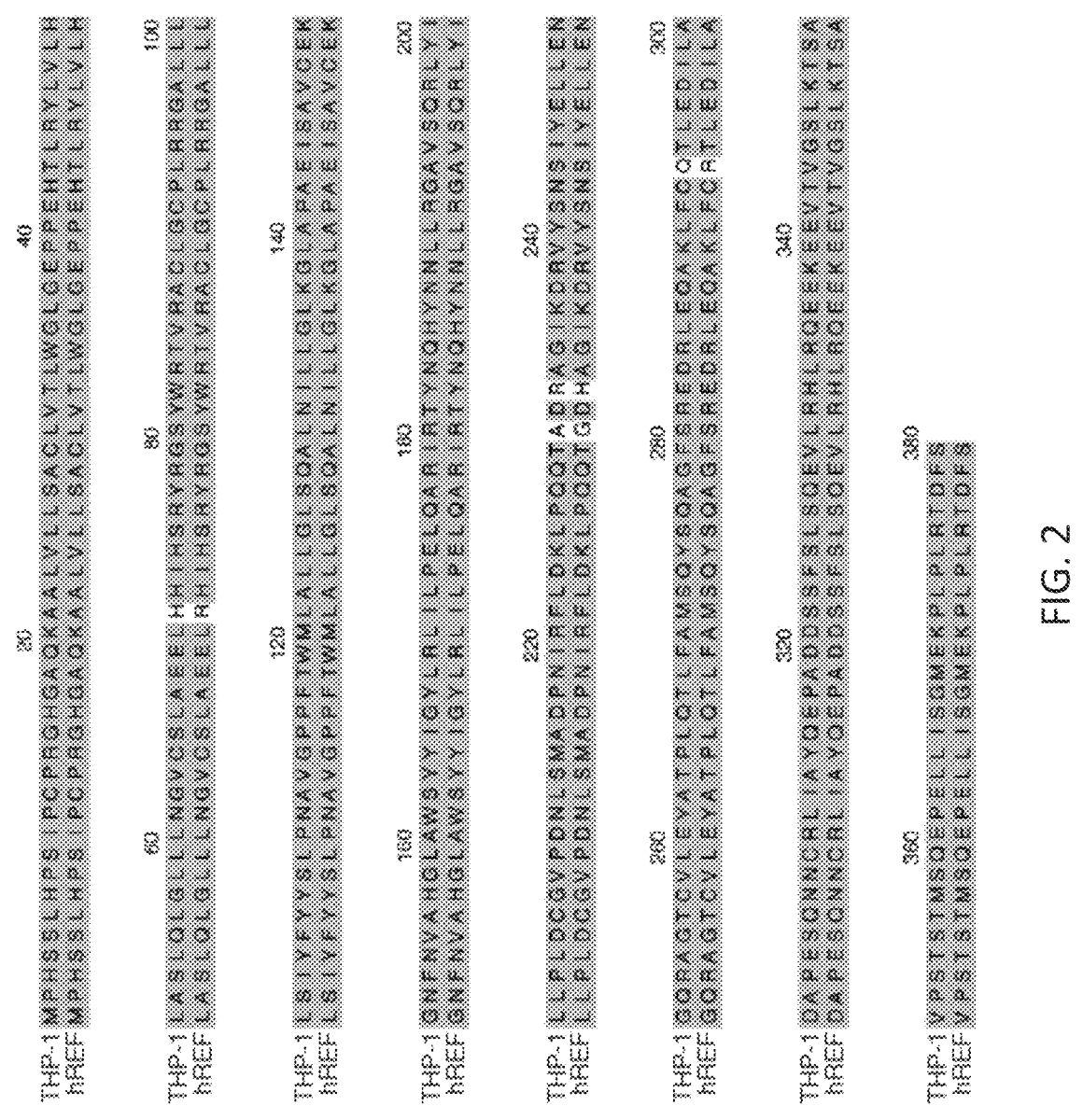

Previous studies (Sauer et al., Burdette et al.) focused primarily on mouse STING and it was not yet clear whether human STING could respond to CDNs (Conlon et al., J Immunol, (2013) 190: 5216). As previously reported (Sun et al., Wu et al.) it was found that the human THP-1 cell line responded robustly to CDNs in a manner dependent on STING (FIGS. 1A, B). hSTING was cloned from THP-1 cells and compared its amino acid sequence to the previously widely studied reference allele (NP_938023.1; denoted here as hSTING$^{REF}$) (7) (FIG. 2). It was found that hSTING$^{REF}$ and hSTING$^{THP-1}$ differ at four amino acid positions. Notably, hSTING$^{REF}$ encodes a histidine (H) at amino acid position 232, whereas hSTING$^{THP-1}$ encodes an arginine (R) at this position, which corresponds to R231 in mSTING that is critical for responsiveness to CDNs. Therefore, the functionality of individual hSTING alleles were tested by expressing these alleles in 293T cells that lack endogenous STING (Burdette et al.). As previously observed (Burdette et al.), overexpression of mSTING in 293T cells is sufficient to induce ligand-independent activation of an IFN-luciferase reporter construct; however, transfection of 293T cells with lower amounts of mSTING renders the cells responsive to CDNs. Likewise, 293T cells expressing hSTING$^{THP-1}$ were responsive to CDN stimulation. In contrast, cells expressing hSTING$^{REF}$ were poorly or non-responsive (FIG. 1C). Interestingly, it was observed that three recent crystal structures of STING bound to cyclic-di-GMP were of the poorly-responsive hSTING$^{REF}$ protein (Huang, et al., Nature Struct. & Mol. Biol. (2012) 19: 728; Ouyang et al., Immunity (2012) 36: 1073; Yin et al., Mol Cell (2012) 46: 735).

Figures 1D, 1E, 1F:
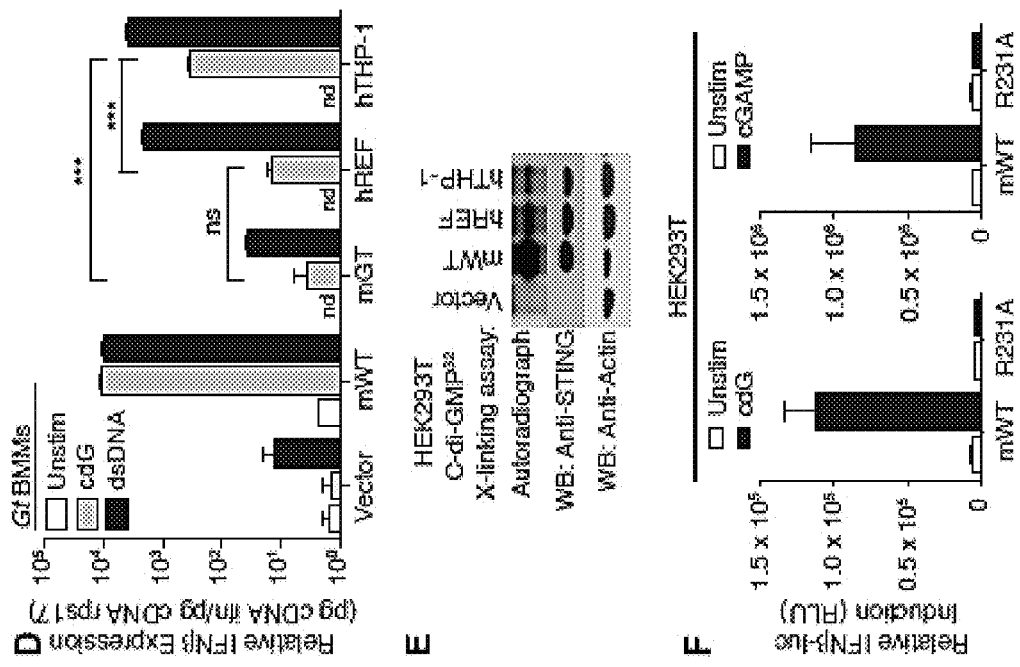

293T cells are not responsive to stimulation by dsDNA, presumably due to lack of expression of cGAS (Sun et al.) or perhaps other DNA sensors. Therefore, to test whether the hSTING variants could respond to DNA stimulation, STING-null ('goldenticket')(Sauer et al.), but (cGAS$^+$) macrophages were transduced with hSTING expression vectors. Interestingly, even the hSTING$^{REF}$ variant that is non-responsive to CDNs conferred responsiveness to dsDNA (FIG. 1D). hSTING$^{REF}$ therefore photocopies the R231A mutant of mouse STING, previously described that uncouples responsiveness to CDNs and dsDNA (Burdette et al.). Like the mSTING$^{R231A}$ variant, hSTING$^{REF}$ still bound to CDNs (FIG. 1E) (Huang et al., Ouyang et al., and Yin et al.), indicating that this allele is compromised at a step downstream of CDN binding.

Figure 3:
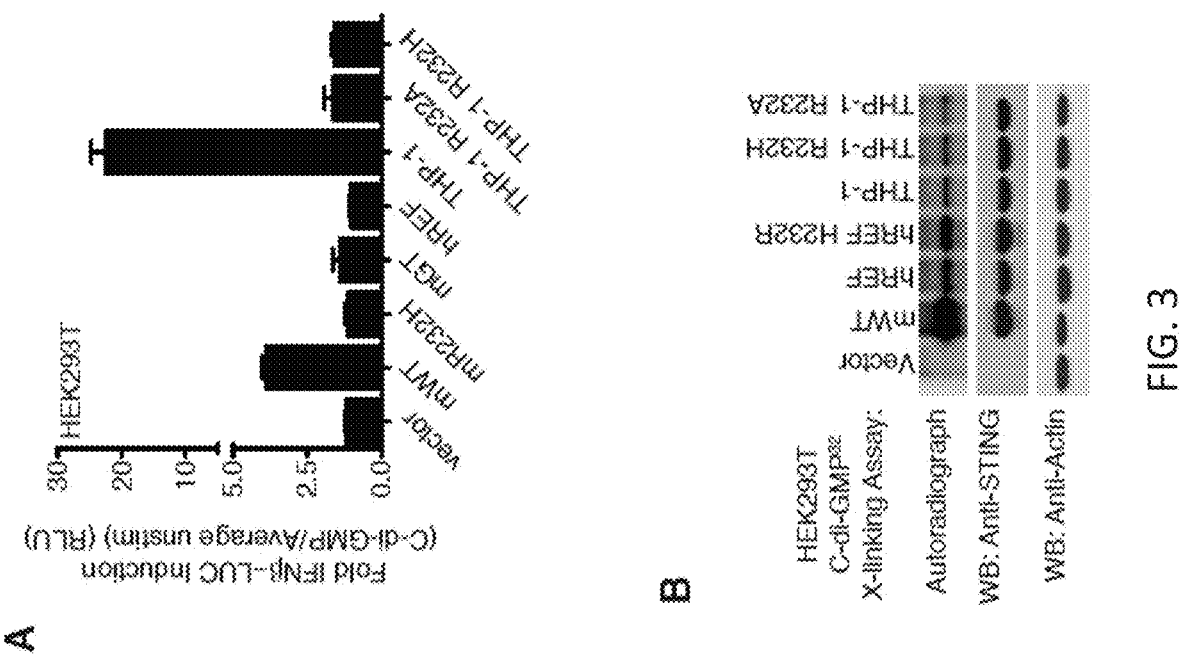
FIG. 3, panels A-B shows that R232 of human STING is required for responsiveness to c-di-GMP, but not for binding of c-di-GMP. (Panel A) 293T cells were transfected with the indicated alleles of mouse (m)STING or human (h)STING and were then stimulated with c-di-GMP (cdG). STING activity was detected by the induction of a co-transfected IFN-luciferase reporter construct and expressed as fold-induction over luciferase activity of unstimulated cells. (Panel B) Lysates of transfected 293T cells were UV cross-linked in the presence of α32P-c-di-GMP, resolved by SDS-PAGE, and then analyzed by autoradiography. Lysates were also western blotted for STING and ACTIN as expression controls in parallel.
Figure 4:
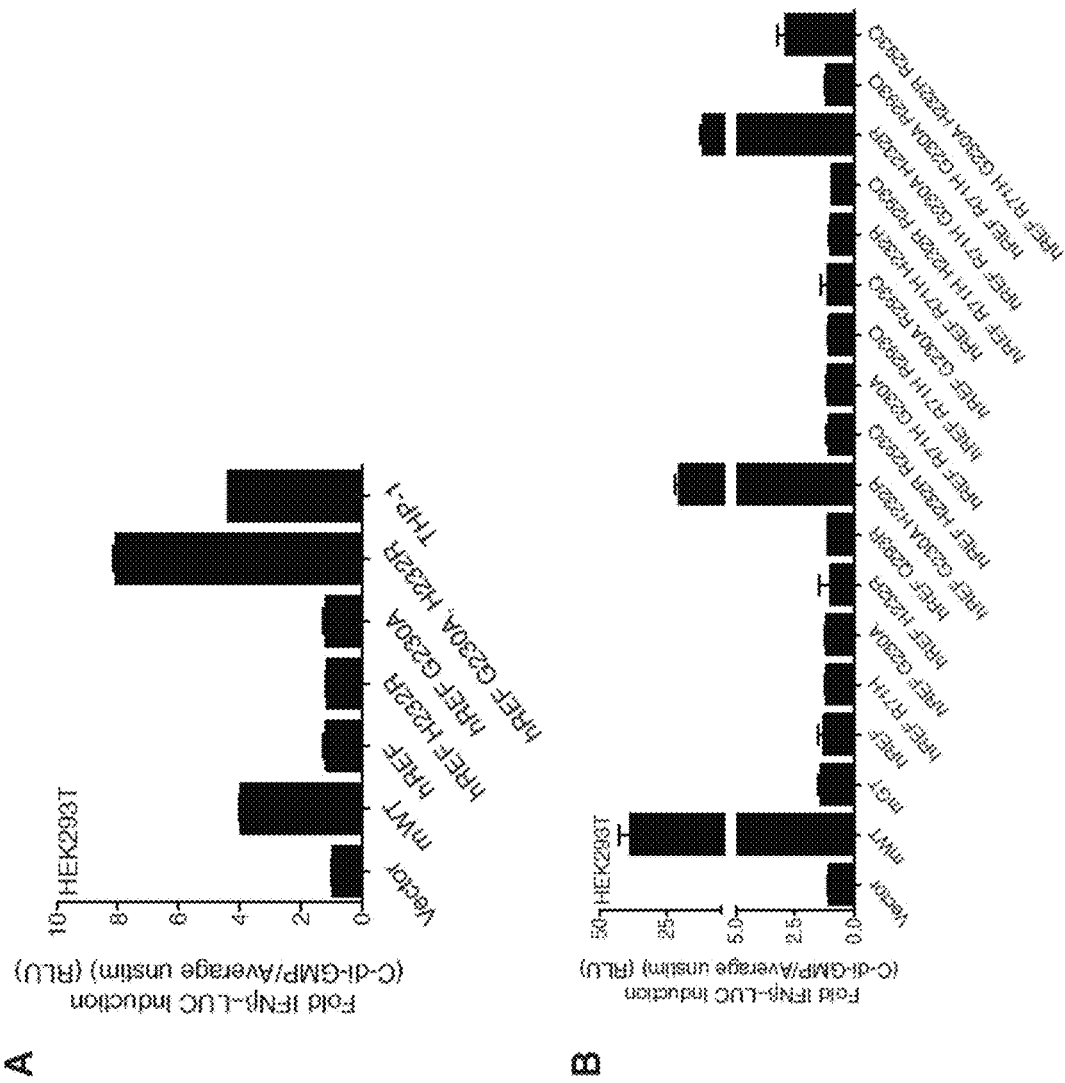
FIG. 4, panels A-B shows that G230A and H232R are both required for optimal responsiveness to c-di-nucleotides but are not required for binding to c-di-nucleotides. (Panels A, B) 293T cells were transfected with the indicated alleles of mouse (m)STING or human (h)STING and were then stimulated with c-di-GMP (cdG). STING activity was detected by the induction of a cotransfected IFN-luciferase reporter construct.

Consistent with the above results with hSTING alleles, an R231H mutant of mSTING was poorly responsive to CDNs, as were R232A or R232H variants of hSTING$^{THP}$ (FIG. 3A). It was therefore concluded that arginine 231/232 is critical for responsiveness to CDNs in mouse/human STING. Introduction of an H232R mutation in hSTING$^{REF}$, however was not sufficient to restore the responsiveness to CDNs; indeed, it was observed that a second substitution (G230A) was also required (FIG. 4). Again, all the variant STING alleles that were tested bound cyclic-di-GMP, consistent with the fact that residues 230 and 232 are located in loops that cover but do not form the CDN binding pocket (FIG. 3B) (Burdette & Vance).

Figure 5:
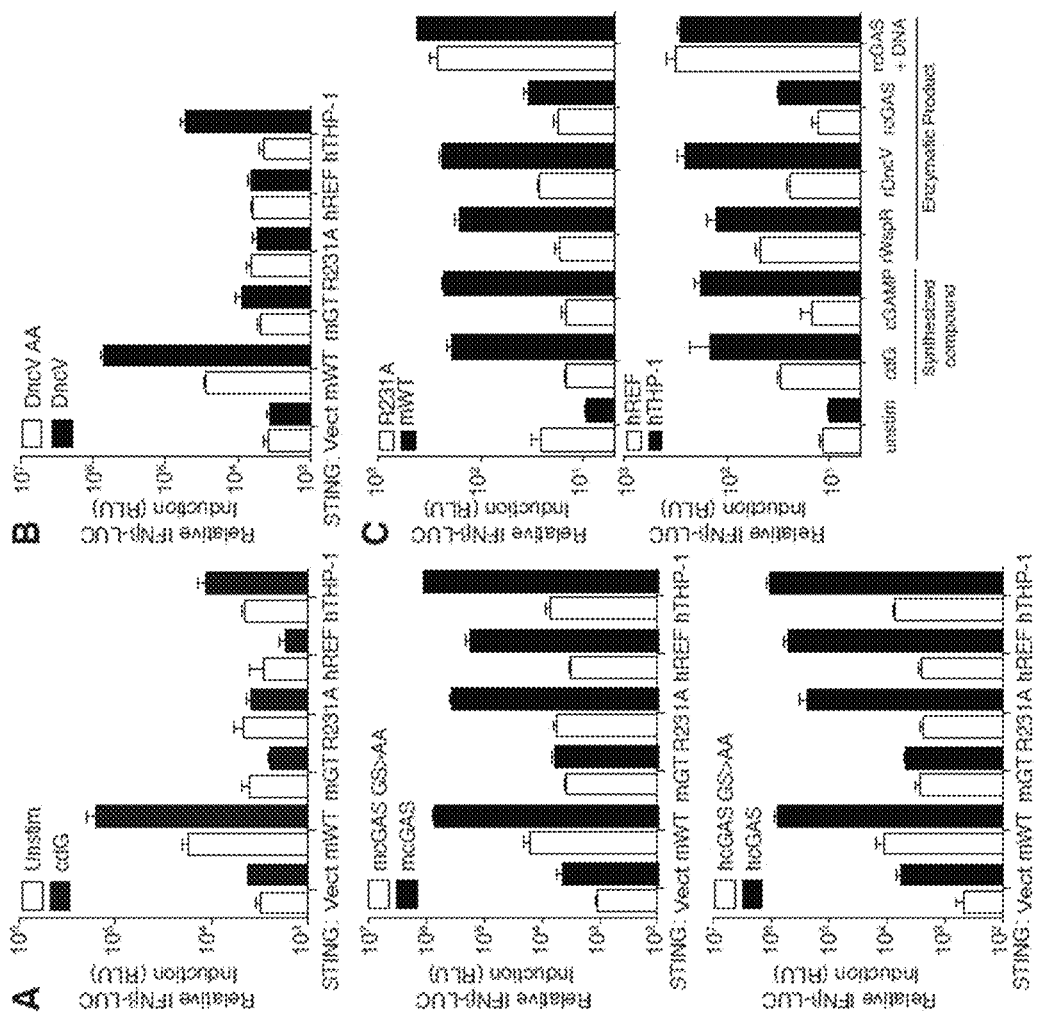
FIG. 5, panels A-C shows that STING variants are responsive to cGAS. (Panel A) HEK293T cells were transfected with the indicated STING alleles and with human and mouse cGAS (wt and GS>AA mutants) as indicated. STING activation was assessed by a co-transfected IFN-luciferase reporter construct. (Panel B) HEK293T cells were transfected with the indicated STING alleles and with a mammalian expression vector encoding a cGAMP synthase (DncV) from V. cholerae. STING activation was assessed as in A. (Panel C) In vitro enzymatically generated products of rWspR (cdG), rDncV and rcGAS (see FIG. 6, panel B) were transfected into digitonin permeabilized HEK293T cells expressing the indicated mouse (mSTING$^{R231A}$ or mSTING$^{WT}$) and human STING proteins (hSTING$^{REF}$ or hSTING$^{THP-1}$). As a negative control, dsDNA (required to stimulate cGAS activity) was omitted from a parallel cGAS reaction. Chemically synthesized canonical cyclic-di-GMP (cdG) and canonical cGAMP were included as controls. STING activation was assessed as in A and B. In contrast to synthetic canonical cGAMP, the dsDNA stimulated cGAS product was able to activate hSTING$^{REF}$ and mSTING$^{R231A}$.

Importantly, mSTING$^{R231A}$ was also non-responsive to chemically synthesized cGAMP (FIG. 1F) (Kellenberger, et al., J Am Chem Soc. (2013). 135:4906). This raised the question of whether R231A/R232H variants of STING would be responsive to the cGAS enzyme that is believed to activate STING via production of cGAMP. It was found that human or mouse cGAS expression was sufficient to robustly activate hSTING$^{REF}$ and mSTING$^{R231A}$ variants, even at very low levels of cGAS expression (FIG. 5A). Several explanations were considered for this result. One explanation is that the response is due simply to overexpression of the synthase in mammalian cells; however, overexpression of a bacterial enzyme that produces cGAMP (DncV from *V. cholerae*) (Davies, Cell (2012)149: 358) did not activate hSTING$^{REF}$ or mSTING$^{R231A}$ but did activate wild-type mSTING and hSTING$^{THP-1}$ (FIG. 5B). An alternative hypothesis is that cGAS might physically interact with STING and thereby activate STING in a manner independent of cGAMP production. However, this explanation also appears to be incorrect. As previously demonstrated (Sun et al.), overexpression of catalytically dead mutants of human or mouse cGAS failed to activate STING (GS>AA; FIG. 2A), arguing that cGAS signaling depends on the production of a second messenger rather than on a direct physical interaction with STING. To confirm this interpretation, the enzymatic product of cGAS was produced by providing ATP, GTP and dsDNA to purified recombinant cGAS in vitro. As a negative control, dsDNA (required to stimulate cGAS activity) was omitted from a parallel reaction. The resulting cGAS products were then purified and transfected into 293T cells expressing STING variants. In contrast to synthetic cGAMP, the cGAS product was able to activate hSTING$^{REF}$ and mSTING$^{R231A}$ (FIG. 5C). This experiment ruled out a model in which cGAS activates hSTING$^{REF}$ via a direct physical interaction.

Figure 6:
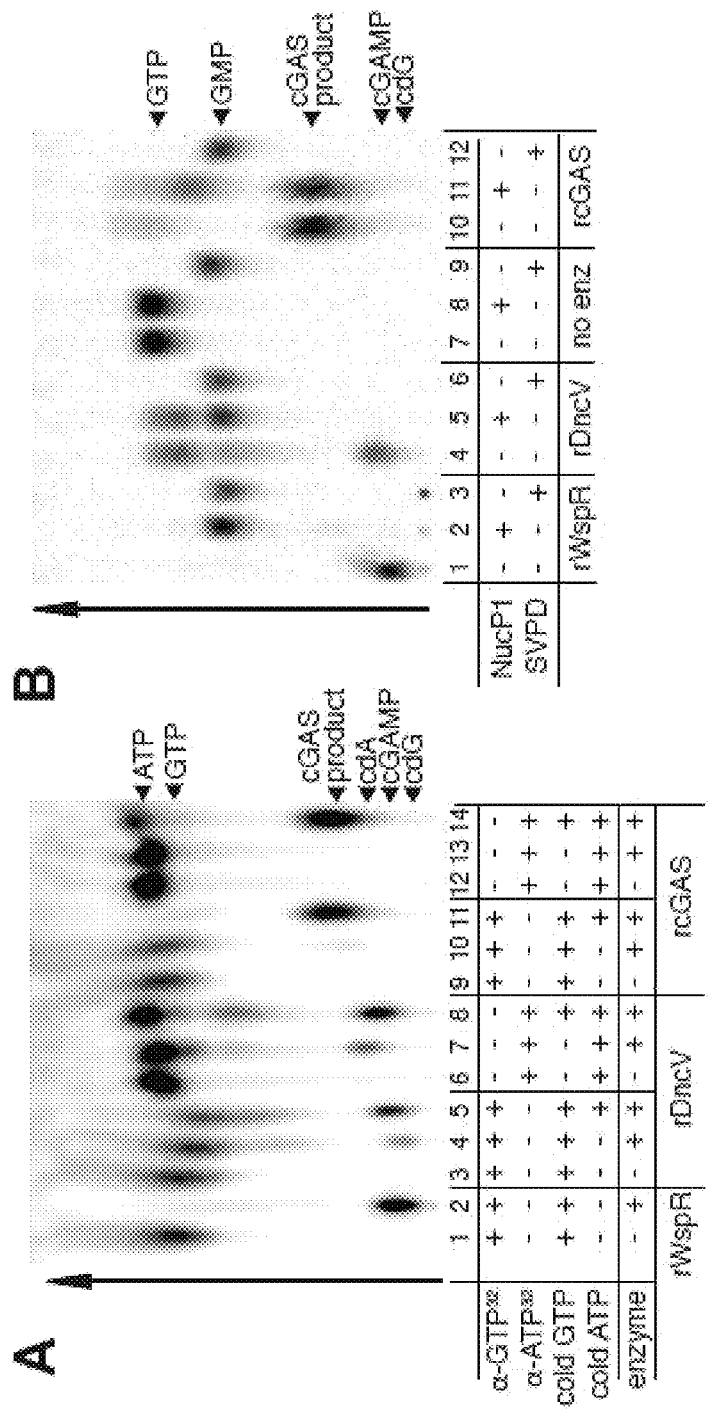
FIG. 6, panels A-C shows that cGAS produces a non-canonical cyclic dinucleotide containing a 2'-5' phosphodiester linkage. (Panel A) Purified recombinant WspR, DncV and cGAS were mixed with α$^{32}$P-GTP or α$^{32}$P-ATP and the indicated unlabeled nucleotides. Reactions were mixed with TLC running buffer and nucleic acid species were resolved on a PEI-Cellulose TLC plate. (Panel B) WspR, DncV and cGAS products labeled with α$^{32}$P-GTP were digested with nuclease P1 and Snake Venom Phosphodiesterase and nucleic acid species were resolved on a PEI-Cellulose TLC plate. (Panel C) $^1$H-$^{31}$P HMBC of HPLC-purified cGAS product acquired at 600 MHz and 50° C. Critical through-bond correlations for the phosphodiester bonds are indicated. NMR elucidated structure of cGAS product is also shown.

It was therefore hypothesized that the actual product of cGAS might not be a canonical CDN as previously proposed (Sun et al., Wu et al.). It was hypothesized that cGAS might produce a novel CDN containing 2'-5' phosphodiester bond(s) that would be able to stimulate variant STING alleles. Importantly, such a non-canonical CDN would be of an identical mass to the canonical 3'-5' phosphodiester-linked CDNs and the two products would not, therefore, have been easy to distinguish by previously published mass spectrometric analyses of the cGAS product (Sun et al., Wu et al.) To test this hypothesis radiolabelled α$^{32}$P-GTP or α$^{32}$P-ATP were provided to recombinant purified cGAS or *V. cholerae* DncV and the products were analyzed by thin-layer chromatography. As reported previously, DncV produced some c-di-AMP if provided only ATP, and some c-di-GMP if provided only GTP, but preferred to make cGAMP when provided both ATP and GTP (Davies, et al., Cell (2012)149: 358). (FIG. 6A). Interestingly, cGAS required both ATP and GTP substrates and the resulting product migrates significantly differently than any of the canonical CDNs produced by DncV, suggesting that cGAS produces a novel non-canonical CDN (FIG. 6A).

cGAS and DncV products were analyzed by specific nuclease digestion. The cGAS product was partially cleaved by nuclease P1, which selectively digests 3'-5' phosphodiester linkages, suggesting that the cGAS product contains at least one 3'-5' phosphodiester linkage (FIG. 6B). However, nuclease P1 digestion was incomplete as it did not lead to generation of GMP, in contrast to treatment of the cGAS product with snake venom phosphodiesterase, which cleaved both 2'-5' and 3'-5' phosphodiester linkages (FIG. 3B). This suggests that the cGAS product contains a 2'-5' phosphodiester linkage.

CDNs have been proposed to be useful as vaccine adjuvants or immunotherapeutics (Chen, et al., Vaccine (2010) 28:3080). A synthetic STING activator, DMXAA, has been tested in human clinical trials as a novel chemotherapeutic agent. Unfortunately, DMXAA was not found to be efficacious in humans, likely because it is unable to stimulate hSTING (Conlon et al.). In this context, our results are significant as they indicate that non-canonical 2'-5' linked CDNs function as potent pan-agonists of diverse STING variants, including those variants that are only poorly responsive to canonical CDNs or DMXAA.

II. Materials and Methods:

A. Mice and Cell Lines

THP-1 cells were grown in RPMI 1640 supplemented with 10% FBS, penicillin-streptomycin and L-glutamine. HEK293T cells were grown in DMEM supplemented with 10% FBS, penicillin-streptomycin and L-glutamine. Gp2 retroviral packaging cell lines were maintained in DMEM supplemented with 10% FBS, penicillin-streptomycin and L-glutamine. Animal protocols were approved by the University of California, Berkeley Animal Care and Use Committee.

B. STING Knockdown

Knockdown of human STING (clone ID NM_198282.1-901s1c1) was achieved using pLKO.1 (The RNAi Consortium). The sequence for knockdown of human STING is 5'-GCA GAG CTA TTT CCT TCC ACA (SEQ ID NO:07) which correspond to 5'-CCG GGC AGA GCT ATT TCC TTC CAC ACT CGA GTG TGG AAG GAA ATA GCT CTG CTT TTT G (SEQ ID NO:08) forward oligo and 5'-AAT TCA AAA AGC AGA GCT ATT TCC TTC CAC ACT CGA GTG TGG AAG GAA ATA GCT CTG C (SEQ ID NO:09) reverse oligo. Oligos were annealed and cloned into AgeI and EcoRI digested pLKO.1 (Addgene) and retrovirally transduced into THP-1 cells in parallel with scramble shRNA control constructs. Stable cell lines were selected with puromycin. THP-1 cells were differentiated with 1 µg/mL PMA for 24 hours. Cells were allowed to rest for 24 hours and then restimulated for 6 hours with the indicated ligands. IFN induction was measured by qRT-PCR as described below.

C. Cell Stimulation and Reagents

Bone marrow macrophages and HEK293T cells were stimulated using Lipofectamine 2000 (Invitrogen). Unless otherwise specified, cyclic-di-GMP, cyclic-di-AMP, polyI:C and Vaccinia Virus 70mer DNA was prepared as described previously (Burdette et al.) and used at similar concentrations. Sendai virus was purchased from Charles River Laboratories. cGAMP was synthesized as previously described (Kellenberger et al).

D. Cloning, Mutagenesis and Plasmids

The THP-1 STING allele was amplified from cDNA using 5' hSTING HindIII(5'-ATCGAA GCT TCC ACC ATG CCC CAC TCC AGC CTG) (SEQ ID NO:10) and 3' hSTING NotI (5'-ATC GGC GGC CGC TCA GGC ATA GTC AGG CAC GTC ATA AGG ATA AGA GAA ATC CGT GCG GAG AG) (SEQ ID NO:11). Resulting PCR product was cloned into pCDNA3 using HindIII/NotI digestion. THP-1 STING was amplified and cloned into MSCV2.2 using the 3' primer listed above and 5' hSTING XhoI (5'-ATC GCT CGA GCC ACC ATG CCC CAC TCC AGC CTG)(SEQ ID NO:12) and XhoI/NotI digestion. IFN-luciferase, TK-Renilla and mouse STING plasmids were used as previously described (Burdette et al.). Mutations in human STING were introduced using Quikchange Site Directed Mutagenesis Kit (Stratagene). cDNA clones corresponding to mouse and human cGAS (MGC Fully Sequenced Human MB21D1 cDNA, Accession: BC108714.1, Clone ID: 6015929; EST Fully Sequenced Mouse E330016A19Rik cDNA, Accession: BC145653.1, Clone ID: 40130956) were obtained from Open Biosystems and correspond to those described previously (Sun et al., Wu et al.). Mouse cGAS was amplified from cDNA clones with an N-terminal flag tag with forward oligo 5'-mcGAS-KpnI (5'-ATC GGG TAC CCC ACC ATG GAT TAC AAG GAT GAC GAT GAC AAG GAA GAT CCG CGT AGA AGG) (SEQ ID NO:13) and reverse oligo 3'-mcGAS-NotI (5'-ATC GGC GGC CGC TCA AAG CTT GTC AAA AAT TGG) (SEQ ID NO:14). Likewise, hcGAS was amplified with forward oligo 5'-hcGAS-flag-KpnI (5'-ATC GGG TAC CCC ACC ATG GAT TAC AAG GAT GAC GAT GAC AAG CAG CCT TGG CAC GGA AAG G) (SEQ ID NO:15) and reverse 3'-hcGAS-NotI (5'ATC GGC GGC CGC TCA AAA TTC ATC AAA AAC TGG AAA C)(SEQ ID NO:16). Both PCR products were cloned into pCDNA3 at KpnI and NotI restriction enzyme sites. DncV was amplified using DncV fwd BamHI (5'-GCA TGG ATC CGC CAC CAT GAC TTG GAA CTT TCA CCA G) (SEQ ID NO:17) and DncV rev NotI (5'-GCA TGC GGC CGC TCA GCC ACT TAC CAT TGT GCT GC)(SEQ ID NO:18) and cloned into pCDNA3 using BamHI and NotI. For cloning into MSCV2.2, DncV was amplified using DncV fwd XhoI (5'-GCA TCT CGA GCC ACC ATG ACT TGG AAC TTT CAC CAG) (SEQ ID NO:19) and DncV rev NotI. Resulting DNA was cloned into MSCV 2.2 digested with XhoI/NotI. Constructs for bacterial mcGAS overexpression were constructed as follows. N terminal His6-SUMO tag amplified by PCR using His6 SUMO Nco (5'-TAA TAA GGA GAT ATA CCA TGG GCA GCA GCC) (SEQ ID NO:20) and His6 SUMO Sal (5'-GAA TTC GTC GAC ACC AAT CTG TTC TCT GTG AGC)(SEQ ID NO:21) off of pCDF-Duet2 template (gift from M. Rape lab, UC-Berkeley) and cloned into pET28a using NcoI and SalI to make pET28a-H6SUMO. Full length mcGAS was PCR amplified from the mouse cDNA clone described above using mcGAS fwd Sal (5'-GAT GTC GAC ATG GAA GAT CCG CGT AGA AGG ACG)(SEQ ID NO:22) and mcGAS rev Xho (5'-ATC CTC GAG TCA AAG CTT GTC AAA AAT TGG AAA CC) (SEQ ID NO:23) and cloned into pET28a-H6SUMO using SalI and XhoI to make pET28a-H6SUMO-mcGAS that expresses full length mcGAS fused to an N-terminal His6 SUMO tag.

E. Protein Purifications

WspR construct (pQE-WspR*) was a generous gift from Steve Lory (Harvard). WspR purification and c-di-GMP synthesis reactions were carried out as previously described (Merighi, et al., Mol Microbiol (2007)65: 876). Overexpression strains and plasmids for DncV and mutant DncV were provided by J. Mekalanos. DncV protein was overexpressed and purified as previously described (Davies et al.). Briefly, DncV protein production was induced in mid-log phase for 3 h at 37° C. with 1 mM IPTG. Cells were lysed and DncV protein was purified under denaturing conditions. Cleared lysate was incubated with Ni-NTA and eluted in Urea Elution buffer (2M Urea, 10 mM Tris pH=8.0, 150 mM NaCl, 250 mM Imidazole). Eluted protein was dialyzed to 25 mM Tris-Cl, pH=7.5, 300 mM NaCl, 5 mM Mg(OAc)2, 10% glycerol, 2 mM DTT. H6SUMO-mcGAS was expressed in Rosetta(DE3) pLysS cells by overnight induction with 0.5 mM IPTG at 18° C. Cells were lysed into 50 mM Tris-Cl, pH=8, 300 mM NaCl, 20 mM Imidazole, 5 mM BME and 0.2 mM PMSF by French Press. Cleared lysate was incubated with Ni-NTA and bound protein was eluted with 20 mM Tris-Cl, pH=7.4, 150 mM NaCl, 300 mM Imidazole. Eluant was dialyzed to 20 mM Tris-Cl, pH=7.4, 150 mM NaCl, 5 mM β-mercaptoethanol with 10% glycerol. Protein was flash frozen and stored at −80° C.

F. cGAS Product Purification and Structural Characterization

The cGAS product was purified using reverse-phase HPLC on an Agilent 1260 Infinity HPLC equipped with an Agilent Polaris C18-A column (5 μm, 250 mm×10 mm, 180 Å). Purification conditions include a 100% to 0% gradient of solvent A over 20 min at 50° C. and a flow rate of 5 mL/min, where solvent A is 100 mM ammonium acetate in water and solvent B is acetonitrile. Purified elution fractions were evaporated multiple times in order to remove excess ammonia. Resonance assignments were made using COSY, $^1H$-$^{13}C$ HSQC, NOESY, $^1H$-$^{13}C$ HMBC, and 1H-$^{31}P$ HMBC. Characterization of cGAS product: $^1H$ NMR (900 MHz, D2O, 50° C., δ): 8.44 (1H, s), 8.42 (1H, s), 8.03 (1H, s), 6.31 (1H, s), 6.09 (1H, J=8 Hz, d), 5.75 (1H, m), 5.18 (1H, m), 4.93 (1H, s), 4.74, 4.62, 4.59 (1H, J=12 Hz, d), 4.55 (1H, s), 4.38 (1H, m), 4.33 (1H, J=12 Hz, d), 4.28 (1H, J=12 Hz, d); 31P {$^1H$ decoupled} NMR (600 MHz, D20, 50° C., δ): (all resonances are singlets) −0.96, −1.86; HRMS (m/z): [M-H]− monoisotopic mass calculated for $C_{20}H_{24}N_{10}O_{13}P_2$, 673.0927; found, 673.0909. [M+Na, 2H]− monoisotopic mass calculated for $C_{20}H_{24}N_{10}O_{13}P_2$, 695.0752; found, 695.0728.

G. Luciferase Assay

HEK293T cells were plated in TC-treated 96-well plates at 0.5%°-%106% cells % ml-1. The next day, the cells were transfected with indicated constructs, together with IFN-β-firefly luciferase and TK Renilla luciferase reporter constructs. Following stimulation for 6% h with the indicated ligands, the cells were lysed in passive lysis buffer (Promega) for 5% min at 25° C. The cell lysates were incubated with firefly luciferase substrate (Biosynth) and the Renilla luciferase substrate coelenterazine (Biotium), and luminescence was measured on a SpectraMax L microplate reader (Molecular Devices). The relative Ifnb expression was calculated as firefly luminescence relative to Renilla luminescence.

H. In Vitro Cyclic-Di-Nucleotide Synthesis

In vitro DncV reactions were carried out in 20 mM Tris-Cl, pH=8, 20 Mg(OAc)$_2$, 10% glycerol and 1 mM DTT, 0.1 mg/mL BSA. Reactions contained 250 μM GTP, 250 μM ATP or 125 μM GTP and 125 μM ATP as indicated in figures. In addition, 33 nM α32P-GTP (3000 Ci/mmol, Perkin-Elmer) or 33 nM α32P-ATP (3000 Ci/mmol, Perkin-Elmer) was included in reaction where indicated. Reactions were started by addition of 1 μM purified DncV protein. In vitro cGAS reactions were carried out in 40 mM Tris-Cl, pH=7.5, 100 mM NaCl, 10 mM MgCl$_2$. Cold nucleotide and alpha-labeled GTP is at the same concentrations as in DncV reactions. Reactions were started by addition of 200 nM purified cGAS. Where indicated, herring testes DNA (Sigma) was added to reactions at a final concentration of 0.1 mg/mL. WspR reactions were performed as described previously (14). Reactions were incubated for 1 hour at 37° C., boiled for 5 min at 95° C., and spun for 10 minutes at 13,000 rpm. Reactions were removed and mixed 1:5 with TLC running buffer (1:1.5 (v/v) saturated NH$_4$SO$_4$ and 1.5M KH$_2$PO$_4$, pH 3.6) and spotted on PEIcellulose TLC plate (Sigma). Following solvent migration, the TLC plate was exposed to a phosphorimager screen and imaged using Typhoon scanner. For in vitro product transfection into 293T cells, reactions were scaled up, radiolabeled nucleotide was omitted and the concentration of ATP and GTP was increased to 2 mM.

I. Nuclease Digests

Nuclease P1 from *Penicillium citrinum* and Snake venom phosphodiesterase I from *Crotalus adamanteus* were purchased from Sigma. Reactions from in vitro cyclic-di-nucleotide synthesis labeled with α32P-GTP were diluted 1:5 in either P1 buffer (40 mM Tris-Cl, pH=6, 2 mM ZnCl$_2$) or SVPD buffer (40 mM Tris-Cl, pH=8, 10 mM MgCl$_2$) followed by digestion with 2.5 mU of nuclease P1 or SVPD, respectively. Digestions were incubated for 45 minutes at 37° C. and nucleotide products were resolved by TLC.

J. NMR Data

Figure 7A:
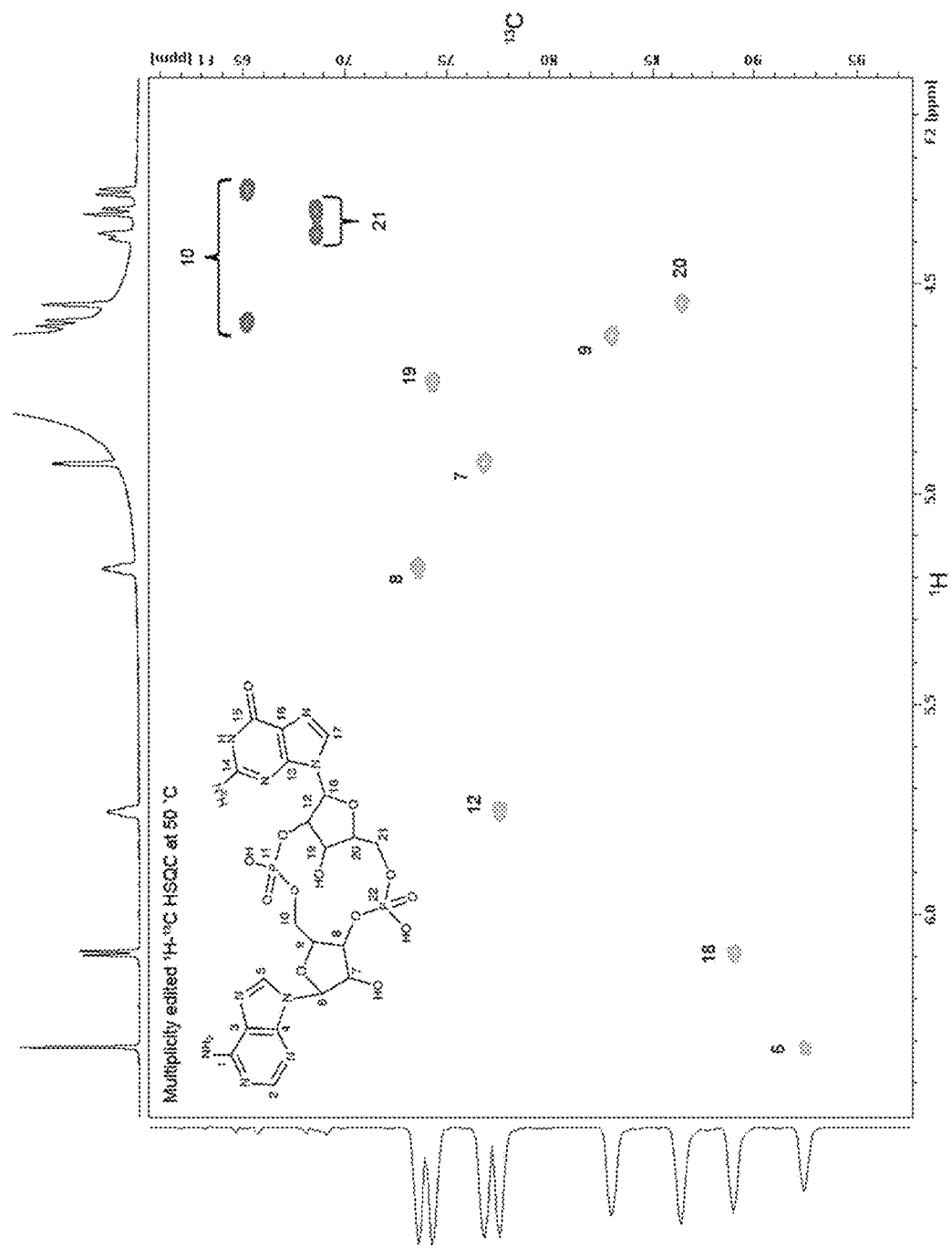
FIG. 7, panels A-D provide additional NMR analysis of the cGAS product. All data acquisition was performed in D2O and at 50° C. (Panels A, B) Multiplicity-edited 1H-13C HSQC experiment in a 900 MHz field. Positive phased signals corresponding to methine and methyl protons are shown in green, negative phased signals corresponding to methylene protons are shown in blue. (Panel C)$^1$H-$^1$H COSY experiment in a 600 MHz field. (Panel D)$^1$H-$^1$H NOESY experiment in a 900 MHz field.
Figure 7B:
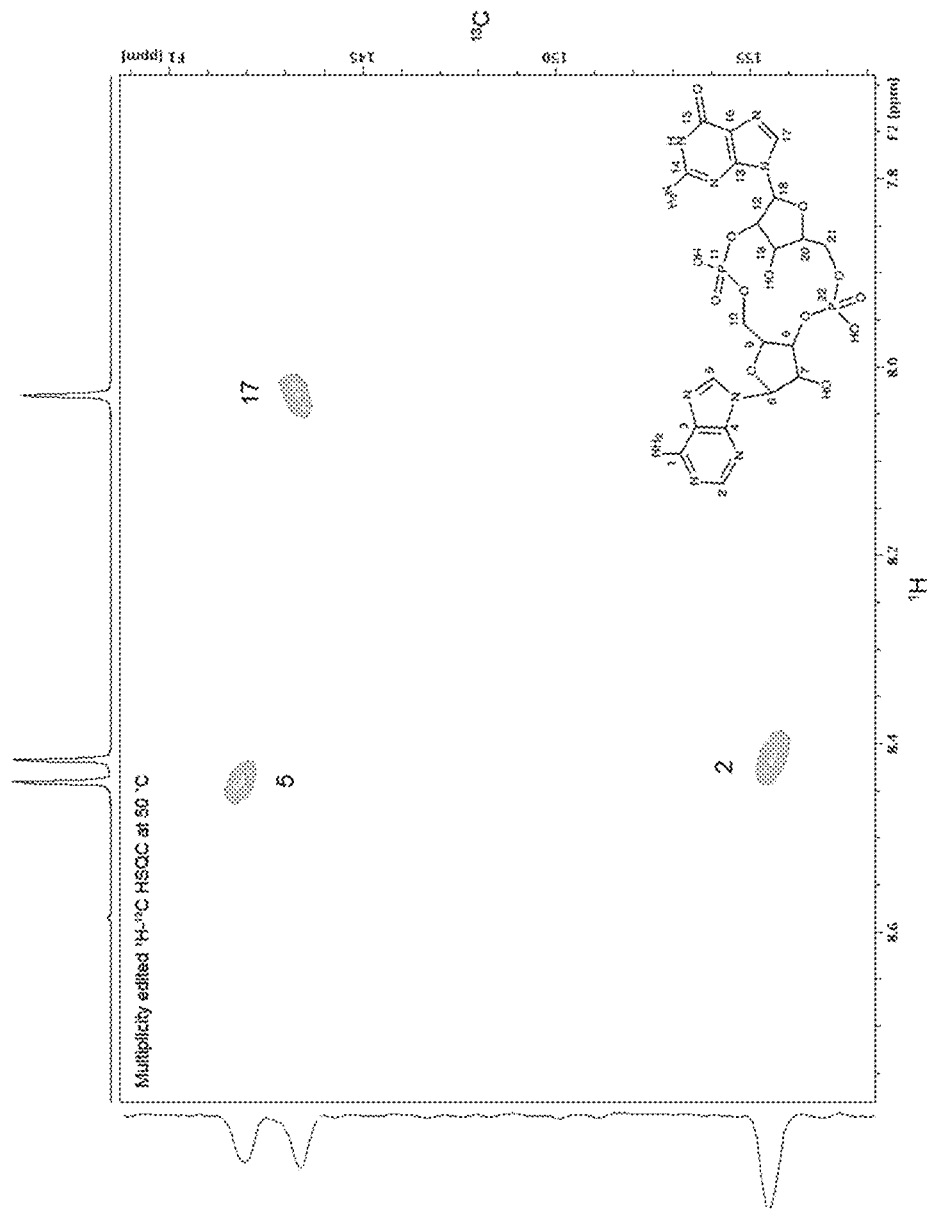
Figure 7C:
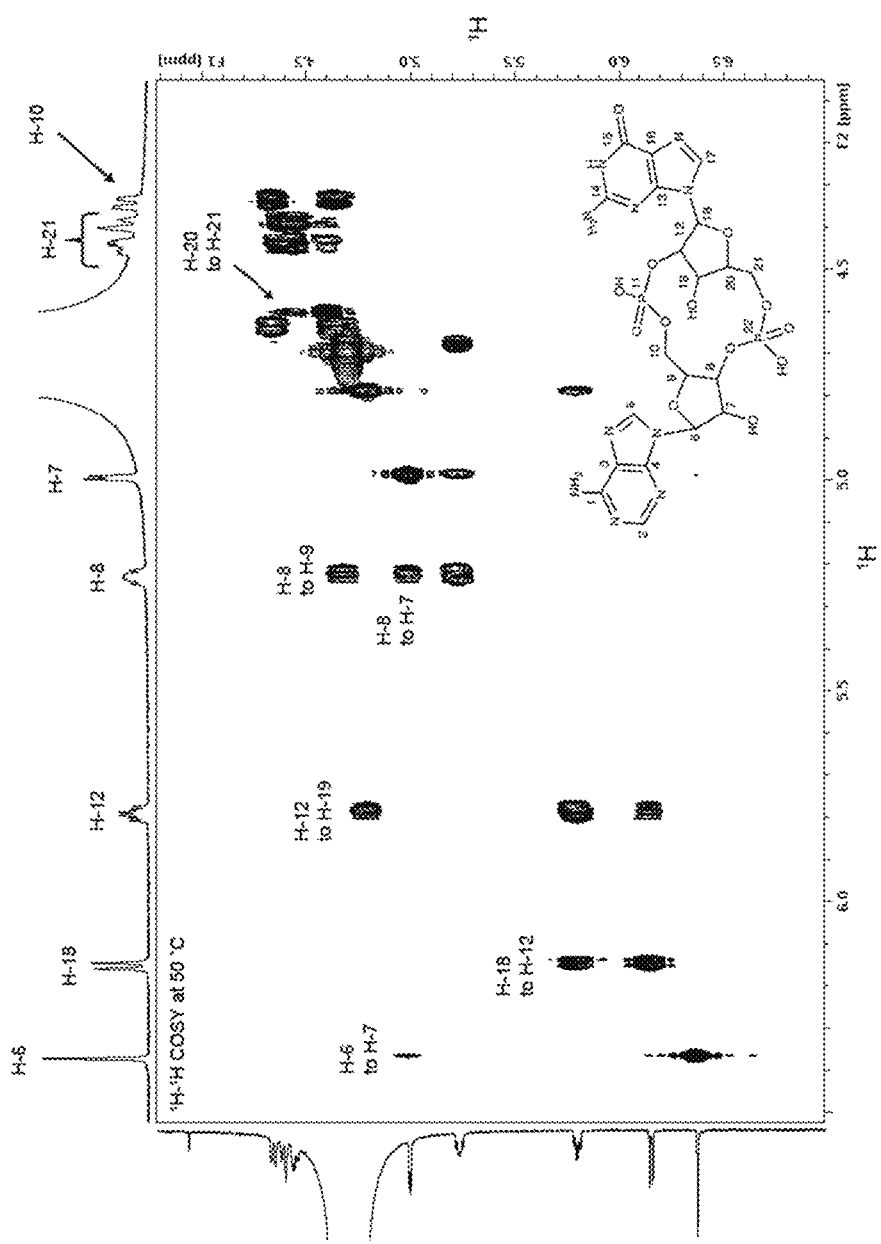
Figure 7D:
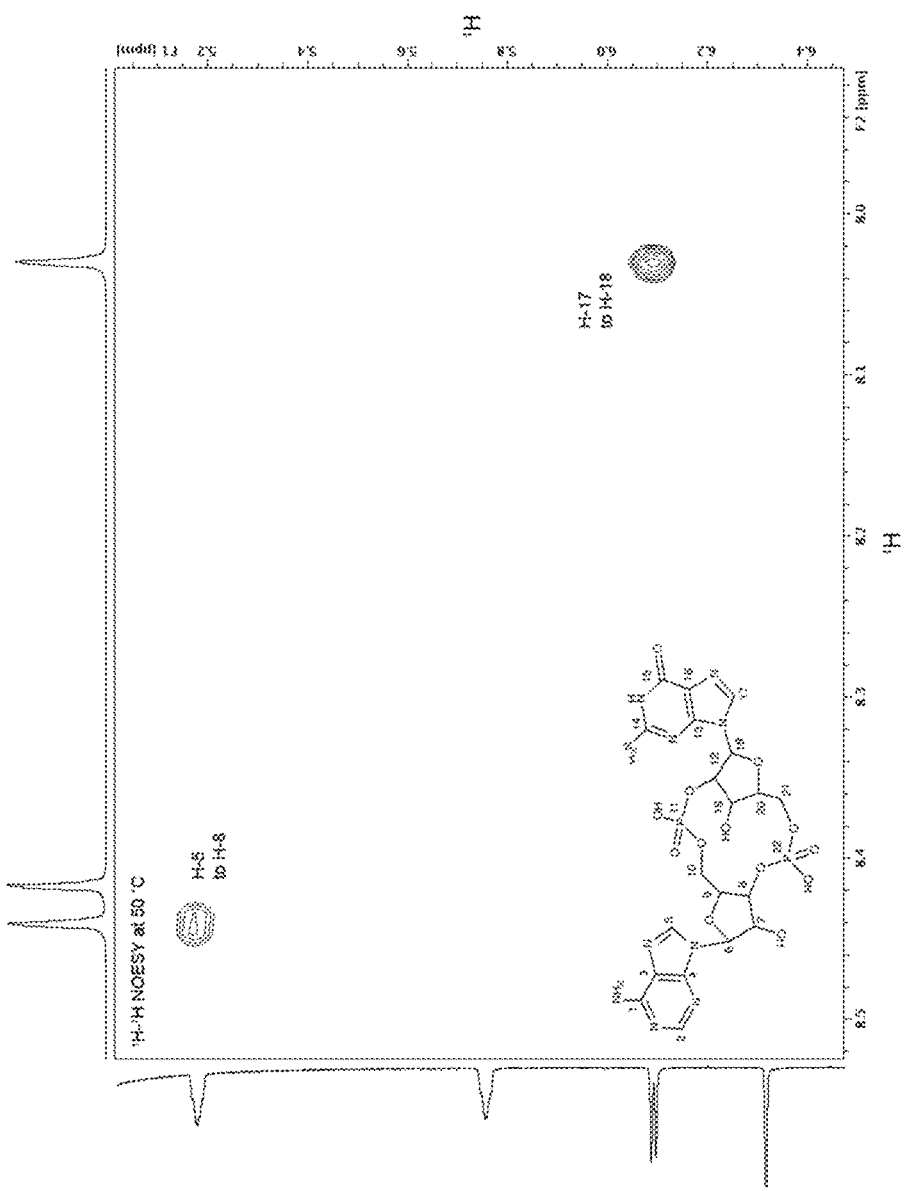

In the $^1H$-$^{31}P$ HMBC spectrum shown in FIG. 6C, the phosphorous nucleus, P-11, is correlated to the 2' ribose proton (H-12) of guanosine as well as to the 5' ribose methylene protons (H-10) and the 4' ribose proton (H-9) of adenosine. The other phosphorous nucleus (P-22) is correlated to the 3' ribose proton (H-8) of adenosine as well as to the 5' ribose methylene protons (H-21) and 4' ribose proton (H-20) of guanosine. Thus, the regiochemistry of the phosphodiester linkages was determined to be cyclic[G(2'-5')pA (3'-5')p]. In order to assign the above peaks, it was critical to accurately identify the ribose spin systems corresponding to guanosine and adenosine, respectively. The protons corresponding to the adenine nucleobase (H-2, H-5) and guanine nucleobase (H-17) were assigned based upon reference spectra for the individual nucleobases, $^1H$-$^{13}C$ HMBC, and $^1H$-$^{13}C$ HSQC NMR (FIGS. 7A and 7B). The $^1H$-$^1H$ NOESY experiment showed through-space interactions between the adenine proton H-5 and the 3' ribose proton (H-8) as well as between the guanine proton H-17 and the 1' ribose proton (H-18) (FIG. 7D). The remaining protons in the corresponding ribose spin systems were identified by $^1H$-$^1H$ COSY (FIG. 7C), and multiplicity edited $^1H$-$^{13}C$ HSQC (FIGS. 7A and 7B), which distinguished the 5' methylene protons in particular (H-10 and H-21).

K. RNA, cDNA Synthesis, and Quantitative RT-PCR

RNA from mammalian cell lines was extracted using Trizol reagent (Invitrogen) or RNeasy Mini Kit (Qiagen). RNA was treated with RQ1 RNase-free DNase (Promega). RNA was reverse transcribed with Superscript III (Invitrogen). Mouse ifnB was quantified relative to mouse rps17 as described previously (Woodward et al). Human ifnB was quantified relative to human S9 as described previously (Wu et al).

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

That which is claimed is:

1. A method for increasing the production of a type I interferon (IFN) in a cell, the method comprising:
   contacting the cell with a 2'-5' phosphodiester linkage comprising cyclic-di-nucleotide to increase production of the type I interferon (IFN) by the cell.

2. The method according to claim 1, wherein the cyclic-di-nucleotide comprises a two 2'-5' phosphodiester linkage.

3. The method according to claim 2, wherein the cyclic-di-nucleotide comprises a 2'5' phosphodiester linkage and a 3'-5' phosphodiester linkage.

4. The method according to claim 1, wherein the cyclic-di-nucleotide comprises a guanosine nucleoside.

5. The method according to claim 4, wherein the cyclic-di-nucleotide comprises two guanosine nucleosides.

6. The method according to claim 1, wherein the cyclic-di-nucleotide comprises an adenosine nucleoside.

7. The method according to claim 6, wherein the cyclic-di-nucleotide comprises two adenosine nucleosides.

8. The method according to claim 1, wherein the cyclic-di-nucleotide comprises an adenosine nucleoside and a guanosine nucleoside.

9. The method according to claim 1, wherein the cyclic-di-nucleotide is described by the formula:

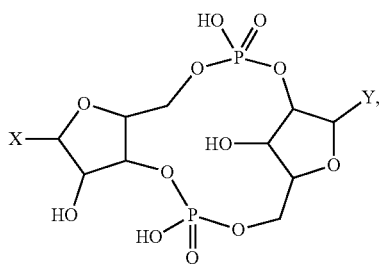

wherein X and Y are each:

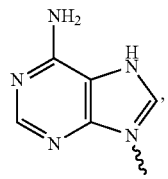 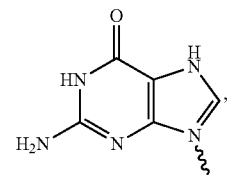

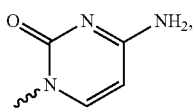 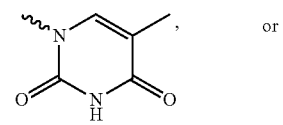 or

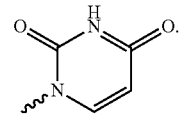

10. The method according to claim 9, wherein the cyclic-di-nucleotide is described by the formula:

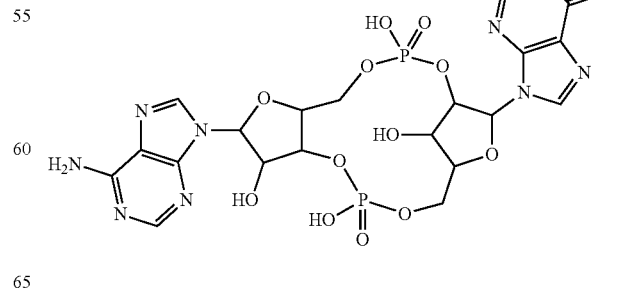

11. The method according to claim 1, wherein the cyclic-di-nucleotide is described by the formula:

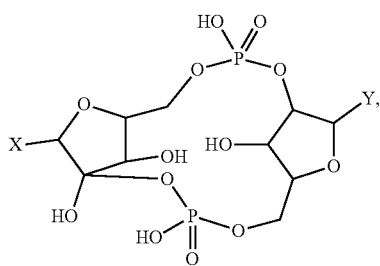

wherein X and Y are each:

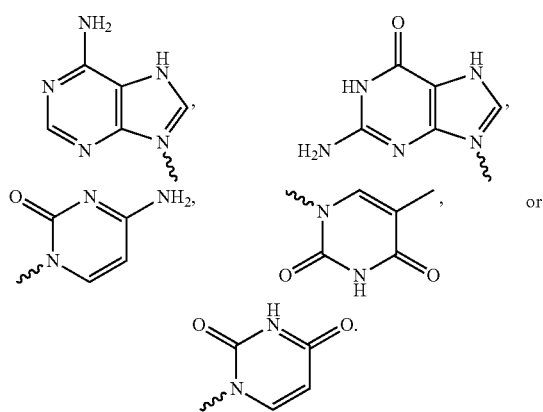

12. The method according to claim 1, wherein the level of the cyclic-di-nucleotide is increased by increasing the activity of a cGAMP synthase (cGAS) in the cell.

13. The method according to claim 1, wherein the IFN is interferon alpha.

14. The method according to claim 1, wherein the IFN is interferon beta.

15. The method according to claim 1, wherein the cell is a mammalian cell.

16. The method according to claim 15, wherein the mammalian cell is a human cell.

17. A method for increasing the production of a type I interferon (IFN) in a subject, the method comprising:

administering to the subject an amount of a 2'-5' phosphodiester linkage comprising cyclic-di-nucleotide active agent effective to increase the production of the type I interferon in the subject.

18. A method for increasing a stimulator of interferon genes (STING) mediated response in a subject, the method comprising:

administering to the subject an amount of a 2'-5' Phosphodiester linkage comprising cyclic-di-nucleotide effective to increase a STING mediated response in the subject.

* * * * *

SEQUENCE LISTING

<160> NUMBER OF SEQ ID NOS: 23

<210> SEQ ID NO 1
<211> LENGTH: 1802
<212> TYPE: DNA
<213> ORGANISM: Homo sapiens

<400> SEQUENCE: 1

```
agcctggggt tccccttcgg gtcgcagact cttgtgtgcc cgccagtagt gcttggtttc      60
caacagctgc tgctggctct tcctcttgcg gccttttcct gaaacggatt cttctttcgg     120
ggaacagaaa gcgccagcca tgcagccttg gcacggaaag gccatgcaga gagcttccga     180
ggccggagcc actgccccca aggcttccgc acggaatgcc aggggcgccc cgatggatcc     240
caccgagtct ccggctgccc ccgaggccgc cctgcctaag gcgggaaagt tcggccccgc     300
caggaagtcg ggatcccggc agaaaaagag cgccccggac acccaggaga ggccgcccgt     360
ccgcgcaact ggggcccgcg ccaaaaaggc ccctcagcgc gcccaggaca cgcagccgtc     420
tgacgccacc agcgcccctg gggcagaggg gctggagcct cctgcggctc gggagccggc     480
tctttccagg gctggttctt gccgccagag gggcgcgcgc tgctccacga agccaagacc     540
tccgcccggg ccctgggacg tgcccagccc cggcctgccg gtctcggccc ccattctcgt     600
acggagggat gcggcgcctg gggcctcgaa gctccgggcg gttttggaga agttgaagct     660
cagccgcgat gatatctcca cggcggcggg gatggtgaaa gggggttgtgg accacctgct     720 gctcagactg aagtgcgact ccgcgttcag aggcgtcggg ctgctgaaca ccgggagcta     780
ctatgagcac gtgaagattt ctgcacctaa tgaatttgat gtcatgttta aactggaagt     840
ccccagaatt caactagaag aatattccaa cactcgtgca tattactttg tgaaatttaa     900
aagaaatccg aaagaaaatc ctctgagtca gtttttagaa ggtgaaatat tatcagcttc     960
taagatgctg tcaaagttta ggaaaatcat taaggaagaa attaacgaca ttaaagatac    1020
agatgtcatc atgaagagga aaagaggagg gagccctgct gtaacacttc ttattagtga    1080
aaaaatatct gtggatataa ccctggcttt ggaatcaaaa agtagctggc ctgctagcac    1140
ccaagaaggc ctgcgcattc aaaactggct ttcagcaaaa gttaggaagc aactacgact    1200
aaagccattt taccttgtac ccaagcatgc aaaggaagga aatggtttcc aagaagaaac    1260
atggcggcta tccttctctc acatcgaaaa ggaaattttg aacaatcatg gaaaatctaa    1320
aacgtgctgt gaaaacaaag aagagaaatg ttgcaggaaa gattgtttaa aactaatgaa    1380
atacctttta gaacagctga agaaaggtt taaagacaaa aacatctgg ataaattctc    1440 ttcttatcat gtgaaaactg ccttctttca cgtatgtacc cagaaccctc aagacagtca    1500
gtgggaccgc aaagacctgg gcctctgctt tgataactgc gtgacatact tcttcagtg    1560 cctcaggaca gaaaaacttg agaattattt tattcctgaa ttcaatctat tctctagcaa    1620
cttaattgac aaaagaagta aggaatttct gacaaagcaa attgaatatg aaagaaacaa    1680
tgagtttcca gttttttgatg aattttgaga ttgtatttt agaaagatct aagaactaga    1740
```

```
gtcaccctaa atcctggaga atacaagaaa aatttgaaaa ggggccagac gctgtggctc    1800
ac                                                                  1802
```

<210> SEQ ID NO 2
<211> LENGTH: 522
<212> TYPE: PRT
<213> ORGANISM: Homo sapiens

<400> SEQUENCE: 2

```
Met Gln Pro Trp His Gly Lys Ala Met Gln Arg Ala Ser Glu Ala Gly
1               5                   10                  15

Ala Thr Ala Pro Lys Ala Ser Ala Arg Asn Ala Arg Gly Ala Pro Met
            20                  25                  30

Asp Pro Thr Glu Ser Pro Ala Ala Pro Glu Ala Ala Leu Pro Lys Ala
        35                  40                  45

Gly Lys Phe Gly Pro Ala Arg Lys Ser Gly Ser Arg Gln Lys Lys Ser
    50                  55                  60

Ala Pro Asp Thr Gln Glu Arg Pro Pro Val Arg Ala Thr Gly Ala Arg
65                  70                  75                  80

Ala Lys Lys Ala Pro Gln Arg Ala Gln Asp Thr Gln Pro Ser Asp Ala
                85                  90                  95

Thr Ser Ala Pro Gly Ala Glu Gly Leu Glu Pro Pro Ala Ala Arg Glu
            100                 105                 110

Pro Ala Leu Ser Arg Ala Gly Ser Cys Arg Gln Arg Gly Ala Arg Cys
        115                 120                 125

Ser Thr Lys Pro Arg Pro Pro Gly Pro Trp Asp Val Pro Ser Pro
    130                 135                 140

Gly Leu Pro Val Ser Ala Pro Ile Leu Val Arg Arg Asp Ala Ala Pro
145                 150                 155                 160

Gly Ala Ser Lys Leu Arg Ala Val Leu Glu Lys Leu Lys Leu Ser Arg
                165                 170                 175

Asp Asp Ile Ser Thr Ala Ala Gly Met Val Lys Gly Val Val Asp His
            180                 185                 190

Leu Leu Leu Arg Leu Lys Cys Asp Ser Ala Phe Arg Gly Val Gly Leu
        195                 200                 205

Leu Asn Thr Gly Ser Tyr Tyr Glu His Val Lys Ile Ser Ala Pro Asn
    210                 215                 220

Glu Phe Asp Val Met Phe Lys Leu Glu Val Pro Arg Ile Gln Leu Glu
225                 230                 235                 240

Glu Tyr Ser Asn Thr Arg Ala Tyr Tyr Phe Val Lys Phe Lys Arg Asn
                245                 250                 255

Pro Lys Glu Asn Pro Leu Ser Gln Phe Leu Glu Gly Glu Ile Leu Ser
            260                 265                 270

Ala Ser Lys Met Leu Ser Lys Phe Arg Lys Ile Ile Lys Glu Glu Ile
        275                 280                 285

Asn Asp Ile Lys Asp Thr Asp Val Ile Met Lys Arg Lys Arg Gly Gly
    290                 295                 300

Ser Pro Ala Val Thr Leu Leu Ile Ser Glu Lys Ile Ser Val Asp Ile
305                 310                 315                 320

Thr Leu Ala Leu Glu Ser Lys Ser Ser Trp Pro Ala Ser Thr Gln Glu
                325                 330                 335

Gly Leu Arg Ile Gln Asn Trp Leu Ser Ala Lys Val Arg Lys Gln Leu
            340                 345                 350
```

```
Arg Leu Lys Pro Phe Tyr Leu Val Pro Lys His Ala Lys Glu Gly Asn
            355                 360                 365

Gly Phe Gln Glu Glu Thr Trp Arg Leu Ser Phe Ser His Ile Glu Lys
    370                 375                 380

Glu Ile Leu Asn Asn His Gly Lys Ser Lys Thr Cys Cys Glu Asn Lys
385                 390                 395                 400

Glu Glu Lys Cys Cys Arg Lys Asp Cys Leu Lys Leu Met Lys Tyr Leu
                405                 410                 415

Leu Glu Gln Leu Lys Glu Arg Phe Lys Asp Lys Lys His Leu Asp Lys
            420                 425                 430

Phe Ser Ser Tyr His Val Lys Thr Ala Phe His Val Cys Thr Gln
        435                 440                 445

Asn Pro Gln Asp Ser Gln Trp Asp Arg Lys Asp Leu Gly Leu Cys Phe
    450                 455                 460

Asp Asn Cys Val Thr Tyr Phe Leu Gln Cys Leu Arg Thr Glu Lys Leu
465                 470                 475                 480

Glu Asn Tyr Phe Ile Pro Glu Phe Asn Leu Ser Ser Asn Leu Ile
                485                 490                 495

Asp Lys Arg Ser Lys Glu Phe Leu Thr Lys Gln Ile Glu Tyr Glu Arg
            500                 505                 510

Asn Asn Glu Phe Pro Val Phe Asp Glu Phe
        515                 520

<210> SEQ ID NO 3
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 3

Arg Gln Ile Lys Ile Trp Phe Gln Asn Arg Arg Met Lys Trp Lys Lys
1               5                   10                  15

<210> SEQ ID NO 4
<211> LENGTH: 2191
<212> TYPE: DNA
<213> ORGANISM: Homo sapiens

<400> SEQUENCE: 4
gttcattttt cactcctccc tcctaggtca cacttttcag aaaaagaatc tgcatcctgg      60
aaaccagaag aaaatatga gacggggaat catcgtgtga tgtgtgtgct gcctttggct     120
gagtgtgtgg agtcctgctc aggtgttagg tacagtgtgt ttgatcgtgg tggcttgagg     180
ggaacccgct gttcagagct gtgactgcgg ctgcactcag agaagctgcc cttggctgct     240
cgtagcgccg ggccttctct cctcgtcatc atccagagca gccagtgtcc gggaggcaga     300
agatgcccca ctccagcctg catccatcca tcccgtgtcc caggggtcac ggggcccaga     360
aggcagcctt ggttctgctg agtgcctgcc tggtgaccct ttgggggcta ggagagccac     420
cagagcacac tctccggtac ctggtgctcc acctagcctc cctgcagctg ggactgctgt     480 taaacgggt ctgcagcctg gctgaggagc tgcgccacat ccactccagg taccggggca     540
gctactggag gactgtgcgg gcctgcctgg ctgccccct ccgccgtggg gccctgttgc     600
tgctgtccat ctatttctac tactccctcc caaatgcggt cggcccgccc ttcacttgga     660
tgcttgccct cctgggcctc tcgcaggcac tgaacatcct cctgggcctc aagggcctgg     720
ccccagctga gatctctgca gtgtgtgaaa aagggaattt caacgtggcc catgggctgg     780
```

```
catggtcata ttacatcgga tatctgcggc tgatcctgcc agagctccag gcccggattc    840
gaacttacaa tcagcattac aacaacctgc tacggggtgc agtgagccag cggctgtata    900
ttctcctccc attggactgt ggggtgcctg ataacctgag tatggctgac cccaacattc    960
gcttcctgga taaactgccc cagcagaccg gtgaccatgc tggcatcaag gatcgggttt   1020
acagcaacag catctatgag cttctggaga cgggcagcg gcgggcacc tgtgtcctgg     1080 agtacgccac ccccttgcag actttgtttg ccatgtcaca atacagtcaa gctggcttta   1140
gccgggagga taggcttgag caggccaaac tcttctgccg gacacttgag gacatcctgg   1200
cagatgcccc tgagtctcag aacaactgcc gcctcattgc ctaccaggaa cctgcagatg   1260
acagcagctt ctcgctgtcc caggaggttc tccggcacct gcggcaggag gaaaaggaag   1320
aggttactgt gggcagcttg aagacctcag cggtgcccag tacctccacg atgtcccaag   1380
agcctgagct cctcatcagt ggaatggaaa agcccctccc tctccgcacg gatttctctt   1440
gagacccagg gtcaccaggc cagagcctcc agtggtctcc aagcctctgg actgggggct   1500
ctcttcagtg gctgaatgtc agcagagct atttccttcc acgggggcc ttgcagggaa      1560 gggtccagga cttgacatct taagatgcgt cttgtcccct tgggccagtc atttcccctc   1620
tctgagcctc ggtgtcttca acctgtgaaa tgggatcata atcactgcct acctccctc    1680 acggttgttg tgaggactga gtgtgtggaa gtttttcata aactttggat gctagtgtac   1740 ttaggggtg tgccaggtgt ctttcatggg gccttccaga cccactcccc acccttctcc    1800
ccttcctttg cccggggacg ccgaactctc tcaatggtat caacaggctc cttcgccctc   1860
tggctcctgg tcatgttcca ttattgggga gccccagcag aagaatggag aggaggagga   1920
ggctgagttt ggggtattga atccccggc tcccaccctg cagcatcaag gttgctatgg    1980
actctcctgc cgggcaactc ttgcgtaatc atgactatct ctaggattct ggcaccactt   2040
ccttccctgg cccttaagc ctagctgtgt atcggcaccc ccacccccact agagtactcc    2100 ctctcacttg cggtttcctt atactccacc cctttctcaa cggtccttt ttaaagcaca    2160 tctcagatta cccaaaaaaa aaaaaaaaa a                                    2191
```

<210> SEQ ID NO 5
<211> LENGTH: 379
<212> TYPE: PRT
<213> ORGANISM: Homo sapiens

<400> SEQUENCE: 5

Met Pro His Ser Ser Leu His Pro Ser Ile Pro Cys Pro Arg Gly His
1               5                   10                  15

Gly Ala Gln Lys Ala Ala Leu Val Leu Leu Ser Ala Cys Leu Val Thr
            20                  25                  30

Leu Trp Gly Leu Gly Glu Pro Pro Glu His Thr Leu Arg Tyr Leu Val
        35                  40                  45

Leu His Leu Ala Ser Leu Gln Leu Gly Leu Leu Asn Gly Val Cys
    50                  55                  60

Ser Leu Ala Glu Glu Leu Arg His Ile His Ser Arg Tyr Arg Gly Ser
65                  70                  75                  80

Tyr Trp Arg Thr Val Arg Ala Cys Leu Gly Cys Pro Leu Arg Arg Gly
                85                  90                  95

Ala Leu Leu Leu Leu Ser Ile Tyr Phe Tyr Tyr Ser Leu Pro Asn Ala
            100                 105                 110

Val Gly Pro Pro Phe Thr Trp Met Leu Ala Leu Leu Gly Leu Ser Gln

```
            115                 120                 125
Ala Leu Asn Ile Leu Leu Gly Leu Lys Gly Leu Ala Pro Ala Glu Ile
    130                 135                 140

Ser Ala Val Cys Glu Lys Gly Asn Phe Asn Val Ala His Gly Leu Ala
145                 150                 155                 160

Trp Ser Tyr Tyr Ile Gly Tyr Leu Arg Leu Ile Leu Pro Glu Leu Gln
                165                 170                 175

Ala Arg Ile Arg Thr Tyr Asn Gln His Tyr Asn Asn Leu Leu Arg Gly
            180                 185                 190

Ala Val Ser Gln Arg Leu Tyr Ile Leu Leu Pro Leu Asp Cys Gly Val
        195                 200                 205

Pro Asp Asn Leu Ser Met Ala Asp Pro Asn Ile Arg Phe Leu Asp Lys
    210                 215                 220

Leu Pro Gln Gln Thr Gly Asp His Ala Gly Ile Lys Asp Arg Val Tyr
225                 230                 235                 240

Ser Asn Ser Ile Tyr Glu Leu Leu Glu Asn Gly Gln Arg Ala Gly Thr
                245                 250                 255

Cys Val Leu Glu Tyr Ala Thr Pro Leu Gln Thr Leu Phe Ala Met Ser
            260                 265                 270

Gln Tyr Ser Gln Ala Gly Phe Ser Arg Glu Asp Arg Leu Glu Gln Ala
        275                 280                 285

Lys Leu Phe Cys Arg Thr Leu Glu Asp Ile Leu Ala Asp Ala Pro Glu
    290                 295                 300

Ser Gln Asn Asn Cys Arg Leu Ile Ala Tyr Gln Glu Pro Ala Asp Asp
305                 310                 315                 320

Ser Ser Phe Ser Leu Ser Gln Glu Val Leu Arg His Leu Arg Gln Glu
                325                 330                 335

Glu Lys Glu Glu Val Thr Val Gly Ser Leu Lys Thr Ser Ala Val Pro
            340                 345                 350

Ser Thr Ser Thr Met Ser Gln Glu Pro Glu Leu Leu Ile Ser Gly Met
        355                 360                 365

Glu Lys Pro Leu Pro Leu Arg Thr Asp Phe Ser
    370                 375

<210> SEQ ID NO 6
<211> LENGTH: 379
<212> TYPE: PRT
<213> ORGANISM: Artificial Sequence
<220> FEATURE:
<223> OTHER INFORMATION: Derived from Homo sapiens

<400> SEQUENCE: 6

Met Pro His Ser Ser Leu His Pro Ser Ile Pro Cys Pro Arg Gly His
1               5                   10                  15

Gly Ala Gln Lys Ala Ala Leu Val Leu Leu Ser Ala Cys Leu Val Thr
            20                  25                  30

Leu Trp Gly Leu Gly Glu Pro Pro Glu His Thr Leu Arg Tyr Leu Val
        35                  40                  45

Leu His Leu Ala Ser Leu Gln Leu Gly Leu Leu Leu Asn Gly Val Cys
    50                  55                  60

Ser Leu Ala Glu Glu Leu His His Ile His Ser Arg Tyr Arg Gly Ser
65                  70                  75                  80

Tyr Trp Arg Thr Val Arg Ala Cys Leu Gly Cys Pro Leu Arg Arg Gly
                85                  90                  95

Ala Leu Leu Leu Leu Ser Ile Tyr Phe Tyr Tyr Ser Leu Pro Asn Ala
```

```
            100                 105                 110
Val Gly Pro Phe Thr Trp Met Leu Ala Leu Leu Gly Leu Ser Gln
            115                 120                 125
Ala Leu Asn Ile Leu Gly Leu Lys Gly Leu Ala Pro Ala Glu Ile
            130                 135                 140
Ser Ala Val Cys Glu Lys Gly Asn Phe Asn Val Ala His Gly Leu Ala
145                 150                 155                 160
Trp Ser Tyr Tyr Ile Gly Tyr Leu Arg Leu Ile Leu Pro Glu Leu Gln
            165                 170                 175
Ala Arg Ile Arg Thr Tyr Asn Gln His Tyr Asn Asn Leu Leu Arg Gly
            180                 185                 190
Ala Val Ser Gln Arg Leu Tyr Ile Leu Leu Pro Leu Asp Cys Gly Val
            195                 200                 205
Pro Asp Asn Leu Ser Met Ala Asp Pro Asn Ile Arg Phe Leu Asp Lys
210                 215                 220
Leu Pro Gln Gln Thr Ala Asp Arg Ala Gly Ile Lys Asp Arg Val Tyr
225                 230                 235                 240
Ser Asn Ser Ile Tyr Glu Leu Leu Glu Asn Gly Gln Arg Ala Gly Thr
            245                 250                 255
Cys Val Leu Glu Tyr Ala Thr Pro Leu Gln Thr Leu Phe Ala Met Ser
            260                 265                 270
Gln Tyr Ser Gln Ala Gly Phe Ser Arg Glu Asp Arg Leu Glu Gln Ala
            275                 280                 285
Lys Leu Phe Cys Gln Thr Leu Glu Asp Ile Leu Ala Asp Ala Pro Glu
            290                 295                 300
Ser Gln Asn Asn Cys Arg Leu Ile Ala Tyr Gln Glu Pro Ala Asp Asp
305                 310                 315                 320
Ser Ser Phe Ser Leu Ser Gln Glu Val Leu Arg His Leu Arg Gln Glu
            325                 330                 335
Glu Lys Glu Glu Val Thr Val Gly Ser Leu Lys Thr Ser Ala Val Pro
            340                 345                 350
Ser Thr Ser Thr Met Ser Gln Glu Pro Glu Leu Leu Ile Ser Gly Met
            355                 360                 365
Glu Lys Pro Leu Pro Leu Arg Thr Asp Phe Ser
            370                 375

<210> SEQ ID NO 7
<211> LENGTH: 21
<212> TYPE: DNA
<213> ORGANISM: Artificial sequence
<220> FEATURE:
<223> OTHER INFORMATION: Synthetic Polynucleotide

<400> SEQUENCE: 7
gcagagctat ttccttccac a                                           21

<210> SEQ ID NO 8
<211> LENGTH: 58
<212> TYPE: DNA
<213> ORGANISM: Artificial sequence
<220> FEATURE:
<223> OTHER INFORMATION: Synthetic Polynucleotide

<400> SEQUENCE: 8
ccgggcagag ctatttcctt ccacactcga gtgtggaagg aaatagctct gcttttg    58

<210> SEQ ID NO 9
```

```
<211> LENGTH: 58
<212> TYPE: DNA
<213> ORGANISM: Artificial sequence
<220> FEATURE:
<223> OTHER INFORMATION: Synthetic Polynucleotide

<400> SEQUENCE: 9
aattcaaaaa gcagagctat ttccttccac actcgagtgt ggaaggaaat agctctgc      58

<210> SEQ ID NO 10
<211> LENGTH: 33
<212> TYPE: DNA
<213> ORGANISM: Artificial sequence
<220> FEATURE:
<223> OTHER INFORMATION: Synthetic Polynucleotide

<400> SEQUENCE: 10
atcgaagctt ccaccatgcc ccactccagc ctg                                 33

<210> SEQ ID NO 11
<211> LENGTH: 62
<212> TYPE: DNA
<213> ORGANISM: Artificial sequence
<220> FEATURE:
<223> OTHER INFORMATION: Synthetic Polynucleotide

<400> SEQUENCE: 11
atcggcggcc gctcaggcat agtcaggcac gtcataagga taagagaaat ccgtgcggag    60
ag                                                                   62

<210> SEQ ID NO 12
<211> LENGTH: 33
<212> TYPE: DNA
<213> ORGANISM: Artificial sequence
<220> FEATURE:
<223> OTHER INFORMATION: Synthetic Polynucleotide

<400> SEQUENCE: 12
atcgctcgag ccaccatgcc ccactccagc ctg                                 33

<210> SEQ ID NO 13
<211> LENGTH: 60
<212> TYPE: DNA
<213> ORGANISM: Artificial sequence
<220> FEATURE:
<223> OTHER INFORMATION: Synthetic Polynucleotide

<400> SEQUENCE: 13
atcgggtacc ccaccatgga ttacaaggat gacgatgaca aggaagatcc gcgtagaagg    60

<210> SEQ ID NO 14
<211> LENGTH: 33
<212> TYPE: DNA
<213> ORGANISM: Artificial sequence
<220> FEATURE:
<223> OTHER INFORMATION: Synthetic Polynucleotide

<400> SEQUENCE: 14
atcggcggcc gctcaaagct tgtcaaaaat tgg                                 33

<210> SEQ ID NO 15
<211> LENGTH: 60
<212> TYPE: DNA
<213> ORGANISM: Artificial sequence
<220> FEATURE:
<223> OTHER INFORMATION: Synthetic Polynucleotide
```

<400> SEQUENCE: 15
atcgggtacc ccaccatgga ttacaaggat gacgatgaca agcagccttg gcacggaaag    60

<210> SEQ ID NO 16
<211> LENGTH: 37
<212> TYPE: DNA
<213> ORGANISM: Artificial sequence
<220> FEATURE:
<223> OTHER INFORMATION: Synthetic Polynucleotide

<400> SEQUENCE: 16
atcggcggcc gctcaaaatt catcaaaaac tggaaac    37

<210> SEQ ID NO 17
<211> LENGTH: 37
<212> TYPE: DNA
<213> ORGANISM: Artificial sequence
<220> FEATURE:
<223> OTHER INFORMATION: Synthetic Polynucleotide

<400> SEQUENCE: 17
gcatggatcc gccaccatga cttggaactt tcaccag    37

<210> SEQ ID NO 18
<211> LENGTH: 35
<212> TYPE: DNA
<213> ORGANISM: Artificial sequence
<220> FEATURE:
<223> OTHER INFORMATION: Synthetic Polynucleotide

<400> SEQUENCE: 18
gcatgcggcc gctcagccac ttaccattgt gctgc    35

<210> SEQ ID NO 19
<211> LENGTH: 36
<212> TYPE: DNA
<213> ORGANISM: Artificial sequence
<220> FEATURE:
<223> OTHER INFORMATION: Synthetic Polynucleotide

<400> SEQUENCE: 19
gcatctcgag ccaccatgac ttggaactt caccag    36

<210> SEQ ID NO 20
<211> LENGTH: 30
<212> TYPE: DNA
<213> ORGANISM: Artificial sequence
<220> FEATURE:
<223> OTHER INFORMATION: Synthetic Polynucleotide

<400> SEQUENCE: 20
taataaggag atataccatg ggcagcagcc    30

<210> SEQ ID NO 21
<211> LENGTH: 33
<212> TYPE: DNA
<213> ORGANISM: Artificial sequence
<220> FEATURE:
<223> OTHER INFORMATION: Synthetic Polynucleotide

<400> SEQUENCE: 21
gaattcgtcg acaccaatct gttctctgtg agc    33

<210> SEQ ID NO 22

```
<211> LENGTH: 33
<212> TYPE: DNA
<213> ORGANISM: Artificial sequence
<220> FEATURE:
<223> OTHER INFORMATION: Synthetic Polynucleotide

<400> SEQUENCE: 22
gatgtcgaca tggaagatcc gcgtagaagg acg                             33

<210> SEQ ID NO 23
<211> LENGTH: 35
<212> TYPE: DNA
<213> ORGANISM: Artificial sequence
<220> FEATURE:
<223> OTHER INFORMATION: Synthetic Polynucleotide

<400> SEQUENCE: 23
atcctcgagt caaagcttgt caaaaattgg aaacc                           35
```